US008895117B2

(12) United States Patent
Jansen et al.

(10) Patent No.: US 8,895,117 B2
(45) Date of Patent: Nov. 25, 2014

(54) POLYMERISABLE COMPOUNDS AND THE USE THEREOF IN LIQUID-CRYSTAL MEDIA AND LIQUID-CRYSTAL DISPLAYS

(75) Inventors: Axel Jansen, Darmstadt (DE); Andreas Taugerbeck, Darmstadt (DE); Helmut Haensel, Muehltal (DE); Achim Goetz, Alsbach-Haehnlein (DE)

(73) Assignee: Merck Patent GmbH, Darmstadt (DE)

( * ) Notice: Subject to any disclaimer, the term of this patent is extended or adjusted under 35 U.S.C. 154(b) by 152 days.

(21) Appl. No.: 13/094,256

(22) Filed: Apr. 26, 2011

(65) Prior Publication Data

US 2011/0261311 A1   Oct. 27, 2011

(30) Foreign Application Priority Data

Apr. 26, 2010 (DE) .................. 10 2010 018 188

(51) Int. Cl.
| C09K 19/38 | (2006.01) |
| C09K 19/30 | (2006.01) |
| C09K 19/34 | (2006.01) |
| C09K 19/32 | (2006.01) |
| C09K 19/12 | (2006.01) |
| C09K 19/20 | (2006.01) |
| C09K 19/54 | (2006.01) |
| C07C 69/34 | (2006.01) |
| C07C 69/593 | (2006.01) |
| C07C 69/602 | (2006.01) |
| C07C 69/653 | (2006.01) |
| C08F 16/24 | (2006.01) |
| C09K 19/02 | (2006.01) |
| C09K 19/42 | (2006.01) |
| C09K 19/46 | (2006.01) |
| C09K 19/04 | (2006.01) |

(52) U.S. Cl.
CPC ............. *C09K 19/2007* (2013.01); *C07C 69/34* (2013.01); *C07C 69/653* (2013.01); *C09K 19/0275* (2013.01); *C09K 19/322* (2013.01); *C09K 19/42* (2013.01); *C09K 19/46* (2013.01); *C09K 2019/0448* (2013.01); *C09K 2019/0466* (2013.01); *C09K 2019/0481* (2013.01); *C09K 2019/3408* (2013.01); *C09K 2019/3422* (2013.01); *C09K 2019/3425* (2013.01); *C09K 2019/548* (2013.01)
USPC .................. 428/1.1; 252/299.61; 252/299.63; 252/299.66; 252/299.67; 560/194; 526/247

(58) Field of Classification Search
CPC ........... C09K 19/0275; C09K 19/2007; C09K 19/322; C09K 19/38; C09K 2019/0448; C09K 2019/0466; C09K 2019/0477; C09K 2019/3402; C09K 2019/3425; C09K 2019/3422; C09K 2019/548

USPC .......... 526/242, 247; 560/8, 194; 252/299.61, 252/299.63, 299.66, 299.67; 428/1.1
See application file for complete search history.

(56) References Cited

U.S. PATENT DOCUMENTS

| 6,861,107 B2 | 3/2005 | Klasen-Memmer et al. | |
| 7,070,838 B2 | 7/2006 | Sasada et al. | |
| 7,440,160 B2 | 10/2008 | Heckmeier et al. | |
| 7,767,277 B2 | 8/2010 | Lietzau et al. | |
| 8,236,390 B2 | 8/2012 | Hirschmann et al. | |
| 8,304,035 B2 | 11/2012 | Bernatz et al. | |
| 2003/0078447 A1* | 4/2003 | Kirsch et al. | 558/260 |
| 2004/0011996 A1 | 1/2004 | Klasen-Memmer et al. | |
| 2005/0007541 A1* | 1/2005 | Sasada et al. | 349/183 |
| 2008/0132716 A1 | 6/2008 | Lietzau et al. | |
| 2009/0051855 A1 | 2/2009 | Haseba | |
| 2009/0059132 A1 | 3/2009 | Yamamoto et al. | |
| 2009/0059157 A1 | 3/2009 | Haseba et al. | |
| 2009/0109392 A1 | 4/2009 | Hsieh et al. | |
| 2009/0267025 A1 | 10/2009 | Schott et al. | |
| 2009/0268143 A1* | 10/2009 | Takeuchi et al. | 349/130 |
| 2010/0309423 A1 | 12/2010 | Bernatz et al. | |
| 2010/0320420 A1 | 12/2010 | Hirschmann et al. | |

FOREIGN PATENT DOCUMENTS

| DE | 102008036248 A1 | 3/2009 |
| DE | 102008024866 A1 | 6/2009 |
| EP | 1134826 A1 | 9/2001 |
| EP | 1378557 A1 | 1/2004 |
| EP | 1900792 A1 | 3/2008 |
| JP | 2001-266882 A | 9/2001 |
| JP | 2005-15473 A | 1/2005 |
| WO | WO 2004/046805 A1 | 6/2004 |
| WO | WO 2005/080529 A1 | 9/2005 |
| WO | WO 2006/063662 A1 | 6/2006 |
| WO | WO 2006/112338 A1 | 10/2006 |
| WO | WO 2008/061606 A1 | 5/2008 |

OTHER PUBLICATIONS

English Translation Abstract of JP 2001-266882 A published Sep. 28, 2001.
M. Yasutomi et al., "Synthesis and Electrochemical Properties of Li2-xM(SiO4)1-x(PO4)x (M=Fe, Mn) Positive Active Materials by Hydrothermal Process for Li-ion Cells", GS Yuasa Technical Report, GS Yuasa Corporation (2009) pp. 21-26.

* cited by examiner

*Primary Examiner* — Shean C Wu
(74) *Attorney, Agent, or Firm* — Millen, White, Zelano & Branigan, P.C.

(57) ABSTRACT

The present invention relates to polymerisable compounds, to processes and intermediates for the preparation thereof, to the use thereof for optical, electro-optical and electronic purposes, in particular in liquid-crystal (LC) media and LC displays having a polymer-stabilized blue phase, and in LC media for LC displays of the PS or PSA ("polymer sustained" or "polymer sustained alignment") type, and to LC media and LC displays comprising these compounds.

42 Claims, No Drawings

POLYMERISABLE COMPOUNDS AND THE USE THEREOF IN LIQUID-CRYSTAL MEDIA AND LIQUID-CRYSTAL DISPLAYS

The present invention relates to polymerisable compounds, to processes and intermediates for the preparation thereof, and to the use thereof for optical, electro-optical and electronic purposes, in particular in liquid-crystal (LC) media and LC displays having a polymer-stabilised blue phase, and in LC media for LC displays of the PS or PSA ("polymer sustained" or "polymer sustained alignment") type, and to LC media and LC displays comprising these compounds.

Media for display elements which operate in the liquid-crystalline blue phase (blue phase for short) are known from the prior art. Such displays are described, for example, in WO 2004/046805 A1 and WO 2008/061606 A1.

E The blue phase is generally observed at the transition from the nematic state to the optically isotropic state. The medium in the liquid-crystalline blue phase may be blue, as the name suggests, but also colourless. The aim of efforts to date was to extend the temperature range of the blue phase from less than one degree to a range which is useful in practice (cf. H. Kikuchi et al., Nature Materials (2002), 1 (1), 64-68; Kikuchi, H. et al., Polymeric Materials Science and Engineering, (2003), 89, 90-91).

For this purpose, it has been proposed in the prior art to add a polymerisable compound to the LC medium, and then to polymerise this compound in situ in the LC medium. The polymer or polymer network formed in the process is claimed to stabilise the blue phase.

The polymer-stabilised blue phases described to date in the prior art use, for example, a monoreactive non-mesogenic monomer together with a direactive mesogenic monomer as monomers.

WO 2005/080529 A1 describes, for example, polymer-stabilised blue phases comprising mono- and multireactive monomers.

The present invention was based on the object of finding suitable monomers and corresponding polymers for the stabilisation of blue phases. The polymer is intended, in particular, to have the following effects on the properties of the stabilised LC phase:
broad temperature range of the blue phase,
fast response time,
small clearing-point difference on polymerisation,
low operating voltage ($V_{op}$),
small variation of the operating voltage with temperature,
low hysteresis of the transmission of a cell when the operating voltage is changed in order to achieve defined grey shades.

In addition, monomers which have a good "voltage holding ratio" (VHR), have high clearing points, and are stable to exposure to light and temperature are required. Good solubility in LC materials or good miscibility with the LC medium is furthermore necessary in order to achieve a good distribution in the LC medium.

The present invention is thus based on the object of providing improved polymerisable compounds, and LC media comprising such compounds, in particular for use in LC displays having a polymer-stabilised blue phase. The polymerisable compounds according to the invention are intended to stabilise the blue phase. The LC media according to the invention are intended to have one or more improved properties, in particular selected from the properties mentioned above. In particular, the LC media are intended to have a broad blue phase, enable fast switching, have a good voltage holding ratio (VHR), require low voltages ($V_{op}$) for the switching process and exhibit low hysteresis ($\Delta V$) and have a low memory effect (ME). The LC media are intended to be stable to exposure to light and temperature.

Furthermore, so-called PS and PSA ("polymer sustained" and "polymer sustained alignment" respectively) displays, for which the term "polymer stabilised" is also occasionally used, are known from the prior art. In these displays, a small amount (for example 0.3% by weight, typically <1% by weight) of one or more polymerisable compound(s) is added to the LC medium and, after introduction into the LC cell, is polymerised or crosslinked in situ, usually by UV photopolymerisation, with or without an applied electrical voltage between the electrodes. The addition of polymerisable mesogenic or liquid-crystalline compounds, also known as reactive mesogens or "RMs", to the LC mixture has proven particularly suitable.

The term "PSA" is used below, unless indicated otherwise, as representative of PS displays and PSA displays.

In the meantime, the PS(A) principle is being used in diverse classical LC displays. Thus, for example, PSA-VA, PSA-OCB, PSA-IPS, PSA-FFS and PSA-TN displays are known. The polymerisation of the polymerisable compound(s) is preferably carried out with an applied electrical voltage in the case of PSA-VA and PSA-OCB displays and with or without an applied electrical voltage in the case of PSA-IPS displays. As can be shown in test cells, the PS(A) method results in a "pretilt" in the cell. In the case of PSA-OCB displays, for example, the bend structure can be stabilised, so that an offset voltage is unnecessary or can be reduced. In the case of PSA-VA displays, the pretilt has a positive effect on the response times. For PSA-VA displays, a standard MVA or PVA pixel and electrode layout can be used. In addition, however, only one structured electrode side and no protrusions, for example, are also sufficient, which significantly simplifies production and at the same time results in very good contrast at the same time as very good light transmission.

PSA-VA displays are described, for example, in JP 10-036847 A, EP 1 170 626 A2, U.S. Pat. Nos. 6,861,107, 7,169,449, U.S. 2004/0191428 A1, U.S. 2006/0066793 A1 and U.S. 2006/0103804 A1. PSA-OCB displays are described, for example, in T.-J- Chen et al., Jpn. J. Appl. Phys. 45, 2006, 2702-2704 and S. H. Kim, L.-C- Chien, Jpn. J. Appl. Phys. 43, 2004, 7643-7647. PSA-IPS displays are described, for example, in U.S. Pat. No. 6,177,972 and Appl. Phys. Lett. 1999, 75 (21), 3264. PSA-TN displays are described, for example, in Optics Express 2004, 12 (7), 1221.

PSA displays, like the conventional LC displays described above, can be operated as active-matrix or passive-matrix displays. In the case of active-matrix displays, individual pixels are usually addressed by integrated, non-linear, active elements, such as, for example, transistors (for example thin-film transistors or "TFTs"), while in the case of passive-matrix displays, the addressing is usually carried out by the multiplex method, both methods being known from the prior art.

However, not all combinations consisting of LC mixture and polymerisable component are suitable for PSA displays, since, for example, an inadequate tilt, or none at all, is established or since, for example, the so-called "voltage holding ratio" (VHR or HR) is inadequate for TFT display applications. In addition, it has been found that the LC mixtures and RMs known from the prior art still have some disadvantages on use in PSA displays. Thus, not every known RM which is soluble in LC mixtures is suitable for use in PSA displays.

In addition, the selected combination of LC host mixture/ RM should have the lowest possible rotational viscosity and the best possible electrical properties. In particular, it should have the highest possible VHR. In PSA displays, a high VHR after irradiation with UV light is particularly necessary since UV exposure is a necessary part of the display production process, but also occurs as normal exposure during operation of the finished display.

In particular, it would be desirable to have available novel materials for PSA displays which generate a particularly low pretilt angle. Preference is given here to materials which generate a lower pretilt angle during polymerisation for the same exposure time than the materials known to date, and/or whose use enables the (higher) pretilt angle that can be achieved with the known materials to be achieved already after a shorter exposure time. It was thus possible for the production time ("tact time") of the display to be shortened and for the costs of the production process to be reduced.

A further problem in the production of PSA displays is the presence or removal of residual amounts of unpolymerised RMs, in particular after the polymerisation step for generation of the pretilt angle in the display. For example, unreacted RMs of this type may adversely affect the properties of the display by polymerising in an uncontrolled manner, for example during operation after completion of the display.

Thus, the PSA displays known from the prior art often exhibit the undesired effect of so-called "image sticking" or "image burn", i.e. the image produced in the LC display by temporary addressing of individual pixels still remains visible even after the electric field in these pixels has been switched off, or after other pixels have been addressed.

It is therefore desirable for the polymerisation of the RMs during production of the PSA display to proceed as completely as possible and for the presence of unpolymerised RMs in the display to be excluded as far as possible or reduced to a minimum. To this end, materials which enable the most effective and complete polymerisation possible are required.

There is thus still a great demand for PSA displays and LC media and polymerisable compounds for use in such displays, which do not exhibit the disadvantages described above or only do so to a small extent and have improved properties. In addition, there is a great demand for PSA displays, and materials for use in PSA displays, which have advantageous properties, in particular facilitate a high specific resistance at the same time as a large working-temperature range, short response times, even at low temperatures, and a low threshold voltage, a low pretilt angle, a multiplicity of grey shades, high contrast and a broad viewing angle, and high values of the voltage holding ratio (VHR) after UV exposure and low-temperature stability, also known as LTS, i.e. the stability of the LC mixture to individual components spontaneously crystallising out.

The invention is thus based on the further object of providing novel suitable materials, in particular RMs and LC media comprising the latter, for use in PSA displays which do not have the disadvantages indicated above, or only do so to a reduced extent, polymerise as quickly and completely as possible, enable a low pretilt angle to be established as quickly as possible, reduce or prevent the occurrence of image sticking in the display, and preferably at the same time enable very high specific resistance values, low threshold voltages and short response times. In addition, the LC media should have favourable LC phase properties and high VHR and LTS values.

The objects described above have been achieved in accordance with the invention by the provision of materials, processes and LC displays as described in the present application. In particular, it has been found, surprisingly, that the objects described above can be achieved in part or full by using LC media which comprise one or more polymerisable compounds according to the invention, as described above, for the production of such LC displays or by providing LC displays having a blue phase or PSA displays which contain one or more compounds according to the invention in polymerised form.

The polymerisable compounds according to the invention contain a central mesogenic group and at least two polymerisable groups which are linked to the mesogenic group directly or via spacer groups, where the central mesogenic group consists of three cyclic radicals which are linked to one another by two difluoromethyleneoxy bridges ($CF_2O$ or $OCF_2$).

The use of the polymerisable compounds according to the invention in LC media according to the invention for LC displays having a polymer-stabilised blue phase results in significant stabilisation of the blue phase. In addition, it has been found, surprisingly, that a significant reduction in hysteresis ($\Delta V_{50}$) and an increase in contrast are achieved on use of the polymerisable compounds according to the invention in LC media having a polymer-stabilised blue phase, compared with polymerisable compounds and LC media as described in the prior art.

In PSA displays, the use of the polymerisable compounds according to the invention in LC media according to the invention results in the desired pretilt being achieved particularly quickly and in significantly shortened times in production of the display.

The prior art, such as, for example, U.S. Pat. No. 7,440,160 (WO 2004/046805 A1) and the documents cited therein, describes LC media for LC display elements which operate in the liquid-crystalline blue phase (blue phase for short). WO 2005/080529 A1 describes polymer-stabilised blue phases comprising mono- and multireactive monomers. U.S. 2009/0267025 A1 (WO 2006/063662 A1), U.S. 2009/051855 A1, U.S. 2009/0059132 A1, U.S. 2009/0059157 A1 and WO 2008/061606 A1 describe the polymer stabilisation of blue phases comprising liquid-crystalline reactive components (also known as reactive mesogens, "RMs" for short). In the publications mentioned above, however, preference is given to the use of RMs containing phenyl radicals either linked directly or via ester groups, such as, for example, the following two RMs:

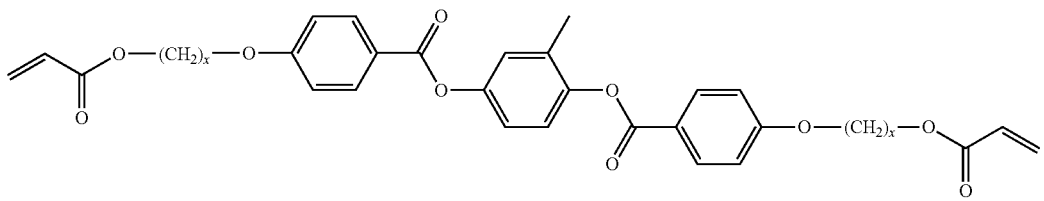

in which x denotes either 3 or 6.

However, the use of reactive components, which preferably consist of polymerisable compounds according to the invention, for polymer-stabilised blue phases or in PSA displays is neither described in nor obvious from the prior art.

U.S. Pat. No. 7,070,838 describes polymerisable compounds containing a 2-di- or -trifluoromethyl-1,4-phenyl ring, and the use thereof in polymerisable mixtures, LC polymers and LC displays having a cholesteric phase and in optical films. Specific compounds of a formula 1a-2-19 having the following structure are also disclosed therein:

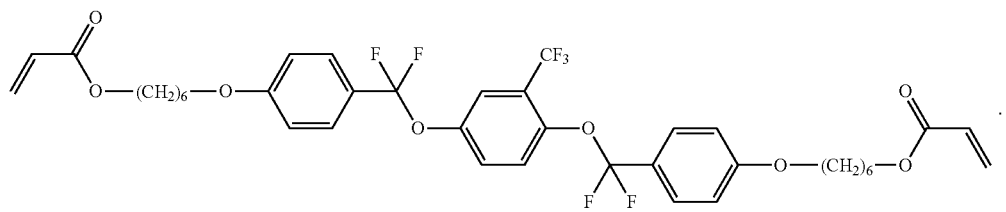

However, no properties of this compound on use in an LC display are disclosed. In addition, the use of compounds of this type for the stabilisation of blue phases or in PSA displays is neither described in nor obvious from U.S. Pat. No. 7,070,838.

JP 2005-015473 A discloses polymerisable compounds containing unsaturated spacer groups (alkynylene or alkenylene). Specific compounds of the formulae 1-13-77 to 1-13-84, 1-13-134, 1-13-135, 1-56-9, 1-56-10, 1-56-23, 1-56-24, which contain phenyl rings linked via $CF_2O$ bridges, and the use thereof for the production of optically anisotropic films and in ferroelectric LC media are also disclosed therein. Specific compounds, for example having the following structures, are also disclosed therein:

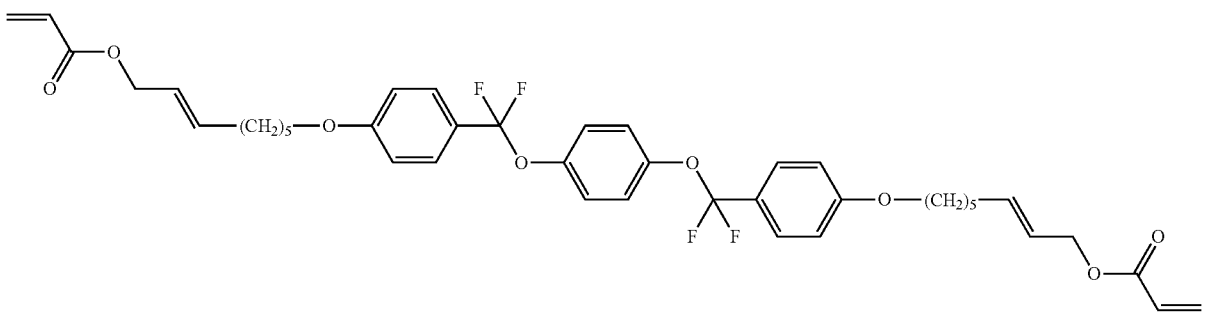

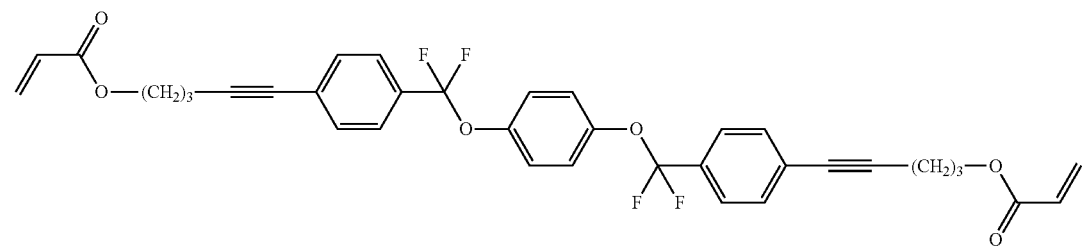

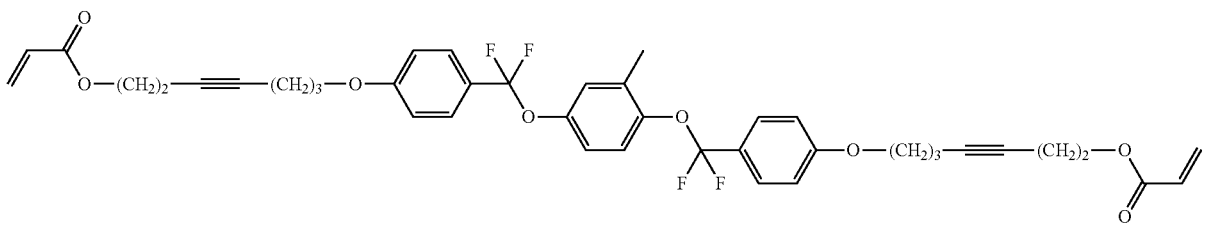

However, the use of compounds of this type for the stabilisation of blue phases or in PSA displays is neither described in nor obvious from JP 2005-015473A.

The invention relates to the use of compounds of the formula I $$P^a\text{-}(Sp^a)_{s1}\text{-}A^2\text{-}Q^1\text{-}A^1\text{-}Q^2\text{-}A^3\text{-}(Sp^b)_{s2}\text{-}P^b \qquad I$$

in which the individual radicals have the following meanings:

$P^a$, $P^b$ each, independently of one another, denote a polymerisable group, $Sp^a$, $Sp^b$ each, independently of one another, denote a spacer group, s1, s2 each, independently of one another, denote 0 or 1, $Q^1$, $Q^2$ each, independently of one another, denote —CF$_2$O— or —OCF$_2$—, $A^1$, $A^2$, $A^3$ each, independently of one another, denote a radical selected from the following groups:
  a) the group consisting of trans-1,4-cyclohexylene, 1,4-cyclohexenylene and 1,4'-bicyclohexylene, in which, in addition, one or more non-adjacent CH$_2$ groups may be replaced by —O— and/or —S— and in which, in addition, one or more H atoms may be replaced by F,
  b) the group consisting of 1,4-phenylene and 1,3-phenylene, in which, in addition, one or two CH groups may be replaced by N and in which, in addition, one or more H atoms may be replaced by L,
  c) the group consisting of tetrahydropyran-2,5-diyl, 1,3-dioxane-2,5-diyl, tetrahydrofuran-2,5-diyl, cyclobut-1,3-diyl, piperidine-1,4-diyl, thiophene-2,5-diyl and selenophene-2,5-diyl, each of which may, in addition, be mono- or polysubstituted by L,
  d) the group consisting of saturated, partially unsaturated or fully unsaturated, and optionally substituted, polycyclic radicals having 5 to 20 cyclic C atoms, one or more of which may also be replaced by heteroatoms, preferably selected from the group consisting of bicyclo[1.1.1]pentane-1,3-diyl, bicyclo[2.2.2]octane-1,4-diyl, spiro[3.3]heptane-2,6-diyl,

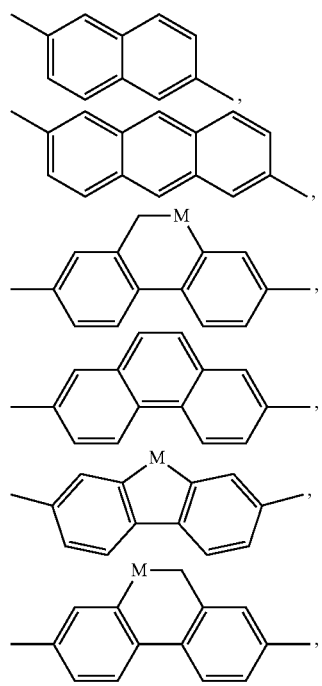

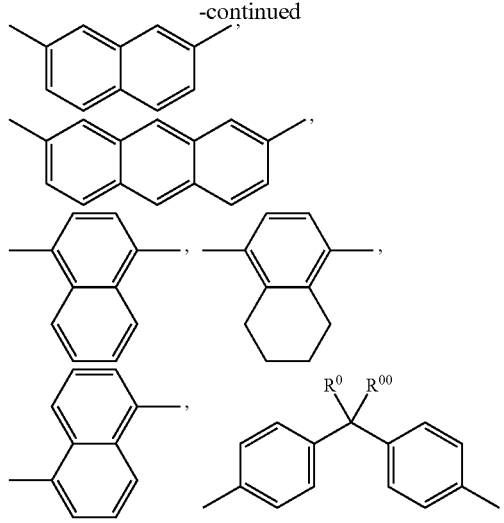

where, in addition, one or more H atoms in these radicals may be replaced by L, and/or one or more double bonds may be replaced by single bonds, and/or one or more CH groups may be replaced by N, L on each occurrence, identically or differently, denotes F, Cl, CN, SCN, SF$_5$ or straight-chain or branched, in each case optionally fluorinated alkyl, alkoxy, alkylcarbonyl, alkoxycarbonyl, alkylcarbonyloxy or alkoxycarbonyloxy having 1 to 12 C atoms, $R^0$, $R^{00}$ each, independently of one another, denote H, F or straight-chain or branched alkyl having 1 to 12 C atoms, in which, in addition, one or more H atoms may be replaced by F, M denotes —O—, —S—, —CH$_2$—, —CHY$^1$— or —CY$^1$Y$^2$—, $Y^1$ and $Y^2$ each, independently of one another, have one of the meanings indicated above for $R^0$, or denote OCF$_3$, Cl or CN, and preferably denote H, F, Cl, CN, OCF$_3$ or CF$_3$, wherein one of $Y^1$ and $Y^2$ may be OCF$_3$, or the use of a polymer obtainable by polymerisation of one or more compounds of the formula I, in LC displays having a blue phase or in LC displays of the PS or PSA type.

The invention furthermore relates to an LC medium comprising one or more compounds of the formula I and optionally additionally one or more polymerisable compounds.

The invention furthermore relates to an LC medium comprising one or more compounds of the formula I and one or more additional compounds, which may also be mesogenic, liquid-crystalline and/or polymerisable.

The invention furthermore relates to an LC medium comprising a polymer obtainable by polymerisation of one or more compounds of the formula I, and optionally comprising one or more additional compounds, which may also be mesogenic, liquid-crystalline and/or polymerisable.

The invention furthermore relates to an LC medium comprising
  a polymerisable component comprising one or more polymerisable compounds of the formula I, or the polymerised form of this polymerisable component, and
  a liquid-crystalline component, also referred to below as "LC host mixture", comprising one or more, preferably two or more, low-molecular-weight (i.e. monomeric and unpolymerisable) compounds as described above and below, which are preferably mesogenic or liquid-crystalline.

The invention furthermore relates to the use of LC media comprising one or more compounds of the formula I in LC displays having a blue phase or in LC displays of the PS or PSA type.

The invention furthermore relates to a process for the preparation of an LC medium as described above and below in which one or more low-molecular-weight liquid-crystalline compounds, or an LC host mixture as described above and below, are mixed with one or more compounds of the formula I and optionally with further liquid-crystalline compounds and/or additives.

The invention furthermore relates to the use of compounds of the formula I and LC media according to the invention comprising them in LC displays for stabilisation of the blue phase, in particular over the greatest possible temperature range.

The invention furthermore relates to the use of compounds of the formula I and LC media according to the invention comprising them in PS and PSA displays for the generation of a tilt angle in the LC medium by in-situ polymerisation of the compound(s) of the formula I in the PSA display, preferably with application of an electric or magnetic field.

The invention furthermore relates to an LC display containing one or more compounds of the formula I or an LC medium according to the invention, in particular a PS or PSA display, particularly preferably a display having a blue phase, a PSA-VA, PSA-OCB, PSA-IPS, PSA-FFS or PSA-TN display.

The invention furthermore relates to an LC display of the PS or PSA type containing an LC cell having two substrates and two electrodes, where at least one substrate is transparent to light and at least one substrate has one or two electrodes, and a layer, located between the substrates, of an LC medium comprising a polymerised component and a low-molecular-weight component, where the polymerised component is obtainable by polymerisation of one or more polymerisable compounds between the substrates of the LC cell in the LC medium, preferably with application of an electrical voltage to the electrodes, characterised in that at least one of the polymerisable compounds is selected from formula I.

The invention furthermore relates to a process for the production of an LC display as described above and below in which an LC medium comprising one or more low-molecular-weight liquid-crystalline compounds or an LC host mixture as described above and below and one or more polymerisable compounds, at least one of which is selected from formula I, is introduced into an LC cell having two substrates and two electrodes as described above and below, and the polymerisable compounds are polymerised, preferably with application of an electrical voltage to the electrodes.

The PS and PSA displays according to the invention have two electrodes, preferably in the form of transparent layers, which are applied to one or both of the substrates which form the LC cell. Either in each case one electrode is applied to each of the two substrates, as, for example, in PSA-VA, PSA-OCB or PSA-TN displays according to the invention, or both electrodes are applied to only one of the two substrates, while the other substrate has no electrode, as, for example, in PSA-IPS or PSA-FFS displays according to the invention.

The invention furthermore relates to novel compounds of the formula I, to processes for the preparation thereof, and to novel intermediates used in or obtained from these processes, in particular compounds of the formula I, and sub-formulae thereof as defined above and below, in which one or more of the radicals $A^1$, $A^2$ and $A^3$ are selected from the group d) as defined in formula I, consisting of optionally substituted, saturated or partially or fully unsaturated, polycyclic radicals having 5 to 20 cyclic C atoms, one or more of which may also be replaced by heteroatoms.

Particular preference is given to an LC medium, an LC display, a process or a use as described above and below in which the LC medium or the polymerisable or polymerised component present therein does not comprise any compounds of the following formula:

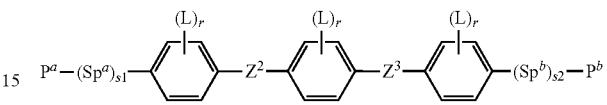

M in which $P^a$, $P^b$, $Sp^a$, $Sp^b$, s1, s2 and L have the meanings indicated above and below, r denotes 0, 1, 2, 3 or 4, and $Z^2$ and $Z^3$ each, independently of one another, denote —COO— or —OCO—.

The following meanings apply above and below:

The term "cyclic C atom" denotes a C atom which forms a carbo- or heterocyclic radical with other C atoms and/or heteroatoms.

The terms "tilt" and "tilt angle" relate to a tilted alignment of the LC molecules of an LC medium relative to the surfaces of the cell in an LC display (here preferably a PS or PSA display). The tilt angle here denotes the average angle (<90°) between the longitudinal molecular axes of the LC molecules (LC director) and the surface of the plane-parallel outer plates which form the LC cell. A low value for the tilt angle (i.e. a large deviation from the 90° angle) corresponds to a large tilt here. A suitable method for measurement of the tilt angle is given in the examples. Unless indicated otherwise, tilt angle values disclosed above and below relate to this measurement method.

The term "mesogenic group" is known to the person skilled in the art and is described in the literature, and denotes a group which, due to the anisotropy of its attracting and repelling interactions, essentially contributes to causing a liquid-crystal (LC) phase in low-molecular-weight or polymeric substances. Compounds containing mesogenic groups (mesogenic compounds) do not necessarily have to have an LC phase themselves. It is also possible for mesogenic compounds to exhibit LC phase behaviour only after mixing with other compounds and/or after polymerisation. Typical mesogenic groups are, for example, rigid rod- or disc-shaped units. An overview of the terms and definitions used in connection with mesogenic or LC compounds is given in Pure Appl. Chem. 73 (5), 888 (2001) and C. Tschierske, G. Pelzl, S. Diele, Angew. Chem. 2004, 116, 6340-6368.

The term "spacer group" or "spacer", also referred to as "Sp" above and below, is known to the person skilled in the art and is described in the literature, see, for example, Pure Appl. Chem. 73 (5), 888 (2001) and C. Tschierske, G. Pelzl, S. Diele, Angew. Chem. 2004, 116, 6340-6368. Unless indicated otherwise, the term "spacer group" or "spacer" above and below denotes a flexible group which connects the mesogenic group and the polymerisable group(s) to one another in a polymerisable mesogenic compound.

The term "reactive mesogen" or "RM" denotes a compound containing one mesogenic group and one or more functional groups which are suitable for polymerisation (also referred to as polymerisable group or group P).

The terms "low-molecular-weight compound" and "unpolymerisable compound" denote compounds, usually monomeric, which contain no functional group which is suitable for polymerisation under the usual conditions known to the person skilled in the art, in particular under the conditions used for the polymerisation of RMs.

"Halogen" denotes F, Cl, Br or I.

Definitions such as "alkyl, alkoxy, alkylcarbonyl, alkoxycarbonyl, alkylcarbonyloxy or alkoxycarbonyloxy having 1 to 12 C atoms" etc., mean that the radicals containing a carbonyl group (CO) and the unsaturated radicals, such as alkenyl and alkynyl, have at least two C atoms, and the branched radicals have at least three C atoms.

The polymerisable group $P^{a,b}$ is a group which is suitable for a polymerisation reaction, such as, for example, free-radical or ionic chain polymerisation, polyaddition or polycondensation, or for a polymer-analogous reaction, for example addition or condensation onto a main polymer chain. Particular preference is given to groups for chain polymerisation, in particular those containing a C=C double bond or —C≡C— triple bond, and groups which are suitable for polymerisation with ring opening, such as, for example, oxetane or epoxide groups.

Preferred groups $P^{a,b}$ are selected from the group consisting of $CH_2=CW^1—CO—O—$, $CH_2=CW^1—CO—$,

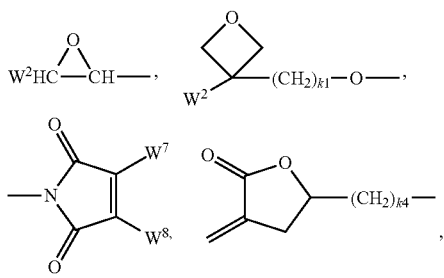

$CH_2=CW^2—(O)_{k3}—$, $CW^1=CH—CO—(O)_{k3}—$, $CW^1=CH—CO—NH—$, $CH_2=CW^1—CO—NH—$, $CH_3—CH=CH—O—$, $(CH_2=CH)_2CH—OCO—$, $(CH_2=CH—CH_2)_2CH—OCO—$, $(CH_2=CH)_2CH—O—$, $(CH_2=CH—CH_2)_2N—$, $(CH_2=CH—CH_2)_2N—CO—$, $HO—CW^2W^3—$, $HS—CW^2W^3—$, $HW^2N—$, $HO—CW^2W^3—NH—$, $CH_2=CW^1—CO—NH—$, $CH_2=CH—(COO)_{k1}$-Phe-$(O)_{k2}—$, $CH_2=CH—(CO)_{k1}$-Phe-$(O)_{k2}—$, Phe-CH=CH—, HOOC—, OCN— and $W^4W^5W^6Si—$, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, which is optionally substituted by one or more radicals L as defined above which are other than P-Sp-, $k_1$, $k_2$ and $k_3$ each, independently of one another, denote 0 or 1, $k_3$ preferably denotes 1, and $k_4$ denotes an integer from 1 to 10.

Particularly preferred groups $P^{a,b}$ are selected from the group consisting of $CH_2=CW^1—CO—O—$, $CH_2=CW^1—CO—$,

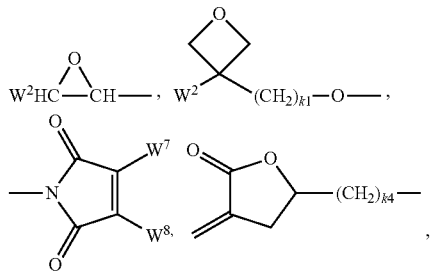

$CH_2=CW^2—O—$, $CW^1=CH—CO—(O)_{k3}—$, $CW^1=CH—CO—NH—$, $CH_2=CW^1—CO—NH—$, $(CH_2=CH)_2CH—OCO—$, $(CH_2=CH—CH_2)_2CH—OCO—$, $(CH_2=CH)_2CH—O—$, $(CH_2=CH—CH_2)_2N—$, $(CH_2=CH—CH_2)_2N—CO—$, $CH_2=CW^1—CO—NH—$, $CH_2=CH—(COO)_{k1}$-Phe-$(O)_{k2}—$, $CH_2=CH—(CO)_{k1}$-Phe-$(O)_{k2}—$, Phe-CH=CH— and $W^4W^5W^6Si—$, in which $W^1$ denotes H, F, Cl, CN, $CF_3$, phenyl or alkyl having 1 to 5 C atoms, in particular H, F, Cl or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, $k_1$, $k_2$ and $k_3$ each, independently of one another, denote 0 or 1, $k_3$ preferably denotes 1, and $k_4$ denotes an integer from 1 to 10.

Very particularly preferred groups $P^{a,b}$ are selected from the group consisting of $CH_2=CW^1—CO—O—$, in particular $CH_2=CH—CO—O—$, $CH_2=C(CH_3)—CO—O—$ and $CH_2=CF—CO—O—$, furthermore $CH_2=CH—O—$, $(CH_2=CH)_2CH—O—CO—$, $(CH_2=CH)_2CH—O—$,

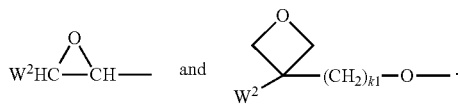

Further very particularly preferred groups $P^{a,b}$ are selected from the group consisting of vinyloxy, acrylate, methacrylate, fluoroacrylate, chloroacrylate, oxetane and epoxide groups, and particularly preferably denote an acrylate or methacrylate group.

Preferred spacer groups $Sp^{a,b}$ are selected from the formula Sp"-X", so that the radical $P^{a/b}$-$Sp^{a/b}$- conforms to the formula $P^{a/b}$-Sp"-X"—, where Sp" denotes alkylene having 1 to 20, preferably 1 to 12, C atoms, which is optionally mono- or polysubstituted by F, Cl, Br, I or CN, and in which, in addition, one or more non-adjacent $CH_2$ groups may each be replaced, independently of one another, by —O—, —S—, —NH—, —N($R^0$)—, —Si($R^{00}R^{000}$)—, —CO—, —CO—O—, —O—CO—, —O—CO—O—, —S—CO—, —CO—S—, —N($R^{00}$)—CO—O—, —O—CO—N($R^{00}$)—, —N($R^{00}$)—CO—N($R^{00}$)—, —CH=CH— or —C≡C— in such a way that O and/or S atoms are not linked directly to one another, X" denotes —O—, —S—, —CO—, —CO—O—, —O—CO—, —O—CO—O—, —CO—N($R^{00}$)—, —N($R^{00}$)—CO—, —N($R^{00}$)—CO—N($R^{00}$)—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR⁰—, —CY²=CY³—, —C≡C—, —CH=CH—CO—O—, —O—CO—CH=CH— or a single bond, R⁰⁰ and R⁰⁰⁰ each, independently of one another, denote H or alkyl having 1 to 12 C atoms, and Y² and Y³ each, independently of one another, denote H, F, Cl or CN.

X' is preferably —O—, —S—, —CO—, —COO—, —OCO—, —O—COO—, —CO—NR⁰—, —NR⁰—CO—, —NR⁰—CO—NR⁰— or a single bond.

Typical spacer groups Sp" are, for example, —(CH₂)$_{p1}$—, —(CH₂CH₂O)$_{q1}$—CH₂CH₂—, —CH₂CH₂—S—CH₂CH₂—, —CH₂CH₂—NH—CH₂CH₂— or —(SiR⁰⁰R⁰⁰⁰—O)$_{p1}$—, in which p1 is an integer from 1 to 12, q1 is an integer from 1 to 3, and R⁰⁰ and R⁰⁰⁰ have the meanings indicated above.

Particularly preferred groups -Sp"-X"— are —(CH₂)$_{p1}$—, —(CH₂)$_{p1}$—O—, —(CH₂)$_{p1}$—O—CO—, —(CH₂)$_{p1}$—O—CO—O—, in which p1 and q1 have the meanings indicated above.

Particularly preferred groups Sp" are, for example, in each case straight-chain ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene and butenylene.

In a further preferred embodiment of the invention, P$^a$ and/or P$^b$ in formula I denote a radical containing two or more polymerisable groups (multifunctional polymerisable radicals). Suitable radicals of this type and polymerisable compounds containing them and the preparation thereof are described, for example, in U.S. Pat. No. 7,060,200 B1 or US 2006/0172090 A1.

Particular preference is given to multifunctional polymerisable radicals selected from the following formulae:

| | |
|---|---|
| —X-alkyl-CHP¹—CH₂—CH₂P² | I*a |
| —X-alkyl-C(CH₂P¹)(CH₂P²)—CH₂P³ | I*b |
| —X-alkyl-CHP¹CHP²—CH₂P³ | I*c |
| —X-alkyl-C(CH₂P¹)(CH₂P²)—C$_{aa}$H$_{2aa+1}$ | I*d |
| —X-alkyl-CHP¹—CH₂P² | I*e |
| —X-alkyl-CHP¹P² | I*f |
| —X-alkyl-CP¹P²—C$_{aa}$H$_{2aa+1}$ | I*g |
| —X-alkyl-C(CH₂P¹)(CH₂P²)—CH₂OCH₂—C(CH₂P³)(CH₂P⁴)CH₂P⁵ | I*h |
| —X-alkyl-CH((CH₂)$_{aa}$P¹)((CH₂)$_{bb}$P²) | I*i |
| —X-alkyl-CHP¹CHP²—C$_{aa}$H$_{2aa+1}$ | I*k |
| —X'-alkyl-C(CH₃)(CH₂P¹)(CH₂P²) | I*m | in which alkyl denotes a single bond or straight-chain or branched alkylene having 1 to 12 C atoms, in which one or more non-adjacent CH₂ groups may each be replaced, independently of one another, by —C(R⁰⁰)=C(R⁰⁰⁰)—, —C≡C—, —N(R⁰⁰)—, —O—, —S—, —CO—, —CO—O—, —O—CO—, —O—CO—O— in such a way that O and/or S atoms are not linked directly to one another, and in which, in addition, one or more H atoms may be replaced by F, Cl or ON, where R⁰⁰ and R⁰⁰⁰ have the meanings indicated above, aa and bb each, independently of one another, denote 0, 1, 2, 3, 4, 5 or 6, X has one of the meanings indicated for X', and P$^{1-5}$ each, independently of one another, have one of the meanings indicated for P$^a$.

A¹ in formula I preferably denotes a radical selected from the group consisting of the following formulae:

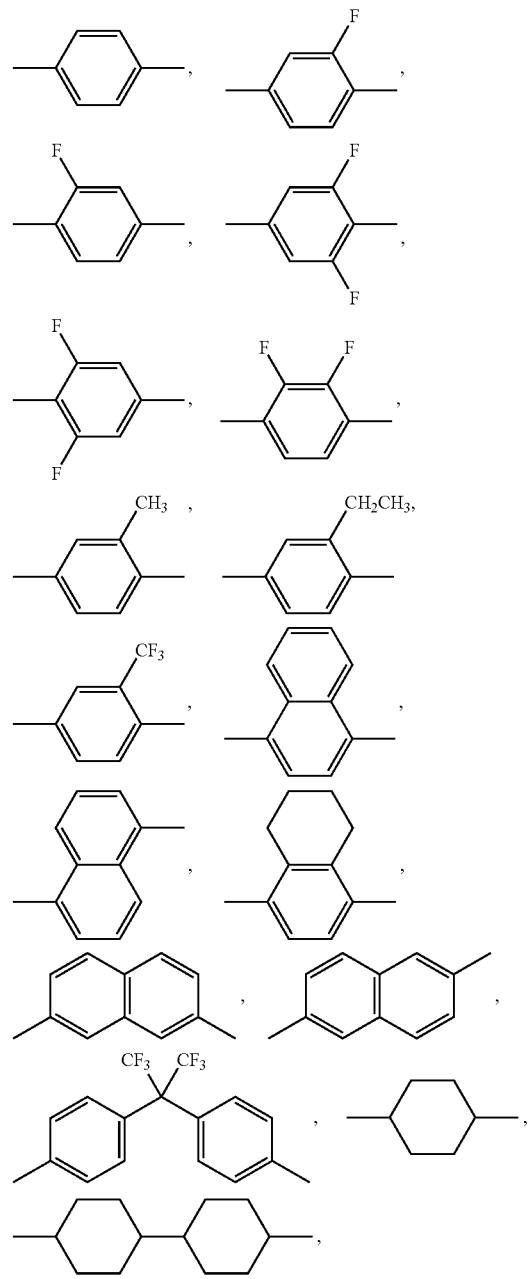

in which the individual rings may also additionally be mono- or polysubstituted by L as described above and below.

A¹ in formula I particularly preferably denotes a radical selected from the group consisting of the following formulae:

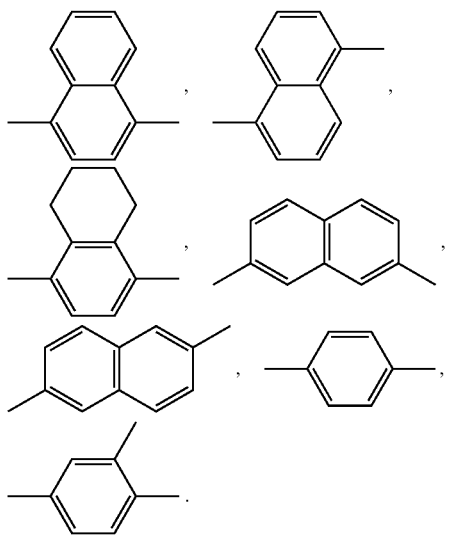

$A^2$ and $A^3$ in formula I preferably each, independently of one another, denote a radical selected from the group consisting of the following formulae:

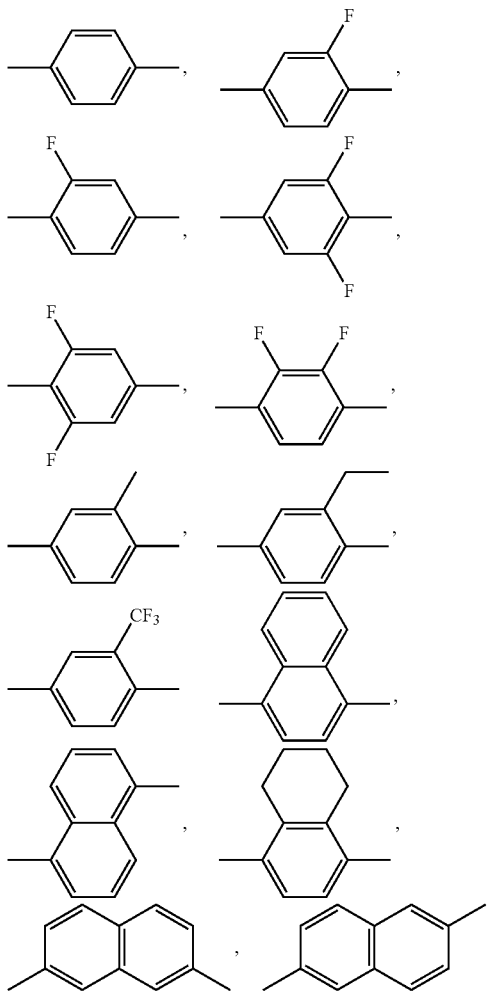

in which the individual rings may also additionally be mono- or polysubstituted by L as described above and below.

$A^2$ and $A^3$ in formula I particularly preferably each, independently of one another, denote a radical selected from the group consisting of the following formulae:

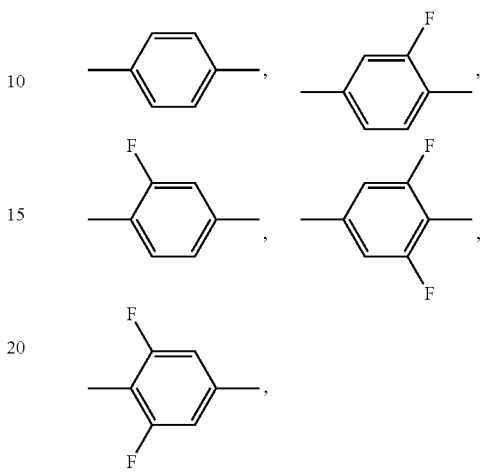

very particularly preferably

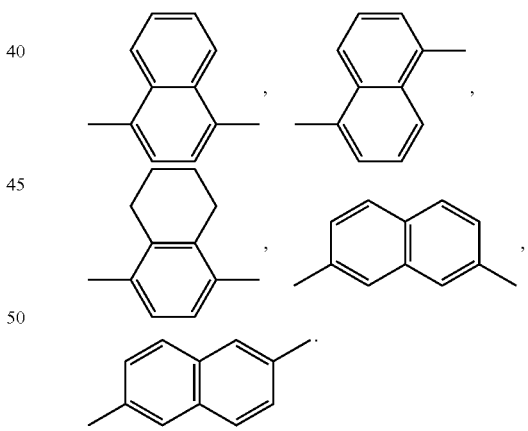

$A^2$ and $A^3$ in formula I furthermore preferably each, independently of one another, denote a radical selected from the group consisting of the following formulae:

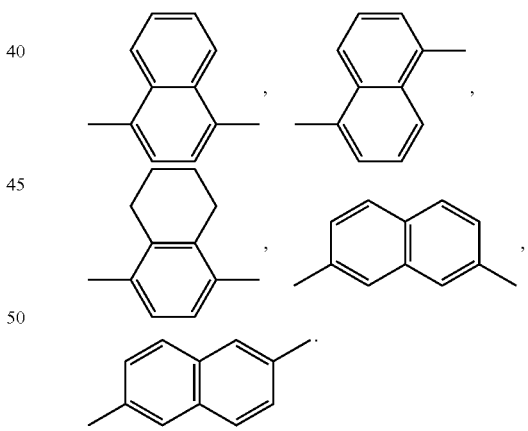

Further particularly preferred compounds of the formula I and sub-formulae thereof indicated above and below are those in which $Q^1$-$CF_2O$— and $Q^2$ denote —$OCF_2$—,
$Q^1$-$OCF_2$— and $Q^2$ denote —$CF_2O$—,
$Q^1$ and $Q^2$ denote —$CF_2O$—,
$Q^1$ and $Q^2$ denote —$OCF_2$—,
s1 and s2 each denote 0,
s1 and s2 each denote 1,
s1 denotes 1 and s2 denotes 0 or s1 denotes 0 and s2 denotes 1,
$A^2$ and $A^3$ have the same meaning.

Very particularly preferred compounds of the formula I and sub-=formulae thereof indicated above and below are those in which $Q^1$ denotes —$CF_2O$— and $Q^2$ denotes —$OCF_2$—.
Very particularly preferred compounds of the formula I are selected from the group consisting of the following formulae:
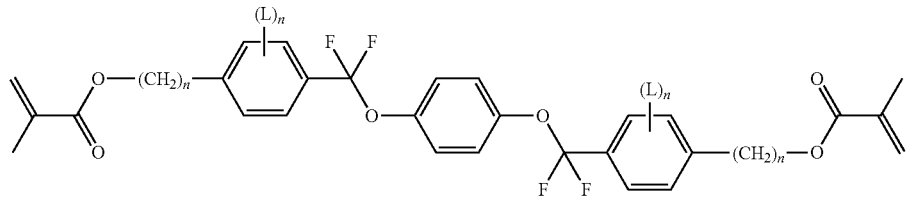
I1
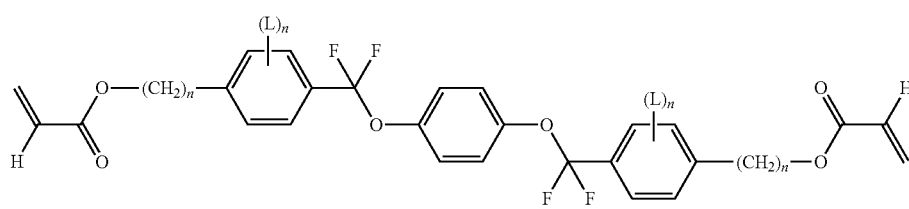
I2
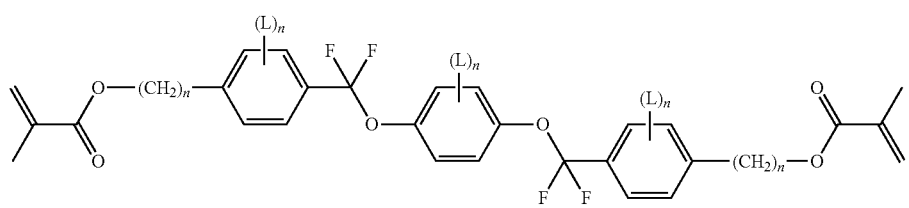
I3
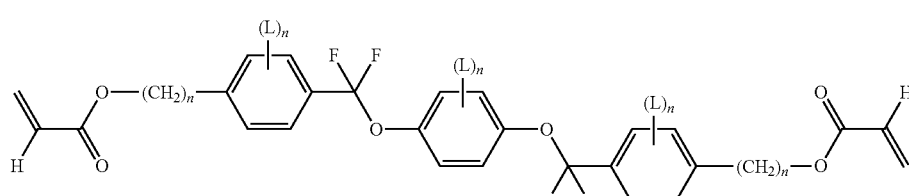
I4
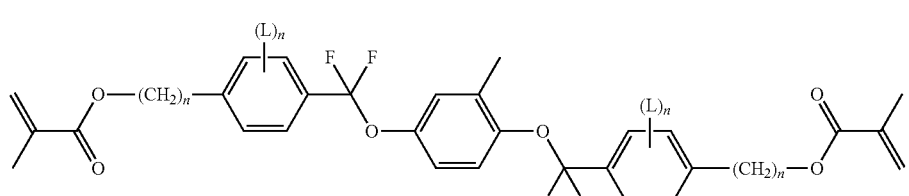
I5
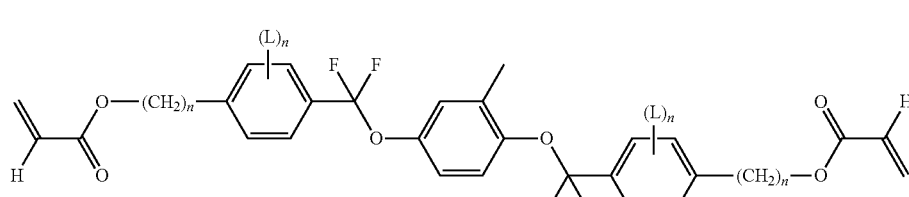
I6
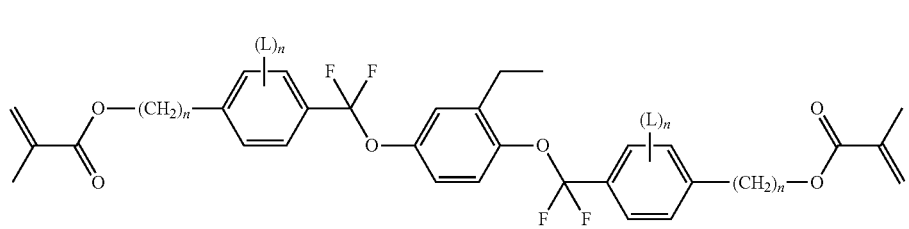
I7

-continued
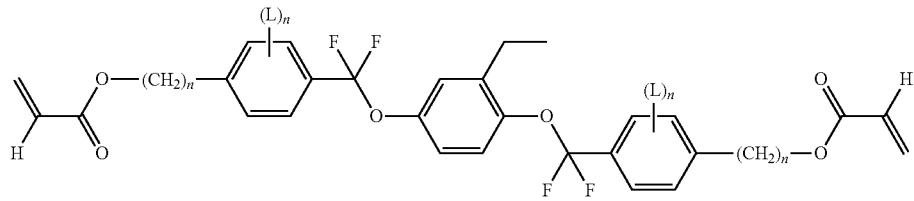
I8
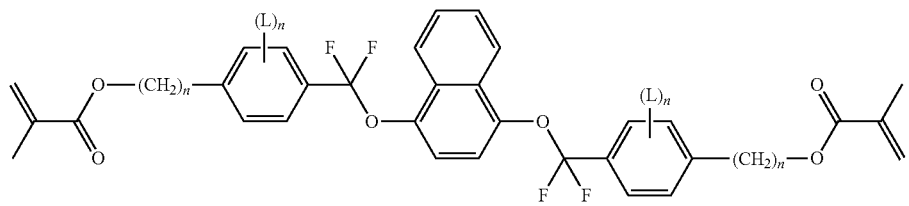
I9
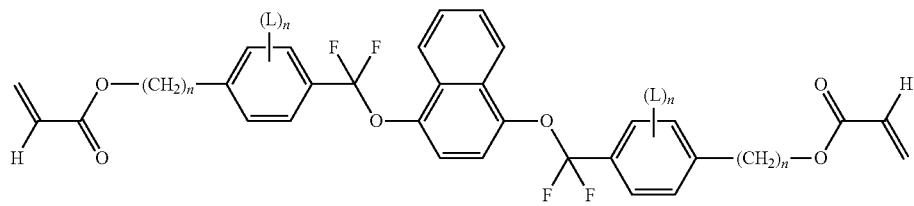
I10
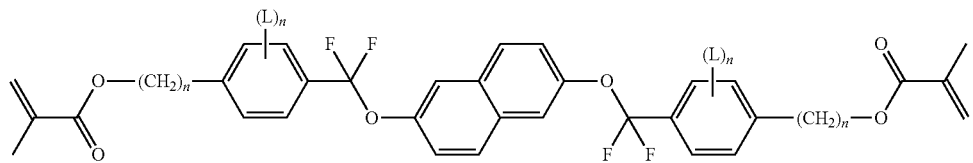
I11
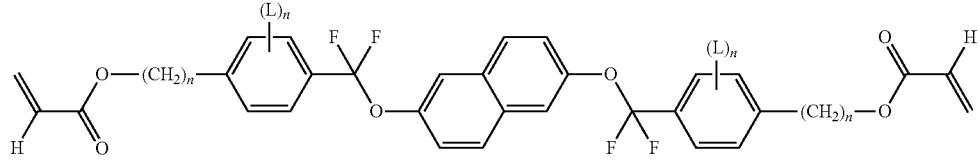
I12
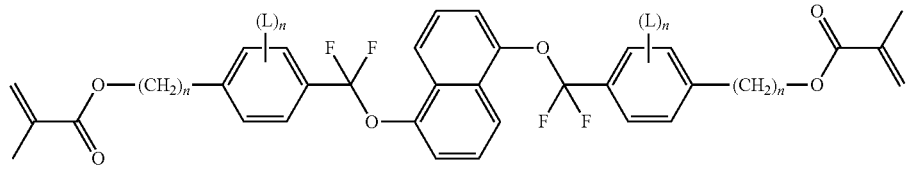
I13
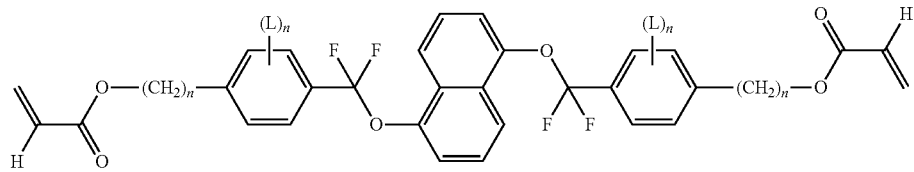
I14
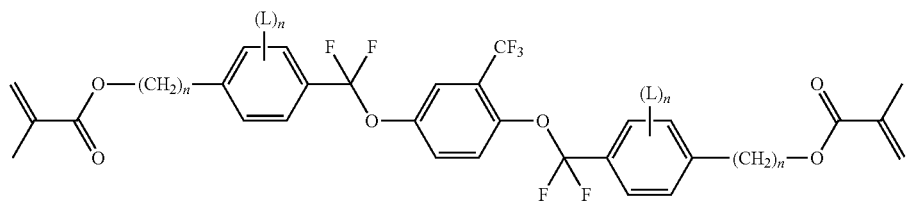
I15

-continued
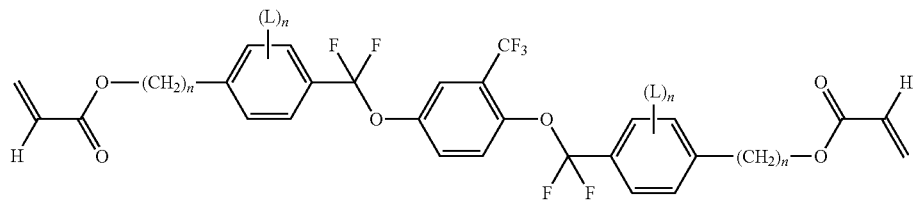
I16
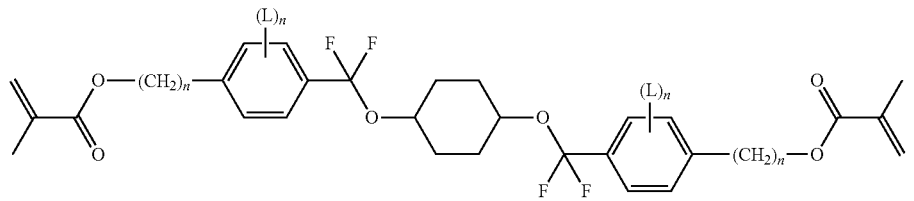
I17
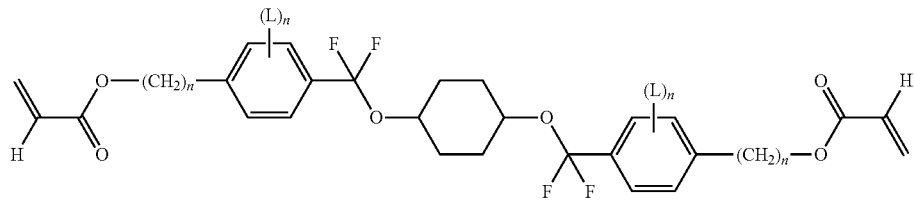
I18
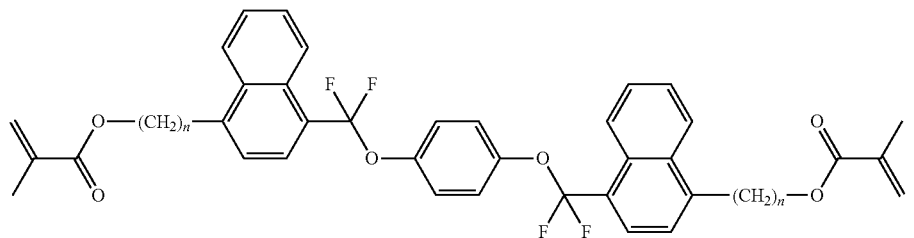
I19
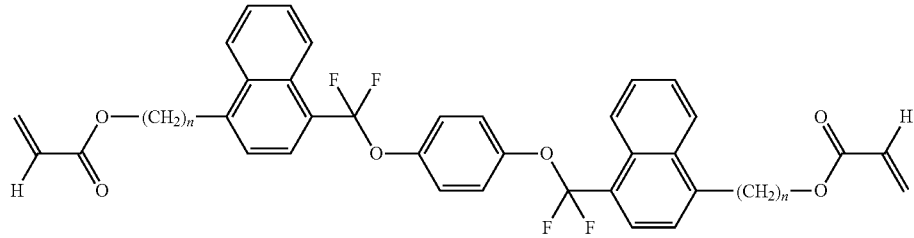
I20
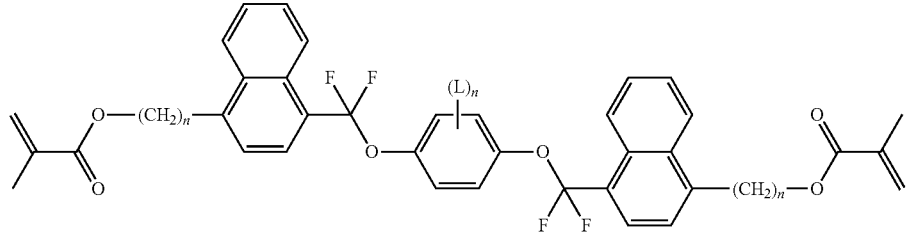
I21
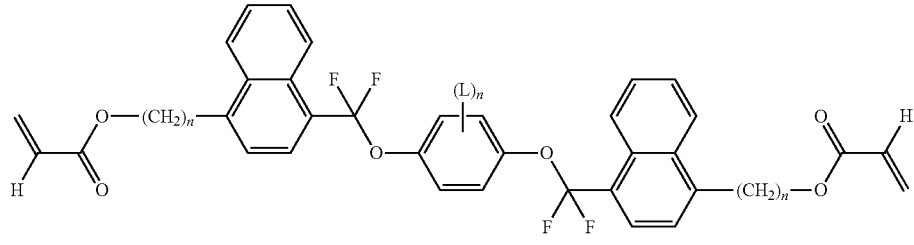
I22

-continued
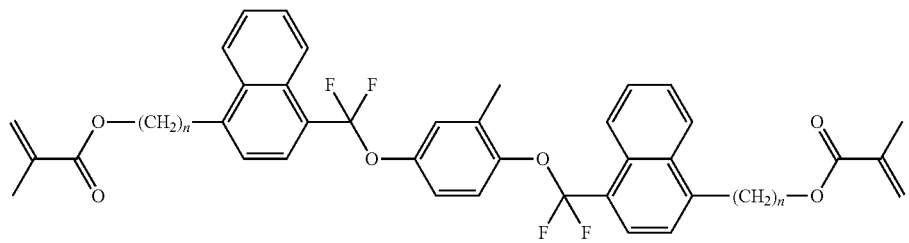
I23
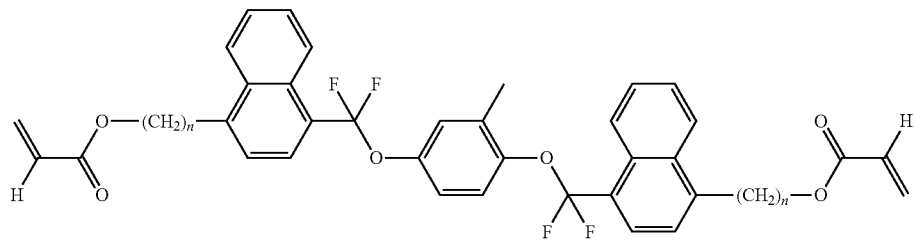
I24
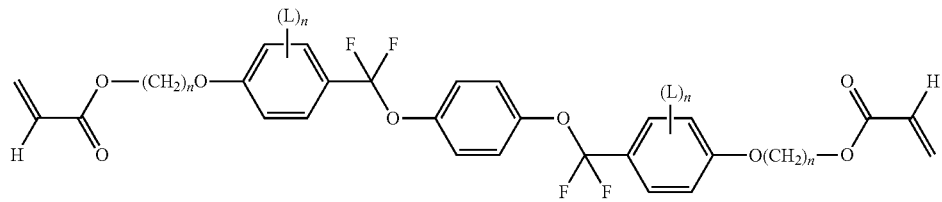
I25
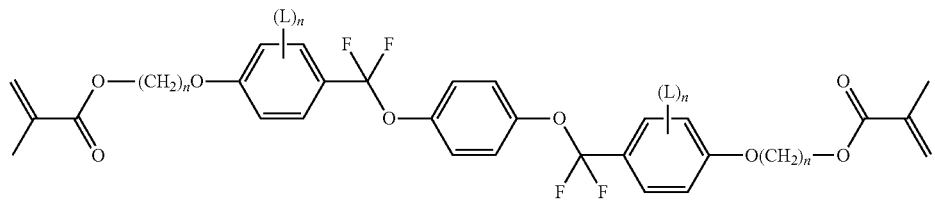
I26
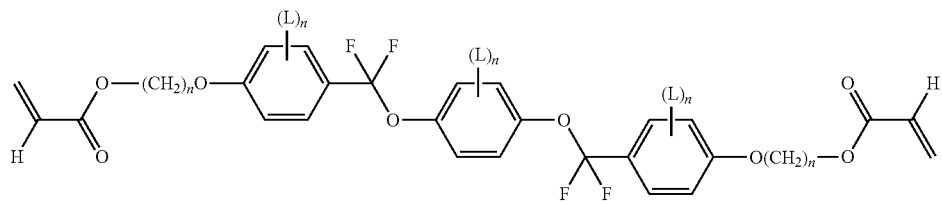
I27
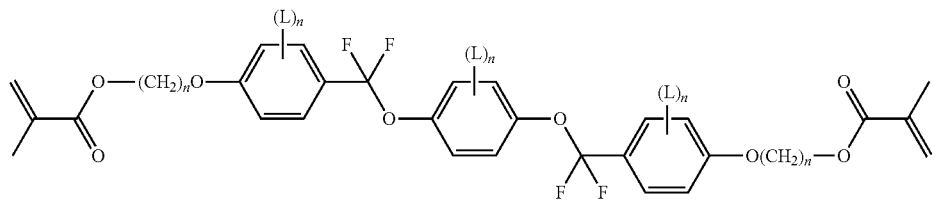
I28
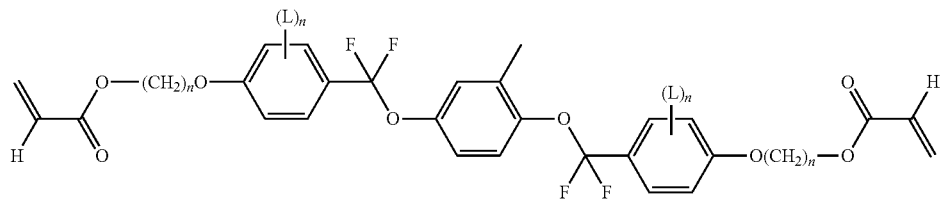
I29

-continued
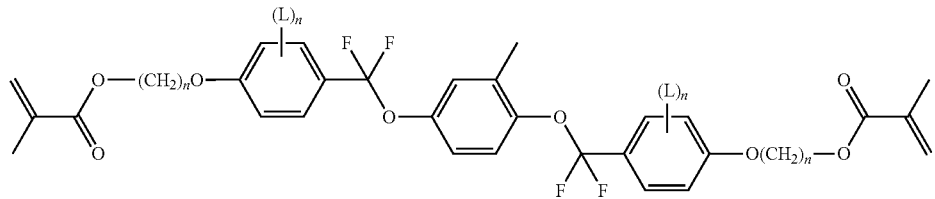
I30
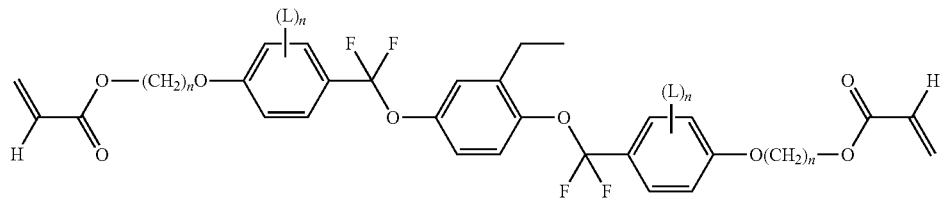
I31
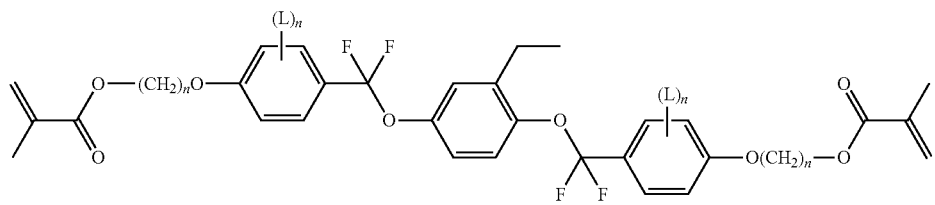
I32
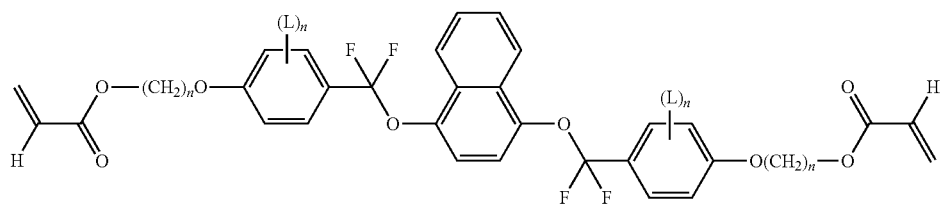
I33
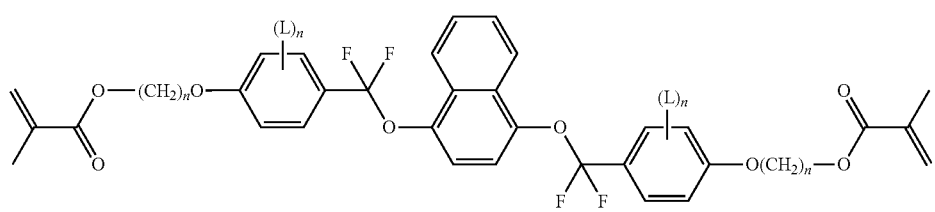
I34
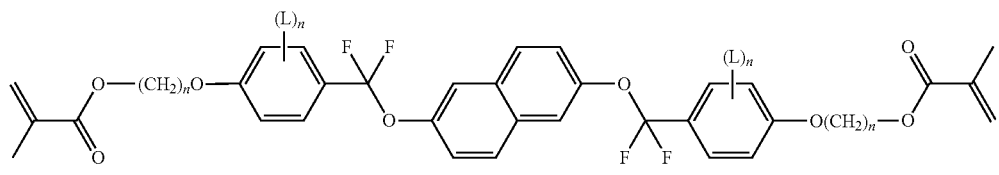
I35
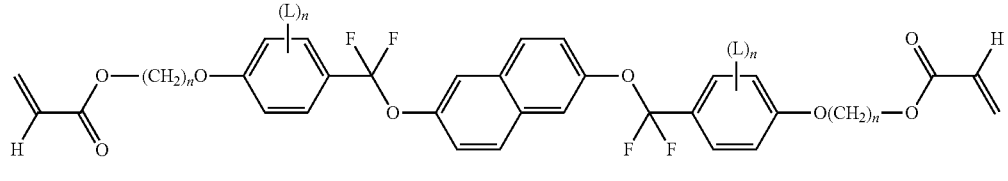
I36
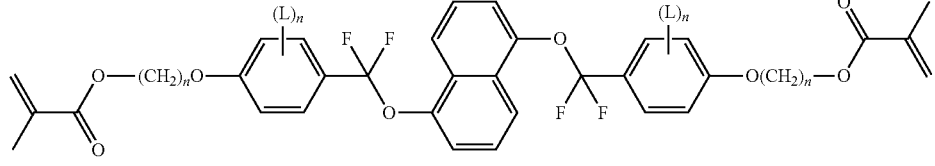
I37

I38
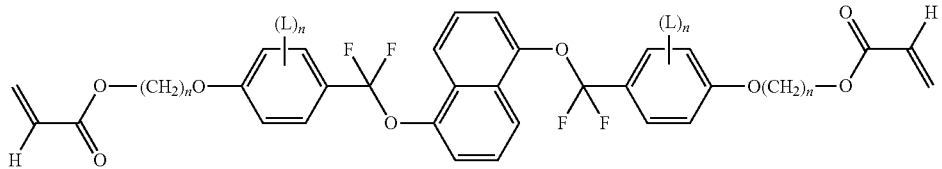
I39
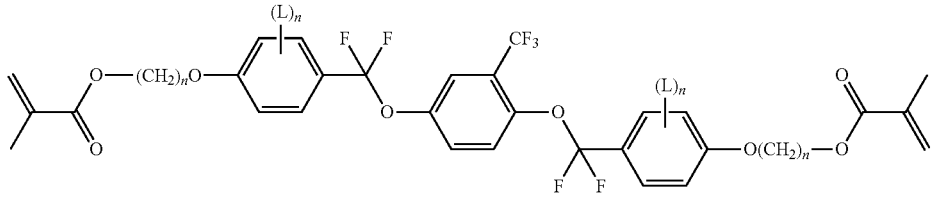
I40
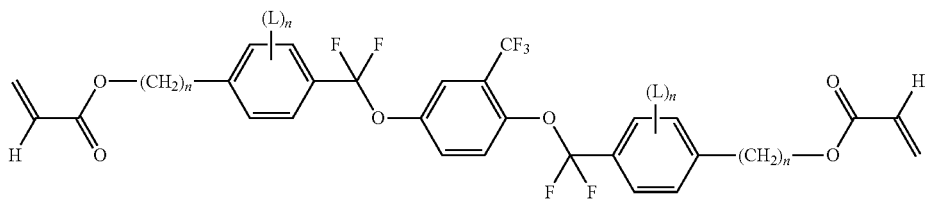
I41
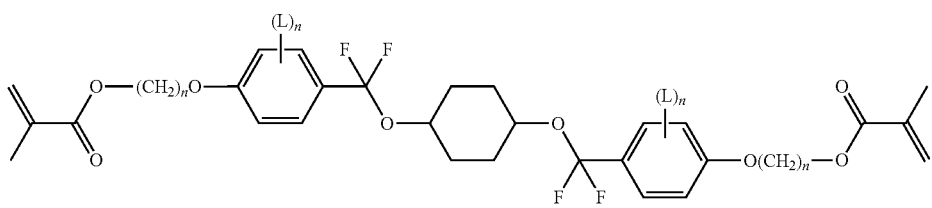
I42
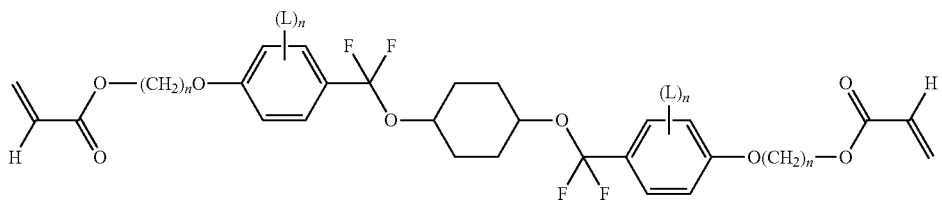
I43
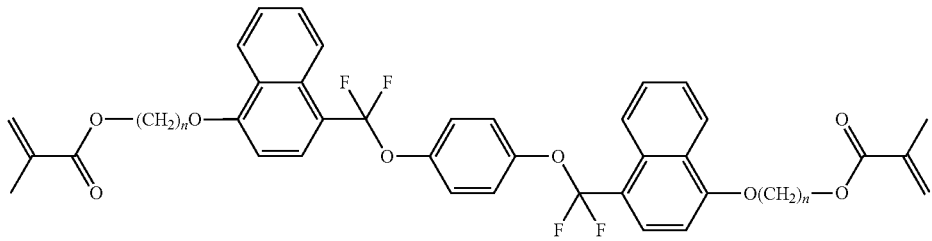
I44
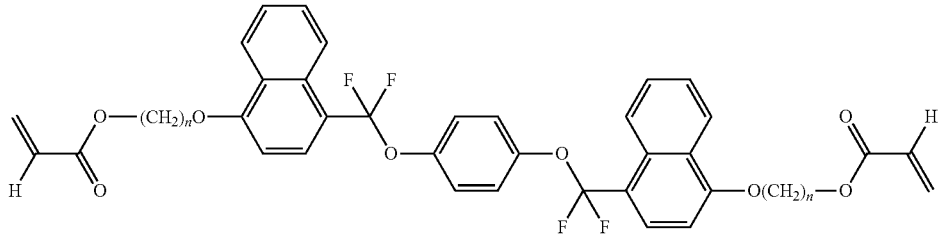

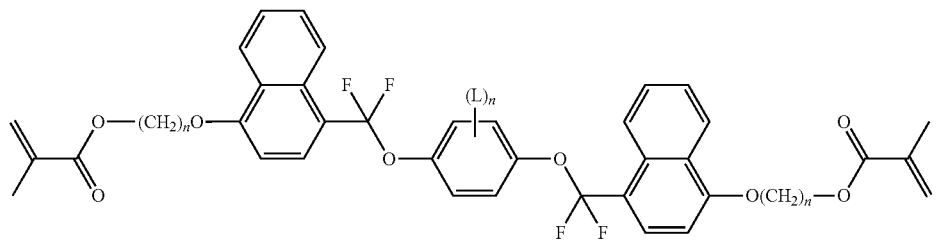
I45
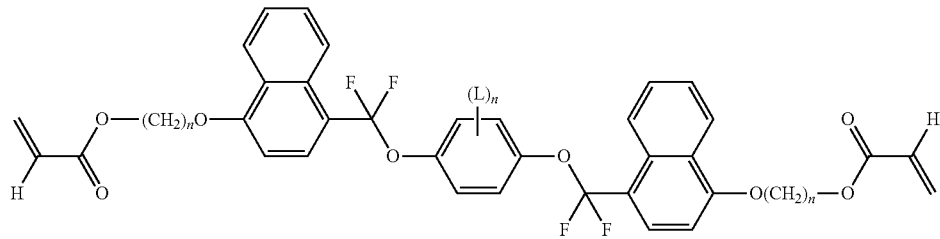
I46
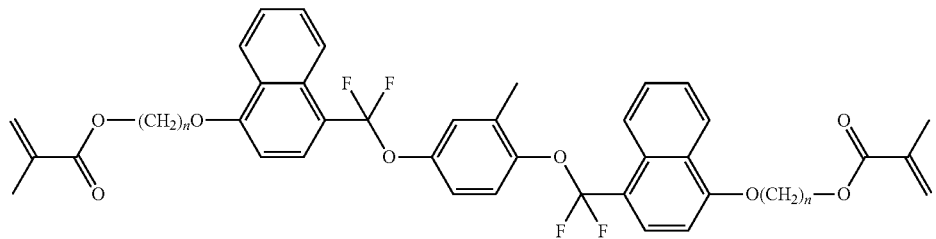
I47
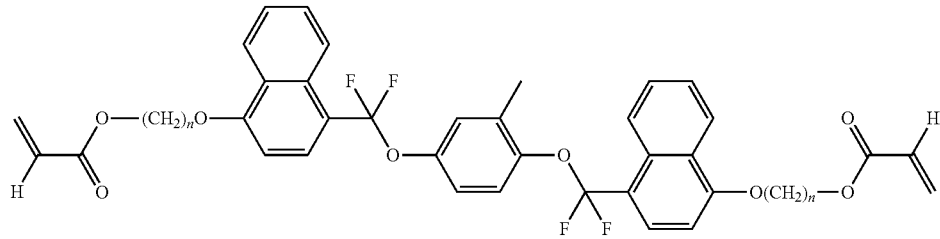
I48
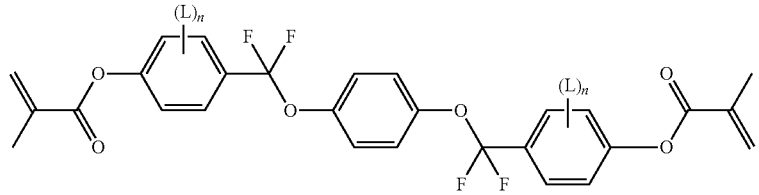
I49
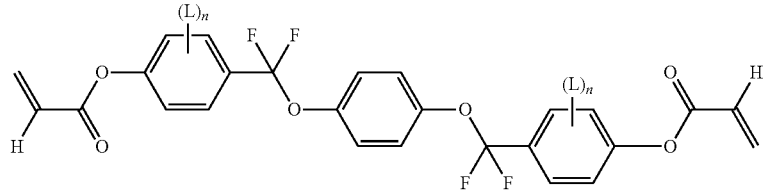
I50
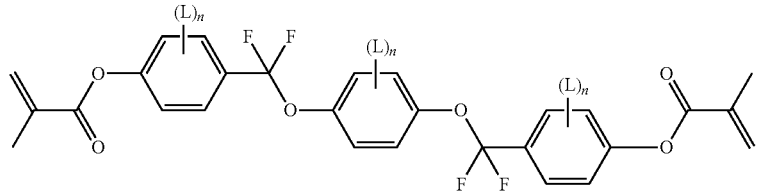
I51

-continued
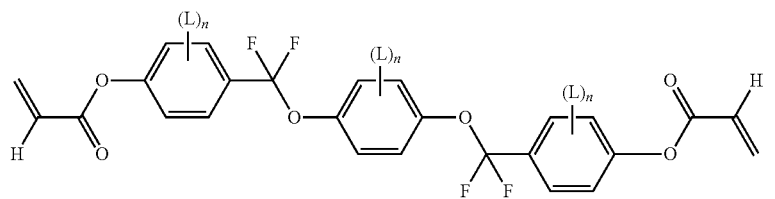
I52
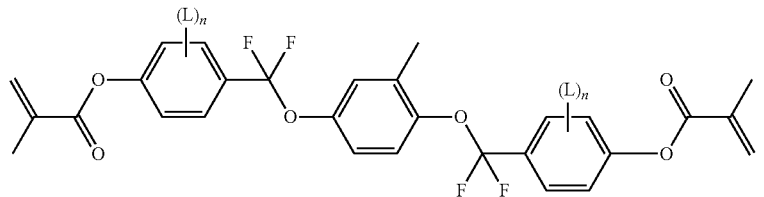
I53
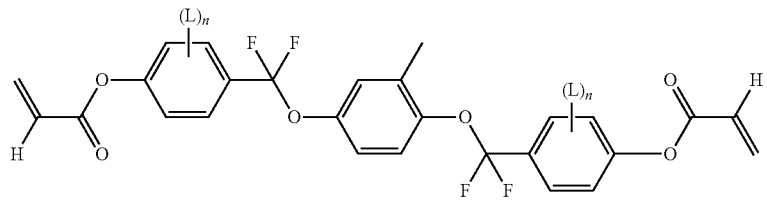
I54
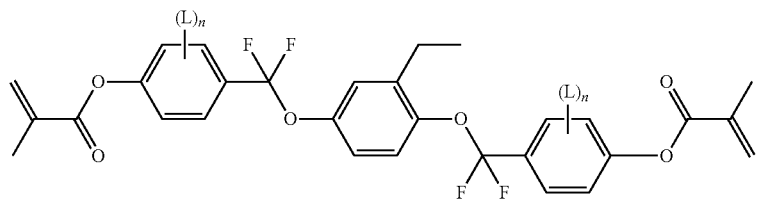
I55
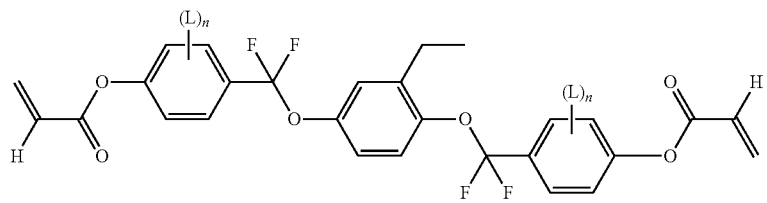
I56
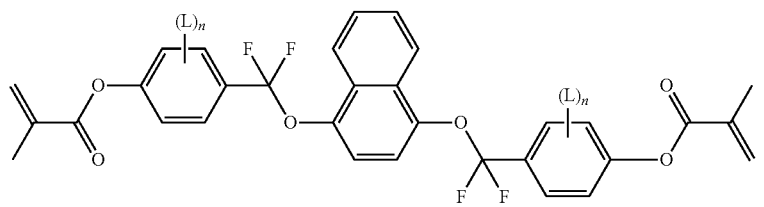
I57
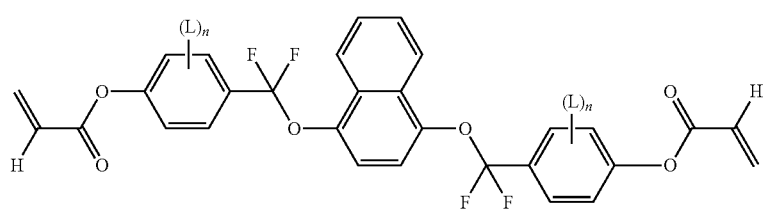
I58
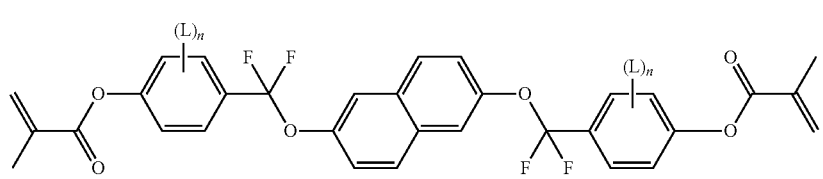
I59

-continued
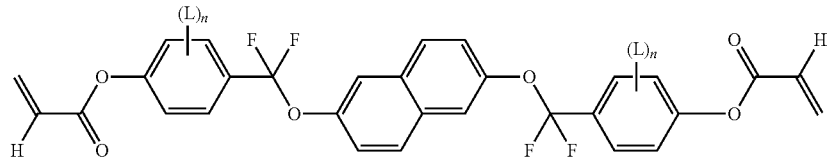
I60
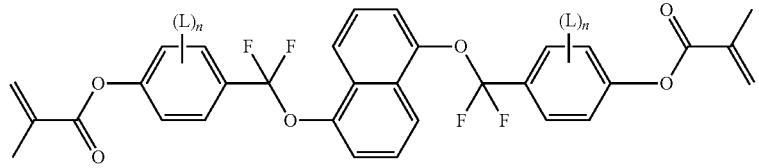
I61
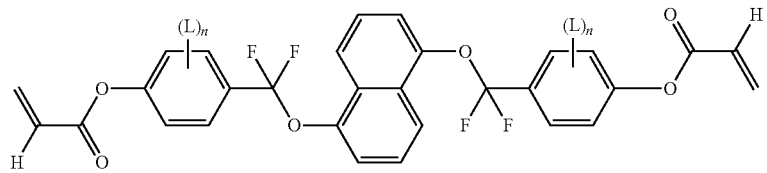
I62
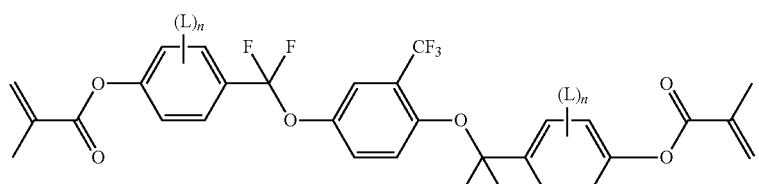
I63
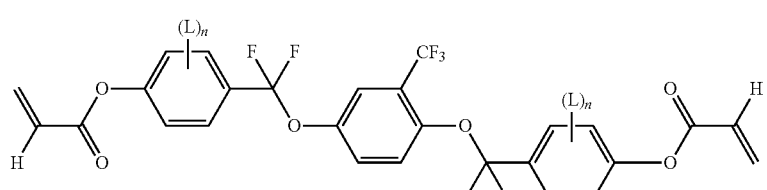
I64
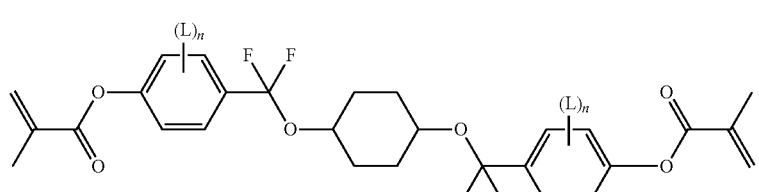
I65
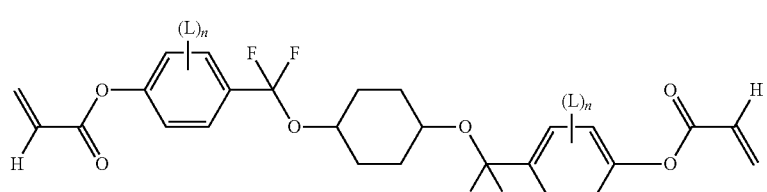
I66
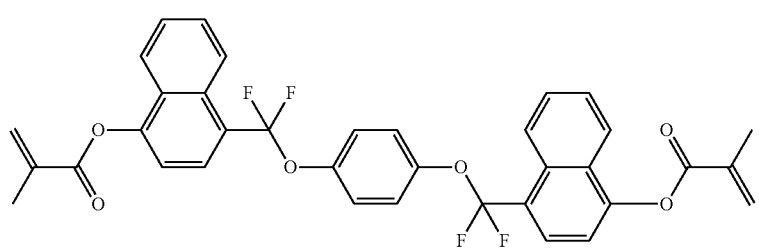
I67

-continued
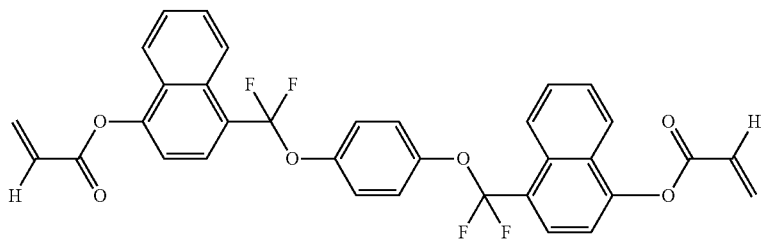
I68
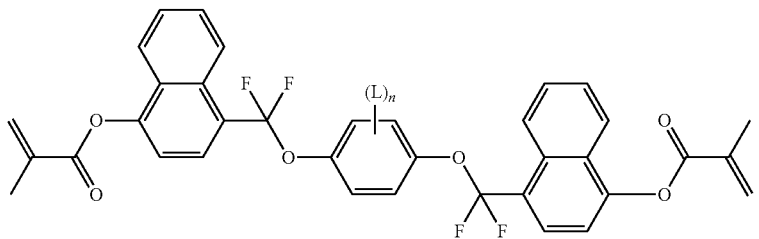
I69
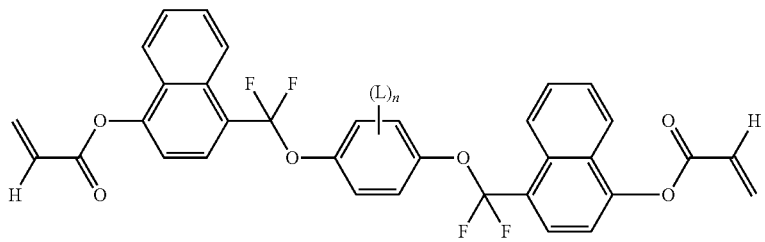
I70
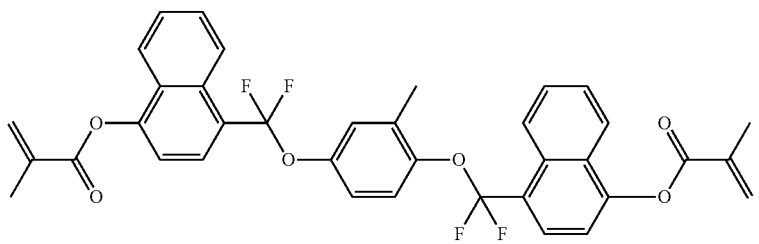
I-71
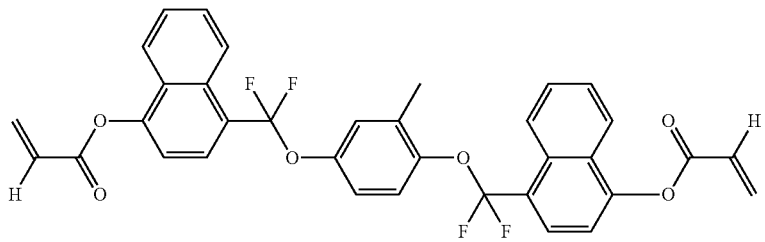
I72
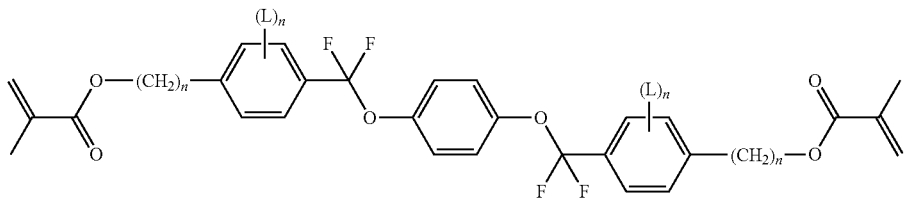
I73 in which L has on each occurrence, identically or differently, one of the meanings indicated above and below, r denotes 0, 1, 2, 3 or 4, and n denotes an integer between 1 and 24, preferably between 1 and 12, very particularly preferably between 2 and 8, and in which, if a radical is not mentioned at the end of a single or double bond, it is a terminal $CH_3$ or $CH_2$ group.

In the formulae I1-I73,

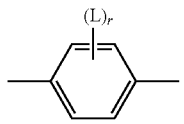

preferably denotes a group selected from the group consisting of the following formulae:

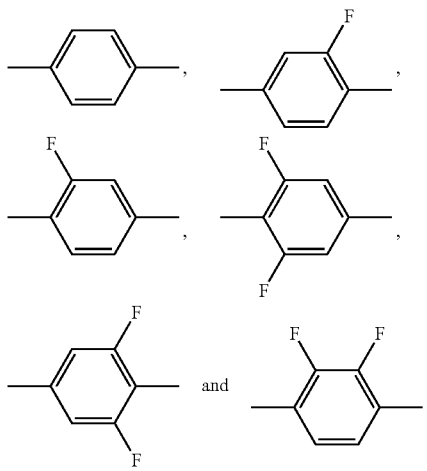

$P^a$ and $P^b$ in the compounds of the formula I and sub-formulae thereof preferably denote acrylate or methacrylate, furthermore fluoroacrylate.

$Sp^a$ and $Sp^b$ in the compounds of the formula I and sub-formulae thereof preferably denote a radical selected from the group consisting of $-(CH_2)_{p1}-$, $-(CH_2)_{p1}-O-$, $-(CH_2)_{p1}-O-CO-$ or $-(CH_2)_{p1}-O-CO-O-$ and mirror images thereof, in which p1 denotes an integer from 1 to 12, preferably from 1 to 6, particularly preferably 1, 2 or 3, where these groups are linked to $P^a$ or $P^b$ in such a way that O atoms are not directly adjacent.

The invention furthermore relates to novel compounds of the formula I $$P^a\text{-}(Sp^a)_{s1}\text{-}A^2\text{-}Q^1\text{-}A^1\text{-}Q^2\text{-}A^3\text{-}(Sp^b)_{s2}\text{-}P^b \qquad I$$

in which $P^a$, $P^b$, $Sp^a$, $Sp^b$, s1, s2, $Q^1$, $Q^2$, $A^1$, $A^2$ and $A^3$ have the meanings indicated above and below, and in which one or more of the radicals $A^1$, $A^2$ and $A^3$ are selected from the group b1) consisting of 1,3-phenylene, in which, in addition, one or two CH groups may be replaced by N and in which, in addition, one or more H atoms may be replaced by L, or the group d) consisting of saturated, partially saturated or fully unsaturated, and optionally substituted, polycyclic radicals having 5 to 20 cyclic C atoms, one or more of which may also be replaced by heteroatoms, preferably in which one or more of the radicals $A^1$, $A^2$ and $A^3$ are selected from the group consisting of 1,3-phenylene, bicyclo[1.1.1]pentane-1,3-diyl, bicyclo[2.2.2]octane-1,4-diyl, spiro[3.3]heptane-2,6-diyl,

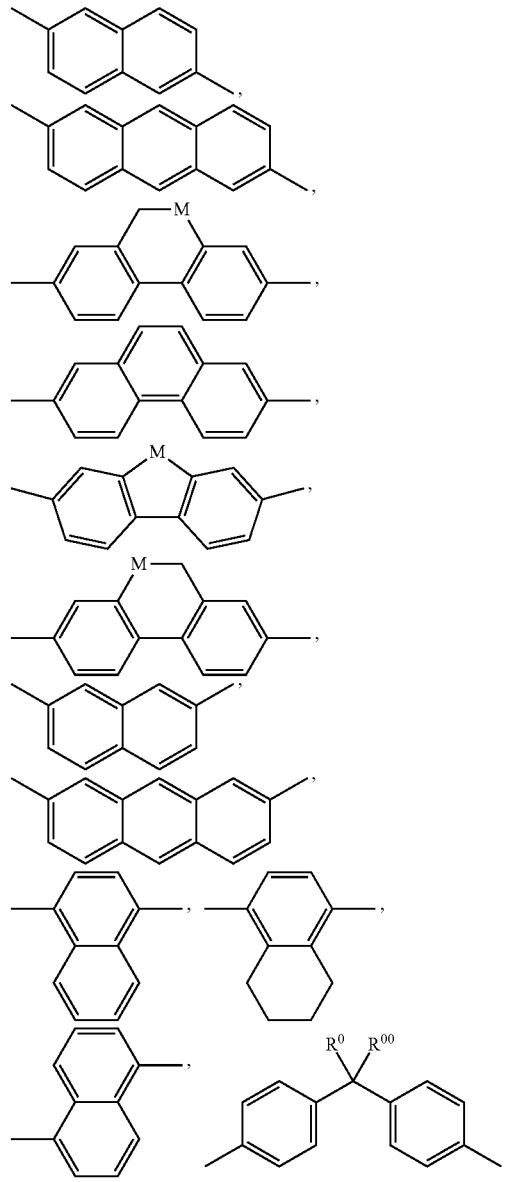

where, in addition, one or more H atoms in these radicals may be replaced by L, and/or one or more double bonds may be replaced by single bonds, and/or one or more CH groups may be replaced by N, where L, $R^0$, $R^{00}$, M, $Y^1$ and $Y^2$ have the meanings indicated in formula I.

Of these novel compounds, particular preference is given to those in which $A^1$ denotes a radical selected from group b1) or d),
$A^2$ and/or $A^3$ denote a radical selected from group b1) or d),
$A^1$ denotes a radical selected from group b1) or d), and $A^2$ and $A^3$ do not denote a radical selected from group d),
$A^2$ and/or $A^3$ denotes a radical selected from group b1) or d), and $A^1$ does not denote a radical selected from group b1) or d),
$A^1$ and/or $A^2$ and/or $A^3$ denotes a radical selected from group d),
the radicals from group d) are selected from group d1) consisting of

[Structures shown: substituted naphthalene and tetrahydronaphthalene radicals]

where, in addition, one or more H atoms in these radicals may be replaced by L as defined in formula I, where L particularly preferably denotes F, CN, SCN, $SF_5$, $CH_2F$, $CHF_2$, $CF_3$, $OCH_2F$, $OCHF_2$ or $OCF_3$, the radicals from group d) are selected from group d2) consisting of

[Structures shown: substituted naphthalene and tetrahydronaphthalene radicals]

where, in addition, one or more H atoms in these radicals may be replaced by L as defined in formula I, where L particularly preferably denotes F, CN, SCN, $SF_5$, $CH_2F$, $CHF_2$, $CF_3$, $OCH_2F$, $OCHF_2$ or $OCF_3$, the radicals $P^a$ and $P^b$ are selected from the group consisting of vinyloxy, acrylate, methacrylate, fluoroacrylate, chloroacrylate, oxetane and epoxide groups, particularly preferably acrylate or methacrylate groups, the radicals $Sp^a$ and $Sp^b$ are selected from the group consisting of —$(CH_2)_{p1}$—, —$(CH_2)_{p1}$—O—, —$(CH_2)_{p1}$—O—CO— and —$(CH_2)_{p1}$—O—CO—O— and mirror images thereof, in which p1 denotes an integer from 1 to 12, preferably from 1 to 6, particularly preferably 1, 2 or 3, and where these radicals are linked to $P^a$ or $P^b$ in such a way that O atoms are not directly adjacent, $Q^1$ denotes —$CF_2O$— and $Q^2$ denotes —$OCF_2$—, $Q^1$ denotes —$OCF_2$— and $Q^2$ denotes —$CF_2O$—, $Q^1$ and $Q^2$ denote —$CF_2O$—, $Q^1$ and $Q^2$ denote —$OCF_2$—, s1 and s2 each denote 0, s1 and s2 each denote 1, s1 denotes 1 and s2 denotes 0 or s1 denotes 0 and s2 denotes 1.

Of these novel compounds, very particular preference is given to those in which $Q^1$ denotes —$CF_2O$— and $Q^2$ denotes —$OCF_2$—.

Of these novel compounds, very particular preference is furthermore given to those selected from one or more of the following groups:

the group consisting of the formulae I9-I14, the group consisting of the formulae I19-I24, the group consisting of the formulae I33-I38, the group consisting of the formulae I43-I48, the group consisting of the formulae I57-I62 and the group consisting of the formulae I67-I72, in which L has one of the meanings indicated above and below, and n is an integer between 1 and 24, preferably between 1 and 12, very particularly preferably between 2 and 8.

The invention furthermore relates to novel intermediates for the preparation of compounds of the formula I, selected from formula IA $$G\text{-}O\text{-}(Sp^a)_{s1}\text{-}A^2\text{-}Q^1\text{-}A^1\text{-}Q^2\text{-}A^3\text{-}(Sp^b)_{s2}\text{-}O\text{-}G' \qquad \text{IA}$$

in which $Q^1$, $Q^2$, $A^1$, $A^2$, $A^3$, $Sp^a$, $Sp^b$, s1 and s2 have the meanings indicated in formula I or sub-formulae thereof, or one of the preferred meanings indicated above and below, and G and G' each, independently of one another, denote an H atom or a protecting group.

Suitable protecting groups G are known to the person skilled in the art. Preferred protecting groups are alkyl, acryl and alkylsilyl or arylsilyl groups, 2-tetrahydropyranyl or methoxymethyl.

The compounds and intermediates of the formulae I and IA and sub-formulae thereof can be prepared analogously to processes known to the person skilled in the art and described in standard works of organic chemistry, such as, for example, in Houben-Weyl, Methoden der organischen Chemie [Methods of Organic Chemistry], Thieme-Verlag, Stuttgart.

Particularly suitable and preferred processes for the preparation of compounds and intermediates of the formulae I and IA and sub-formulae thereof are depicted by way of example in the following schemes and preferably contain one or more of the steps described below.

The person skilled in the art will be able to modify the synthesis in a suitable manner and thus obtain further compounds according to the invention. The particularly preferred compounds containing an alkoxy spacer or acrylates bonded directly to the ring are obtained, for example, by reaction of dihydroquinone derivatives, such as, for example, compound 2, with the dithianylium salts 3. The compounds 4 initially formed here are converted into the compounds 5. The hydroxyl groups can subsequently be suitably functionalised, for example by esterification using methacrylic acid (cf. Scheme 1).

Scheme 1: Example of the synthesis of compounds according to the invention containing directly bonded acrylates

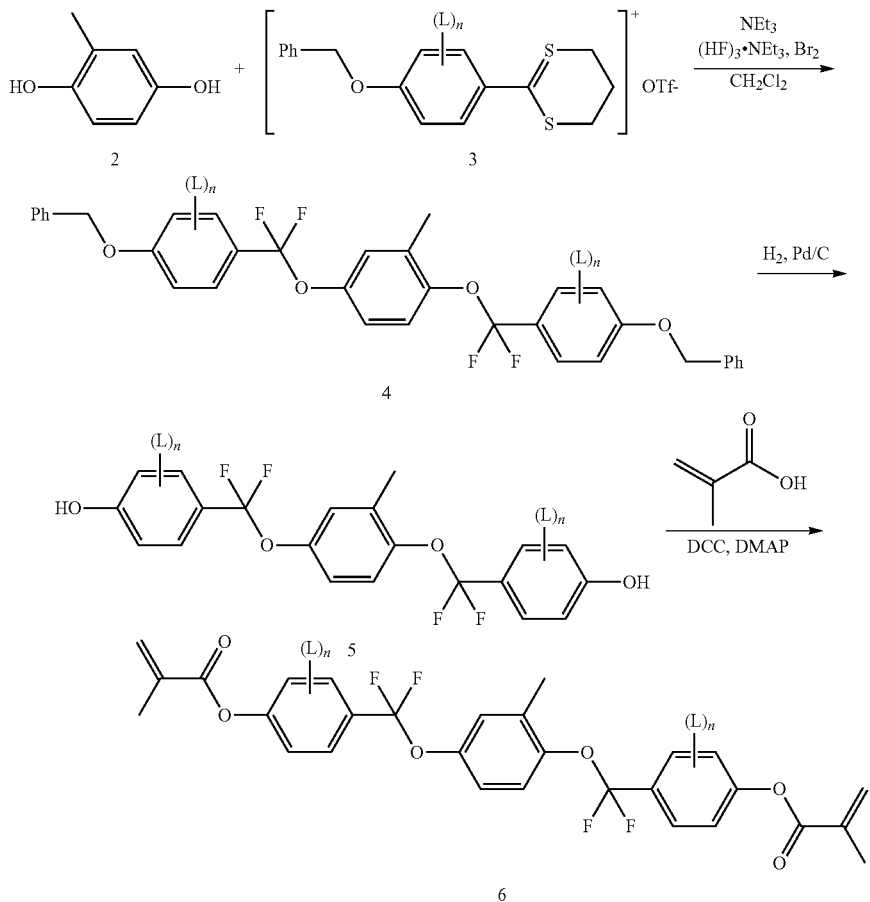

If compounds according to the invention containing alkoxy spacers are to be obtained (for example compound 8 in Scheme 2), the compounds 5 are then reacted with the bromoalkanols 6 in the presence of a suitable base. The product can subsequently be esterified again using acrylic acids.

Scheme 2: Example of the synthesis of compounds according to the invention containing alkoxy spacers

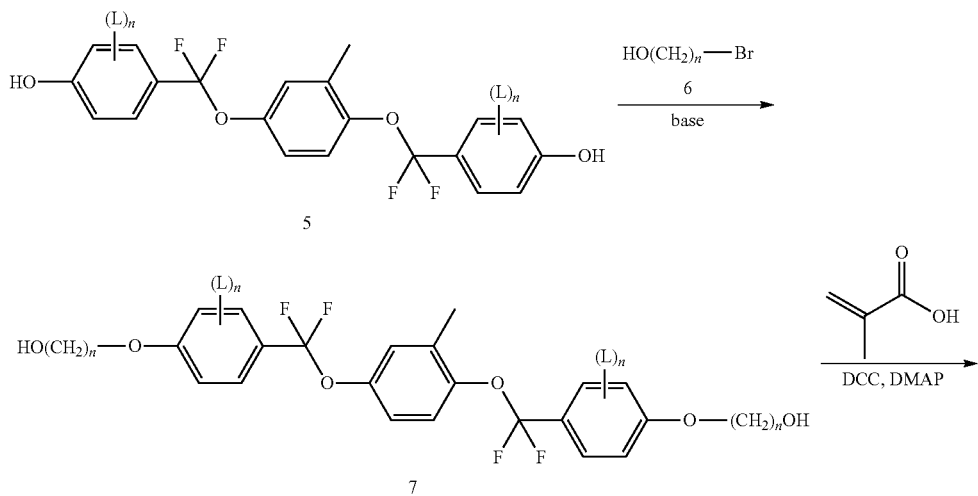

-continued

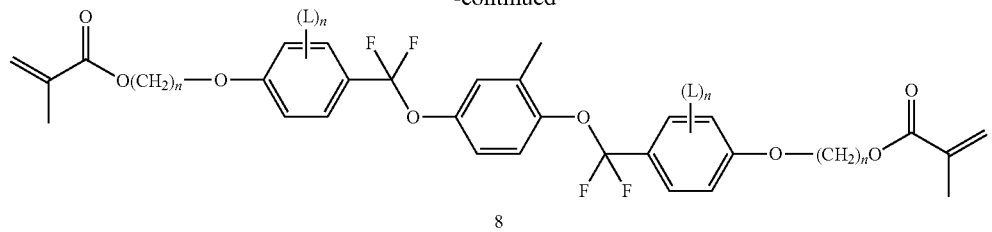

8

Alternatively, the spacer can also be introduced in a Mitsunobu reaction (cf. Scheme 3).

Scheme 3: Example of the synthesis of compounds according to the invention containing alkoxy spacers by a Mitsunobu reaction

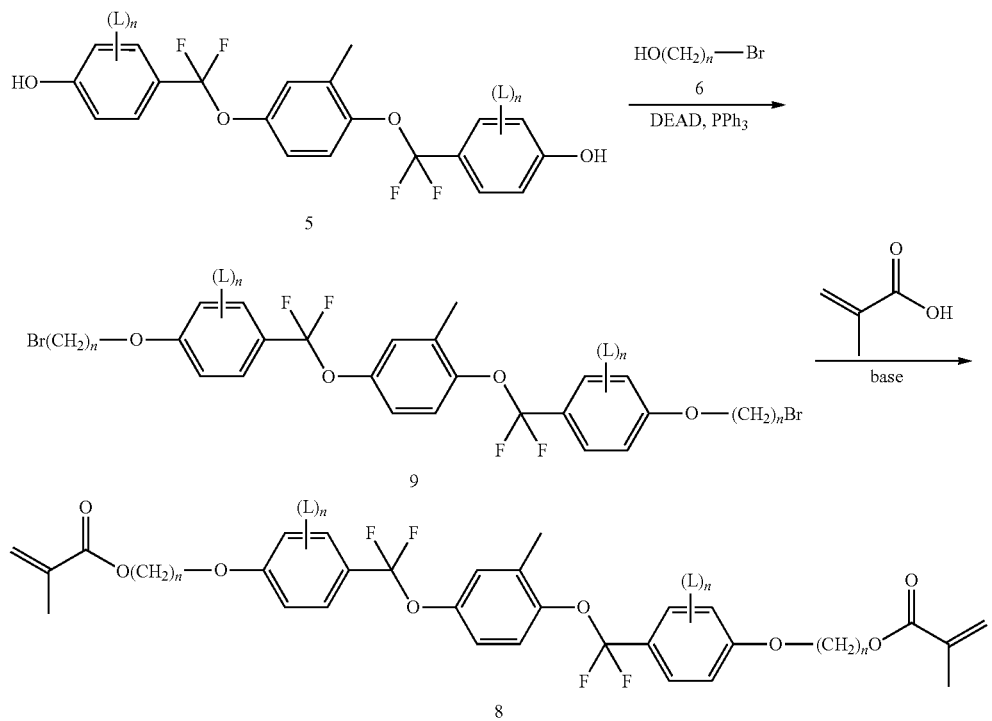

For the production of PSA displays according to the invention, the polymerisable compounds are polymerised or crosslinked (if one compound contains two or more polymerisable groups) by in-situ polymerisation in the LC medium between the substrates of the LC display with application of a voltage. The polymerisation can be carried out in one step. It is also possible firstly to carry out the polymerisation with application of a voltage in a first step in order to generate a pretilt angle, and subsequently, in a second polymerisation step without an applied voltage, to polymerise or crosslink the compounds which have not reacted in the first step ("end curing").

Suitable and preferred polymerisation methods are, for example, thermal or photopolymerisation, preferably photopolymerisation, in particular UV photopolymerisation. One or more initiators can optionally also be added here. Suitable conditions for the polymerisation and suitable types and amounts of initiators are known to the person skilled in the art and are described in the literature. Suitable for free-radical polymerisation are, for example, the commercially available photoinitiators Irgacure651®, Irgacure184®, Irgacure907®, Irgacure369® or Darocure1173® (Ciba AG). If an initiator is employed, its proportion is preferably 0.001 to 5% by weight, particularly preferably 0.001 to 1% by weight.

The polymerisable compounds according to the invention are also suitable for polymerisation without an initiator, which is accompanied by considerable advantages, such as, for example, lower material costs and in particular less contamination of the LC medium by possible residual amounts of the initiator or degradation products thereof. The polymerisation can thus also be carried out without the addition of an initiator. In a preferred embodiment, the LC medium thus comprises no polymerisation initiator.

The polymerisable component or the LC medium may also comprise one or more stabilisers in order to prevent undesired spontaneous polymerisation of the RMs, for example during storage or transport. Suitable types and amounts of stabilisers are known to the person skilled in the art and are described in the literature. Particularly suitable are, for example, the commercially available stabilisers from the Irganox® series (Ciba AG), such as, for example, Irganox® 1076. If stabilisers are employed, their proportion, based on the total amount of RMs or the polymerisable component, is preferably 10-10,000 ppm, particularly preferably 50-500 ppm.

The polymerisable compounds according to the invention can be polymerised individually, but it is also possible to polymerise mixtures which comprise two or more polymerisable compounds according to the invention, or mixtures comprising one or more polymerisable compounds according to the invention and one or more further polymerisable compounds (comonomers), which are preferably mesogenic or liquid-crystalline. In the case of polymerisation of such mixtures, copolymers form. The invention furthermore relates to the polymerisable mixtures mentioned above and below. The polymerisable compounds and comonomers are mesogenic or non-mesogenic, preferably mesogenic or liquid-crystalline.

Suitable and preferred comonomers for use in displays according to the invention are selected, for example, from the following formulae:

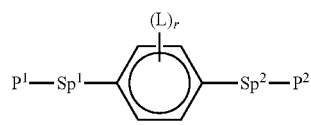
M1

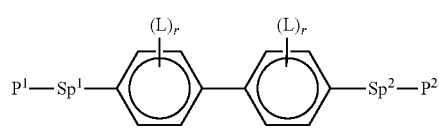
M2

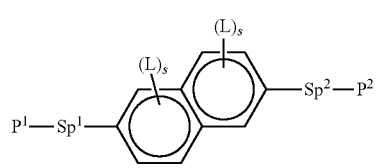
M3

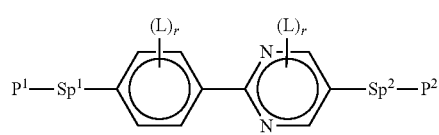
M4

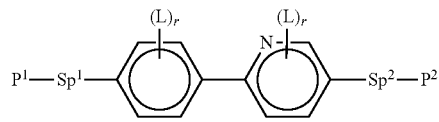
M5

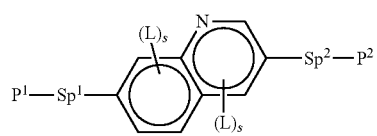
M6

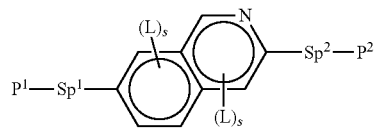
M7

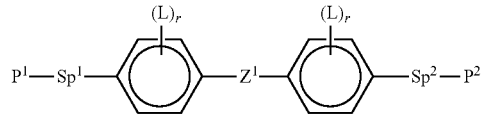
M8

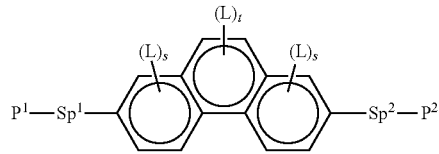
M9

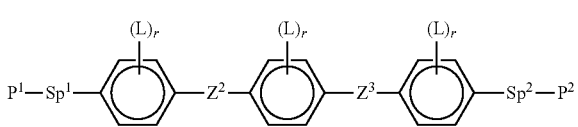
M10

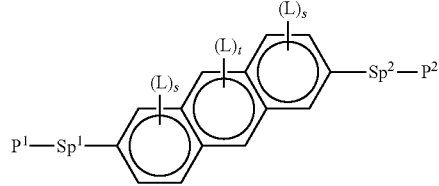
M11

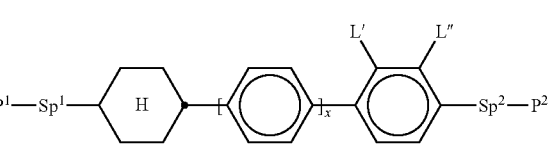
M12

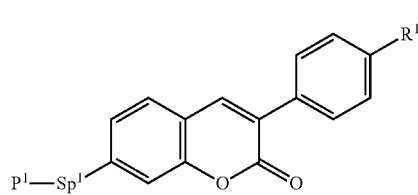
M13

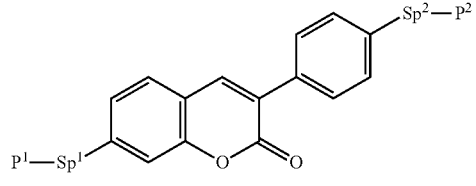
M14

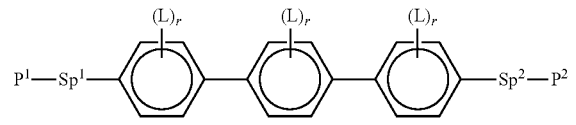
M15

M16

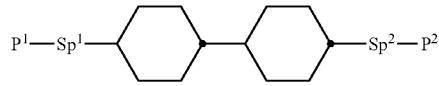
M17

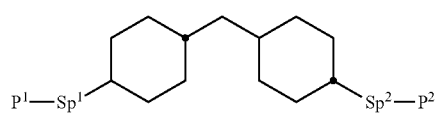
M18

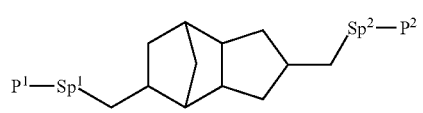
M19

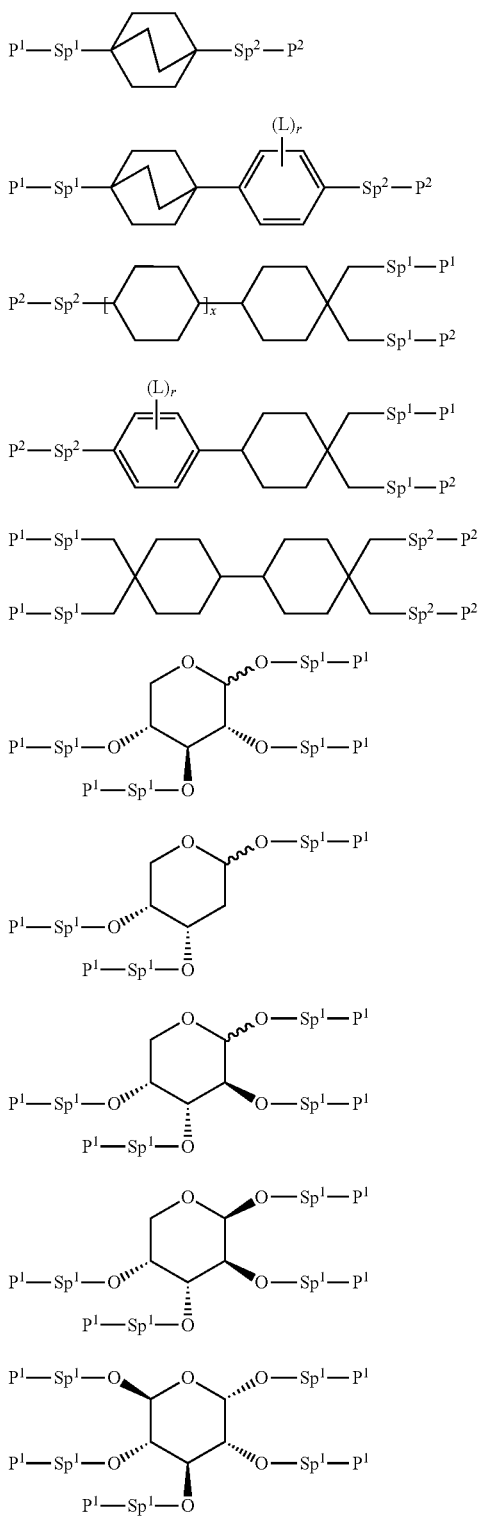

in which the individual radicals have the following meanings:

$P^1$ and $P^2$ each, independently of one another, denote a polymerisable group, preferably having one of the meanings indicated above and below for P, particularly preferably an acrylate, methacrylate, fluoroacrylate, oxetane, vinyloxy or epoxide group, $Sp^1$ and $Sp^2$ each, independently of one another, denote a single bond or a spacer group, preferably having one of the meanings indicated above and below for $Sp^a$, particularly preferably —$(CH_2)_{p1}$—, —$(CH_2)_{p1}$—O—, —$(CH_2)_{p1}$—CO—O— or —$(CH_2)_{p1}$—O—CO—O—, in which p1 is an integer from 1 to 12, and where the linking to the adjacent ring in the last-mentioned groups takes place via the O atom, where, in addition, one or more of the radicals $P^1$-$Sp^1$- and $P^2$-$Sp^2$- may denote a radical $R^{aa}$, with the proviso that at least one of the radicals $P^1$-$Sp^1$- and $P^2$-$Sp^2$- present does not denote $R^{aa}$, $R^{aa}$ denotes H, F, Cl, CN or straight-chain or branched alkyl having 1 to 25 C atoms, in which, in addition, one or more non-adjacent $CH_2$ groups may each be replaced, independently of one another, by $C(R^0)$=$C(R^{00})$—, —C≡C—, —$N(R^0)$—, —O—, —S—, —CO—, —CO—O—, —O—CO—, —O—CO—O— in such a way that O and/or S atoms are not linked directly to one another and in which, in addition, one or more H atoms may be replaced by F, Cl, CN or $P^1$-$Sp^1$-, particularly preferably straight-chain or branched, optionally mono- or polyfluorinated alkyl, alkoxy, alkenyl, alkynyl, alkylcarbonyl, alkoxycarbonyl or alkylcarbonyloxy having 1 to 12 C atoms (where the alkenyl and alkynyl radicals have at least two C atoms and the branched radicals have at least three C atoms), $R^0$, $R^{00}$ each, independently of one another and identically or differently on each occurrence, denote H or alkyl having 1 to 12 C atoms, $R^y$ and $R^z$ each, independently of one another, denote H, F, $CH_3$ or $CF_3$, $Z^1$ denotes —O—, —CO—, —$C(R^y R^z)$— or —$CF_2 CF_2$—, $Z^2$ and $Z^3$ each, independently of one another, denote —CO—O—, —O—CO—, —$CH_2$O—, —$OCH_2$—, —$CF_2$O—, —$OCF_2$— or —$(CH_2)_n$—, where n is 2, 3 or 4, L on each occurrence, identically or differently, denotes F, Cl, ON, SON, $SF_5$ or straight-chain or branched, optionally mono- or polyfluorinated alkyl, alkoxy, alkenyl, alkynyl, alkylcarbonyl, alkoxycarbonyl, alkylcarbonyloxy or alkoxycarbonyloxy having 1 to 12 C atoms, preferably F, L' and L" each, independently of one another, denote H, F or Cl, r denotes 0, 1, 2, 3 or 4, s denotes 0, 1, 2 or 3, t denotes 0, 1 or 2, x denotes 0 or 1.

In addition to the compounds of the formula I or IA, the LC medium or the polymerisable component preferably comprises one or more compounds selected from the group consisting of the formulae M16-M29, particularly preferably consisting of the formulae M16-M21, very particularly preferably consisting of the formulae M16, M17 and M18.

The LC medium or the polymerisable component preferably comprises no compounds of the formula M10 in which $Z^2$ and $Z^3$ denote —COO— or —OCO—.

Besides the polymerisable compounds described above, the LC media for use in the LC displays according to the invention comprise an LC mixture ("host mixture") comprising one or more, preferably two or more, low-molecular-weight (i.e. monomeric or unpolymerised) compounds. The latter are stable or unreactive to a polymerisation reaction under the conditions used for polymerisation of the polymerisable compounds. In principle, any LC mixture which is suitable for use in conventional VA and OCB displays is suitable as host mixture.

Suitable LC mixtures are known to the person skilled in the art and are described in the literature. LC media for VA displays are described in EP 1 378 557 A1. LC media for OCB displays are described in EP 1 306 418 A1 and DE 102 24 046 A1. LC media for LC displays having a blue phase are described in WO 2006/063662 A1 and the documents cited therein.

Particularly preferred LC media for use in LC displays having a blue phase are described below:

An LC medium according to the invention having a blue phase preferably comprises
- a polymerisable component A, preferably in a concentration of 1 to 25%, particularly preferably 2 to 20%, very particularly preferably 3 to 15%, comprising, preferably consisting principally of, very particularly preferably consisting exclusively of, one or more compounds of the formula I and optionally one or more additional polymerisable compounds, and
- a liquid-crystalline component B comprising one or more, preferably two or more, low-molecular-weight (i.e. monomeric and unpolymerisable) compounds, preferably in a concentration of 20-100%, preferably having positive dielectric anisotropy, preferably consisting principally of, very particularly preferably consisting exclusively of, one or more compounds of the formula II

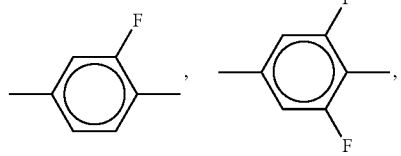

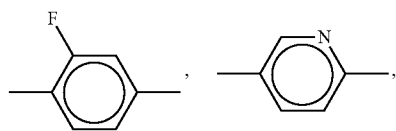

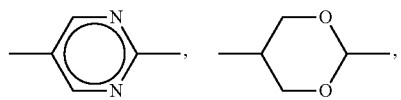

$Z^{21}$, $Z^{22}$ each, independently of one another and on each occurrence identically or differently, denote a single

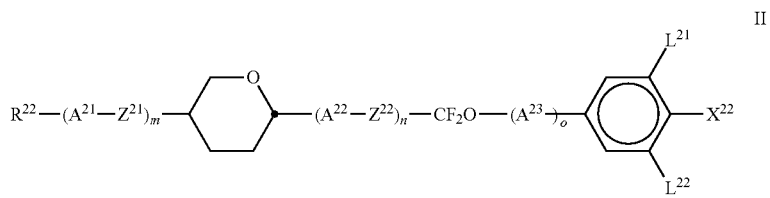

in which the individual radicals have the following meanings:

$R^{22}$ denotes H, F, Cl, ON, NOS, $SF_5$, $SO_2CF_3$ or straight-chain or branched alkyl having 1 to 20 C atoms, which is unsubstituted or mono- or polysubstituted by F, Cl or CN, and in which, in addition, one or more non-adjacent $CH_2$ groups may also each be replaced, independently of one another, by —O—, —S—, —NH—, —$NR^{01}$—, —$SiR^{01}R^{02}$—, —CO—, —COO—, —OCO—, —OCO—O—, —S—CO—, —CO—S—, —$CY^{01}$=$CY^{02}$— or —C≡C— in such a way that O and/or S atoms are not linked directly to one another, $Y^{01}$, $Y^{02}$ each, independently of one another, denote F, Cl or ON, one of the radicals $Y^{01}$ and $Y^{02}$ also denotes H, $R^{01}$, $R^{02}$ each, independently of one another, denote H or alkyl having 1 to 12 C atoms, $A^{21}$, $A^{22}$, $A^{23}$ each, independently of one another and on each occurrence identically or differently, denote

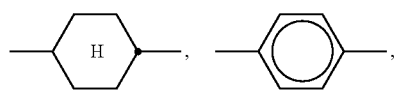

bond, —$(CH_2)_4$—, —$CH_2CH_2$—, —$CF_2$—$CF_2$—, —$CF_2$—$CH_2$—, —$CH_2$—$CF_2$—, —CH=CH—, —CF=CF—, —CF=CH—, —$(CH_2)_3O$—, —$O(CH_2)_3$—, —CH=CF—, —C≡O—, —$CH_2O$—, —$OCH_2$—, —$CF_2O$—, —$OCF_2$—, —CO—O— or —O—CO—, $X^{22}$ denotes F, Cl, —CN, —NCS, —$SF_5$, —$SO_2CF_3$, or alkyl, alkenyl, alkenyloxy, alkylalkoxy or alkoxy having 1 to 3 C atoms, which is mono- or polysubstituted by F, Cl or CN, $L^{21}$, $L^{22}$ each, independently of one another, denote H or F, m denotes 0, 1 or 2, n denotes 0, 1, 2 or 3, o denotes 0, 1 or 2, where m+n+o denotes 0, 1, 2 or 3, preferably 0, 1 or 2, optionally a liquid-crystalline component C comprising one or more, preferably two or more, low-molecular-weight (i.e. monomeric and unpolymerisable) compounds, preferably in a concentration of 1 to 25%, preferably consisting principally of, very particularly preferably consisting exclusively of, one or more compounds of the formula III

III

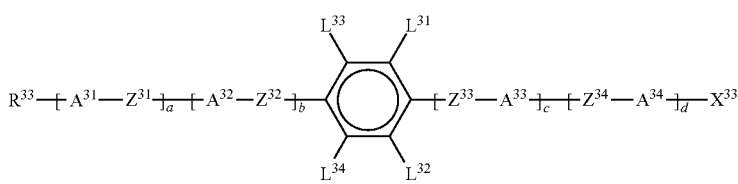

in which
a, b, c, d each, independently of one another, denote 0, 1 or 2, where
a+b+c+d is 0, 1, 2, 3 or 4,
$A^{31}$, $A^{32}$, $A^{33}$, $A^{34}$ each, independently of one another and on each occurrence identically or differently, denote

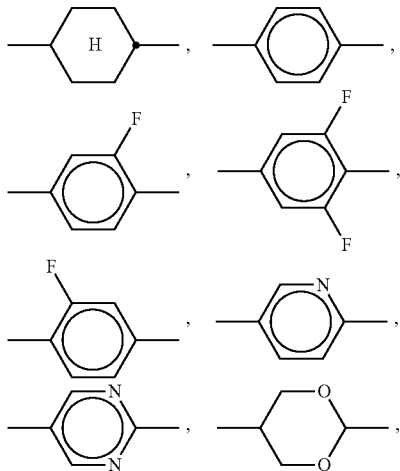

$Z^{31}$, $Z^{32}$, $Z^{33}$, $Z^{34}$ each, independently of one another and on each occurrence identically or differently, denote a single bond, —(CH$_2$)$_4$—, —CH$_2$CH$_2$—, —CF$_2$—CF$_2$—, —CF$_2$—CH$_2$—, —CH$_2$—CF$_2$—, —CH=CH—, —CF=CF—, —CF=CH—, —(CH$_2$)$_3$O—, —O(CH$_2$)$_3$—, —CH=CF—, —C≡C—, —CH$_2$O—, —OCH$_2$—, —CF$_2$O—, —OCF$_2$—, —CO—O— or —O—CO—,
$R^{33}$ denotes alkyl or alkoxy having 1 to 15 C atoms, which is unsubstituted or mono- or polysubstituted by F, Cl or CN, and in which, in addition, one or more non-adjacent CH$_2$ groups may also each be replaced, independently of one another, by —O—, —S—, —SiR$^x$R$^y$—, —CH=CH—, —C≡C—, —CO—O— and/or —O—CO— in such a way that O and/or S atoms are not linked directly to one another, preferably a straight-chain alkyl, alkoxy, alkenyl, alkenyloxy or —O-alkylene-O-radical having up to 10 C atoms, which is unsubstituted or mono- or polysubstituted by F or Cl,
$L^{31}$, $L^{32}$, $L^{33}$, $L^{34}$ each, independently of one another, denote H, F, Cl, CN, or alkyl or alkoxy having 1 to 15 C atoms, which is unsubstituted or mono- or polysubstituted by F, Cl or CN, and in which, in addition, one or more non-adjacent CH$_2$ groups may also each be replaced, independently of one another, by —O—, —S—, —SiR$^x$R$^y$—, —CH=CH—, —C≡C—, —CO—O— and/or —O—CO— in such a way that O and/or S atoms are not linked directly to one another, with the proviso that at least one of the radicals $L^{31}$, $L^{32}$, $L^{33}$ and $L^{34}$ is other than H,
$X^{33}$ denotes F, Cl, CF$_3$, OCF$_3$, CN, NCS, —SF$_5$ or —SO$_2$—R$^z$,
$R^x$ and $R^y$ each, independently of one another, denote H, alkyl or alkoxy having 1 to 7 C atoms, preferably methyl, ethyl, propyl or butyl, and
$R^z$ denotes alkyl having 1 to 7 C atoms, which is unsubstituted or mono- or polysubstituted by F or Cl, preferably CF$_3$, C$_2$F$_5$ or n-C$_4$F$_9$,
a component D, preferably in a concentration of 1-20%, comprising one or more optically active and/or chiral compounds, preferably having an HTP≥20 µm$^{-1}$, preferably ≥40 µm$^{-1}$, very particularly preferably ≥60 µm$^{-1}$.

The chiral component D preferably comprises one or more chiral compounds having a mesogenic structure and preferably has one or more mesophases, particularly preferably at least one cholesteric phase. Preferred chiral compounds of component D are, for example, chiral dopants which are known from the prior art and/or are commercially available, such as cholesteryl nonanoate (CN), R/S-811, R/S-1011, R/S-2011, R/S-3011, R/S-4011, R/S-5011 or CB-15 (Merck KGaA, Darmstadt). Particular preference is given to chiral dopants containing one or more chiral groups and one or more mesogenic groups, as disclosed, for example, in DE 34 25 503, DE 35 34 777, DE 35 34 778, DE 35 34 779, DE 35 34 780, DE 43 42 280, EP 01 038 941 and DE 195 41 820. Preference is furthermore given to sorbitols, as described, for example, in WO 98/00428 A1, hydrobenzoins, as described, for example, in GB 2 328 207 A, chiral binaphthols, as described, for example, in WO 02/94805 A1, chiral binaphthol acetals, as described, for example, in WO 02/34739 A1, chiral TADDOLs, as described, for example, in WO 02/06265 A1, or chiral compounds containing fluorinated bridging groups, as described, for example, in WO 02/06196 A1 or WO 02/06195 A1.

The clearing point of the LC medium according to the invention having a blue phase is preferably in the range from −30° C. to 100° C.

The LC medium preferably comprises one, two, three, four or more than four chiral compounds. The LC medium preferably comprises chiral compounds in a total concentration of 0.01 to 25%, preferably 0.1-20%, particularly preferably 0.5 to 20%, very particularly 3-15%.

The proportion of the compounds of the formula I in the total content of all polymerisable compounds in the LC medium, or the proportion of the compounds of the formula I in the polymerisable component A), is preferably 20 to 80%, particularly preferably 40 to 60%.

In a further preferred embodiment, the proportion of the compounds of the formula I in the total content of all polymerisable compounds in the LC medium, or the proportion of the compounds of the formula I in the polymerisable component A), is at least 50% and particularly preferably 60% to 100%.

Further particularly preferred embodiments are described below:

The LC medium comprises one, two or three compounds of the formula I;

Component B comprises, in addition to the compounds of the formula II, one or more ester compounds of the formula Z:

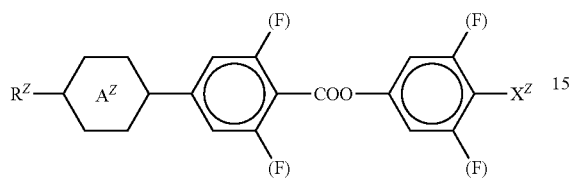

Z in which $R^Z$ has one of the meanings indicated for $R^{22}$ in formula II,

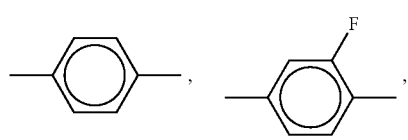

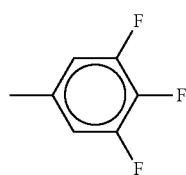

$X^Z$ denotes F, Cl, CN, NCS, $OCF_3$, $CF_3$ or $SF_5$, and (F) denotes F or H, preferably in a concentration of 5 to 35%, particularly preferably 10 to 30%, very particularly preferably 10 to 20%.

Component B comprises, in addition to the compounds of the formula II, one or more compounds of the formula N:

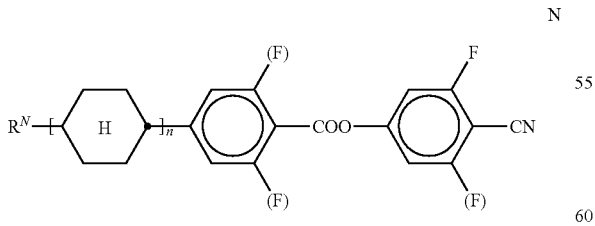

N in which $R^N$ has one of the meanings indicated for $R^{22}$ in formula II and preferably denotes alkyl or alkyl-C≡C, "alkyl" denotes alkyl having 1 to 7 C atoms, which is preferably straight-chain, (F) denotes F or H, and n denotes 0 or 1.

Component B comprises, in addition to the compounds of the formula II, one or more compounds of the formula E:

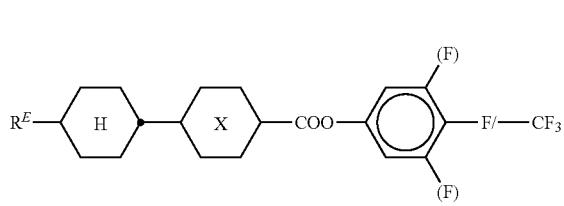

E in which $R^E$ has one of the meanings indicated for $R^{22}$ in formula II and preferably denotes C1-C7-alkyl, and

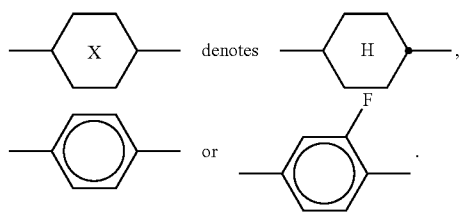

preferably in a concentration of 10-30%, particularly preferably 15-25%.

The LC medium additionally comprises one or more compounds of the formulae Q1 and/or Q2:

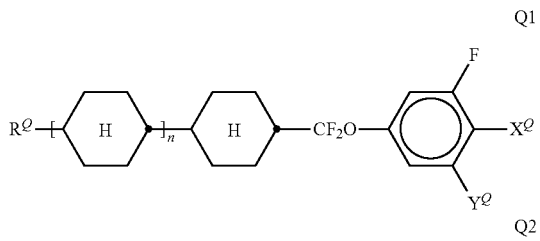

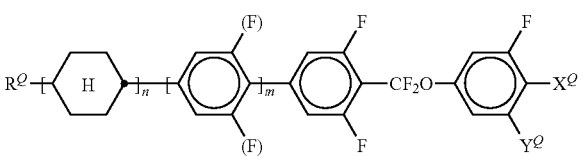

in which $R^Q$ has one of the meanings indicated for $R^{22}$ in formula II, $X^Q$ has one of the meanings indicated for $X^Z$ in formula Z, $Y^Q$ denotes H or F, and n and m each, independently of one another, denote 0 or 1.

The LC medium additionally comprises one or more compounds of the formulae Dx1 and/or Dx2:

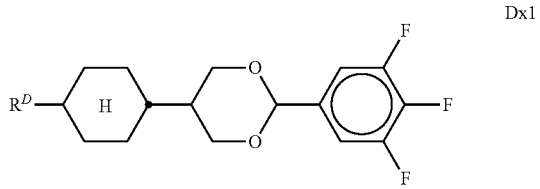

Dx1

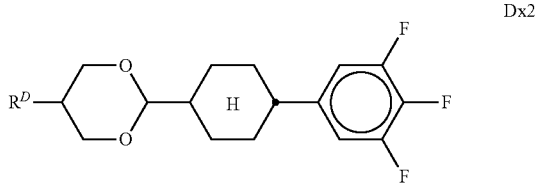

in which $R^D$ has one of the meanings indicated for $R^{22}$ in formula II.

Particular preference is given to LC media which, besides one or more compounds of the formula I, comprise one or more compounds of the formula II, in particular in which $X^{22}$ denotes F, Cl, CN, NCS, $CF_3$ or $OCF_3$.

The compounds of the formulae I, II, III, Z, N, E, Q1, Q2, Dx1 and Dx2 are colourless, stable and readily miscible with one another or with other liquid-crystalline substances.

The individual components and compounds of the formulae I, II, III, Z, N, E, Q1, Q2, Dx1 and Dx2 of the LC media according to the invention are either known or methods for the preparation thereof can readily be derived from the prior art by the person skilled in the relevant art, since they are based on standard methods described in the literature.

The LC media according to the invention are prepared in a manner conventional per se, for example by mixing one or more of the above-mentioned compounds with one or more polymerisable compounds as defined above, and optionally with further liquid-crystalline compounds and/or additives. In general, the desired amount of the components used in lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing. The invention furthermore relates to the process for the preparation of the LC media according to the invention.

The LC media according to the invention for LC displays having a blue phase may also comprise further additives known to the person skilled in the art and described in the literature, such as, for example, polymerisation initiators, inhibitors, stabilisers or surface-active substances. These may be polymerisable or unpolymerisable. Polymerisable additives are accordingly ascribed to the polymerisable component. Unpolymerisable additives are accordingly ascribed to the liquid-crystalline component.

The structure of the LC displays according to the invention having a blue phase, with polarisers, electrode substrates and surface-treated electrode layers, corresponds to the conventional structure for displays of this type which is known to the person skilled in the art, as described in the prior art, for example in DE 102 17 273 A1, DE 102 41 301, DE 102 41 301, DE 102 536 06, DE 103 13 979.

An LC display according to the invention preferably comprises the following components:
one or two substrates,
an electrode arrangement having two electrodes on only one of the two substrates or having one electrode on each of the two substrates,
one or two polarisers, and
a layer of an LC medium according to the invention located between the two substrates,
where the display is operated at a temperature at which the LC medium in the unswitched state has an optically isotropic phase, preferably a blue phase.

The phase transition of the LC medium into the blue phase usually takes place starting from a cholesteric phase which exists at lower temperatures than the blue phase. The operating temperature of the LC display according to the invention (i.e. after polymer stabilisation) is preferably above the temperature of the phase transition of the LC medium into the blue phase (i.e. usually the cholesteric phase—blue phase transition), particularly preferably 0.2 to 50°, very particularly preferably 0.1 to 40°, above this phase-transition temperature. Furthermore, the operating temperature of the LC display is preferably below the temperature of the phase transition of the LC medium from the blue phase into the isotropic phase (also known as the clearing point). However, the display can also be operated in the isotropic phase, i.e. above the clearing point.

The LC media according to the invention having a blue phase may, in addition to the above-mentioned compounds of the formulae II and III, and in addition or alternatively to the above-mentioned compounds of the formulae Z, N, E, Q1, Q2, Dx1 and Dx2, also comprise further liquid-crystalline compounds in order, for example, to adapt the physical properties. Such compounds are known to the person skilled in the art. Their concentration in the LC media is preferably 0 to 30%, particularly preferably 0 to 20%, very particularly preferably 5 to 15%.

The liquid-crystalline component of an LC medium according to the invention (i.e. before polymer stabilisation) preferably has a temperature range of the blue phase, or, if a plurality of sequential blue phases occur, a combined temperature range of all blue phases, whose total width is 2° C. or more, preferably 5° C. or more, particularly preferably 10° C. or more, very particularly preferably 20° C. or more.

The liquid-crystalline component of an LC medium according to the invention (i.e. before polymer stabilisation) preferably exhibits a temperature range of the blue phase(s) at least in the range from 10° C. to 30° C., particularly preferably from 10° C. to 40° C., very particularly preferably from 0° C. to 50° C.

"At least" above and below means that the blue phase(s) may also extend below the lower limit value indicated in each case and/or above the upper limit value indicated in each case.

In a further preferred embodiment, the liquid-crystalline component of an LC medium according to the invention (i.e. before polymer stabilisation) exhibits a temperature range of the blue phase(s) at least in the range from 20° C. to 40° C., particularly preferably at least from 30° C. to 80° C., very particularly preferably at least from 30° C. to 90° C. Preference is furthermore given to LC media having a temperature range of the blue phase(s) at least from −20° C. to 50° C.

An LC medium according to the invention comprising the polymerised component (i.e. after polymer stabilisation) preferably exhibits a temperature range of the blue phase(s) at least in the range from 30° C. to 70° C., preferably from 20° C. to 70° C., particularly preferably from 0° C. to 80° C., very particularly preferably from −20° C. to 80° C.

The phase-transition temperature of the transition from the cholesteric phase into the blue phase T(Ch,BP), also known as T(N*,BP), of an LC medium according to the invention comprising the polymerisable component is preferably reduced by the polymerisation of the polymerisable component. The temperature of the transition from the blue phase into the isotropic phase T(BP, I) is preferably kept constant or is increased. This means that the polymer stabilisation of the blue phase(s) is preferably carried out in such a way that the phase-transition temperature T(Ch,BP) indicated above is shifted to lower temperatures, i.e. the blue phase(s) is (are) preferably broadened at least to lower temperatures and particularly preferably both to lower and to higher temperatures. Preferably T(Ch,BP) is kept constant or lowered (i.e., reduced) during polymerization, whereas T(BP,I) is also kept constant or increased (i.e., not reduced).

Particularly preferred LC media for use in PSA displays, in particular in PSA-VA, PSA-OCB, PSA-IPS, PSA-FFS or PSA-TN displays, are described below.

An LC medium according to the invention for use in PSA-VA, PSA-OCB, PSA-IPS, PSA-FFS or PSA-TN displays according to the invention preferably comprises:
- <5%, particularly preferably <1%, very particularly preferably <0.5%, of the polymerisable component,
- >95%, particularly preferably >99%, of the liquid-crystalline component,
- <5% by weight, particularly preferably <1% by weight, very particularly preferably <0.5% by weight, of polymerisable compounds, in particular polymerisable compounds of the formula I mentioned above or sub-formulae thereof,
- one, two or three polymerisable compounds of the formula I or sub-formulae thereof according to the invention,
- a polymerisable component which comprises exclusively polymerisable compounds of the formula I or sub-formulae thereof according to the invention,
- a liquid-crystalline component which is an LC compound or an LC mixture which has a nematic liquid-crystal phase,
- a polymerisable and/or liquid-crystalline component which comprises exclusively achiral compounds,
- a polymerisable component which comprises one or more polymerisable compounds containing one polymerisable group (monoreactive) and one or more polymerisable compounds according to the invention containing two or more, preferably two, polymerisable groups (di- or multireactive), preferably selected from compounds of the formula I or sub-formulae thereof, and optionally from the above-mentioned comonomers selected from the list comprising the formulae M1-M29,
- a polymerisable component which comprises exclusively polymerisable compounds according to the invention containing two polymerisable groups (direactive), preferably selected from compounds of the formula I or sub-formulae thereof, and optionally additionally from the above-mentioned comonomers from the list comprising the formulae M1-M29,
- apart from the polymerisable compounds according to the invention, in particular of the formula I or sub-formulae thereof, and the comonomers, no compounds which contain a terminal vinyloxy group (—O—CH=CH$_2$),
- 1 to 5, preferably 1, 2 or 3, polymerisable compounds, preferably selected from polymerisable compounds according to the invention, in particular of the formula I or sub-formulae thereof.

Particularly preferred LC media for use in PSA-VA displays are indicated below:
a) LC medium which comprises one or more compounds of the formulae CY and/or PY:

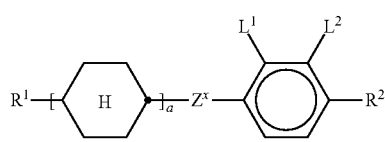

CY

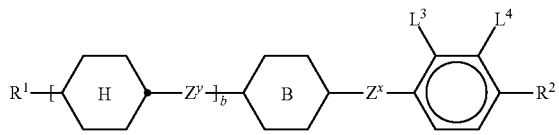

PY in which the individual radicals have the following meanings:

a denotes 1 or 2, b denotes 0 or 1,

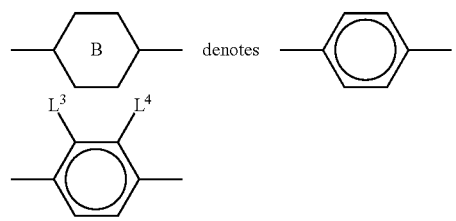

$R^1$ and $R^2$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another, preferably alkyl or alkoxy having 1 to 6 C atoms, $Z^x$ and $Z^y$ each, independently of one another, denote —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond, $L^{1-4}$ each, independently of one another, denote F, Cl, OCF$_3$, CF$_3$, CH$_3$, CH$_2$F, CHF$_2$.

Preferably, both radicals $L^1$ and $L^2$ denote F or one of the radicals $L^1$ and $L^2$ denotes F and the other denotes Cl, or both radicals $L^3$ and $L^4$ denote F or one of the radicals $L^3$ and $L^4$ denotes F and the other denotes Cl.

The compounds of the formula CY are preferably selected from the group consisting of the following sub-formulae:

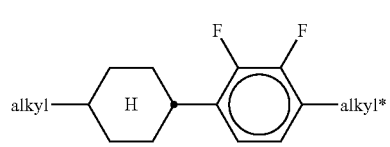

CY1

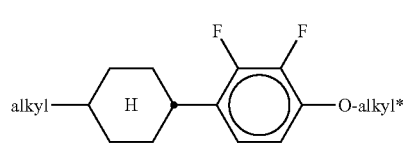

CY2

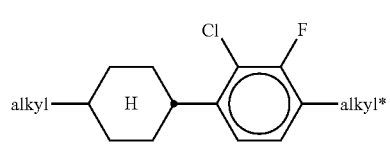

CY3

CY4
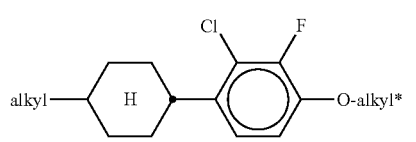
CY5
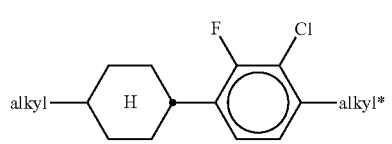
CY6
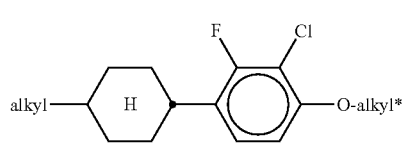
CY7
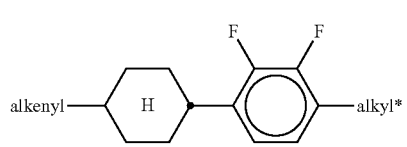
CY8
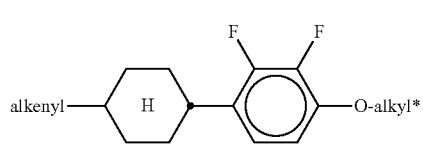
CY9
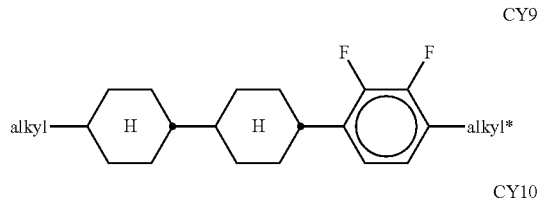
CY10
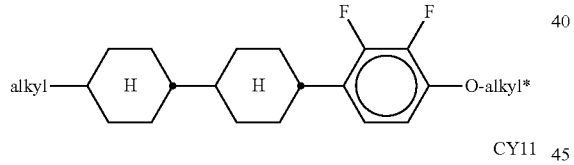
CY11
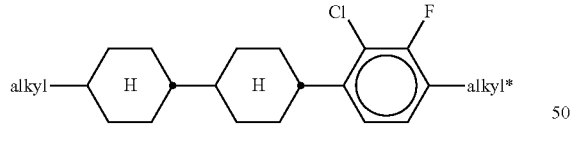
CY12
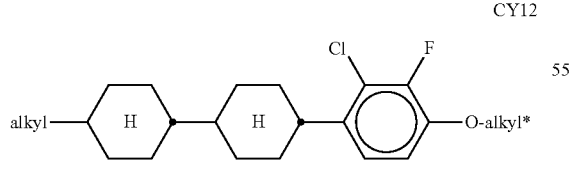
CY13
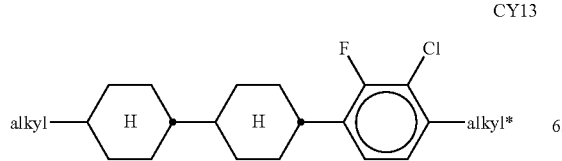
CY14
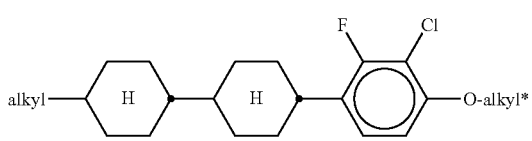
CY15
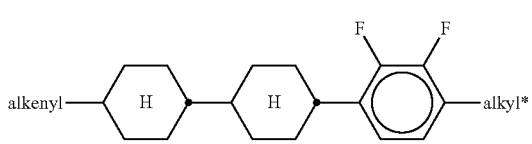
CY16
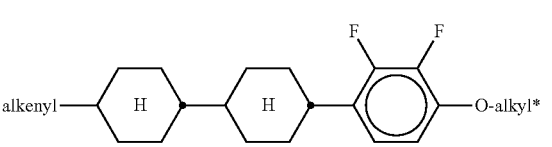
CY17
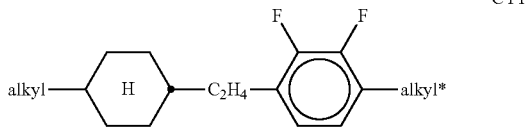
CY18
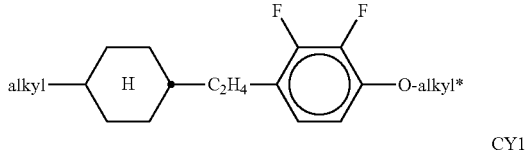
CY19
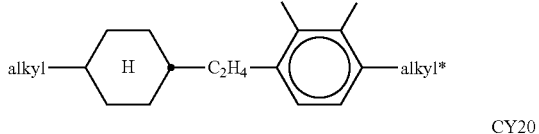
CY20
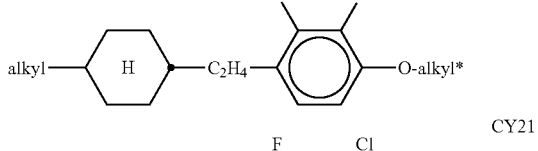
CY21
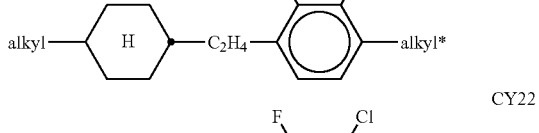
CY22
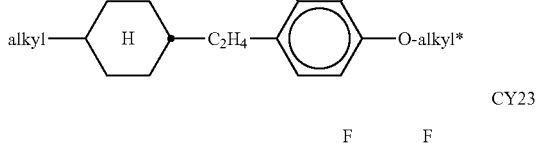
CY23
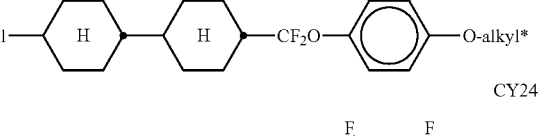
CY24
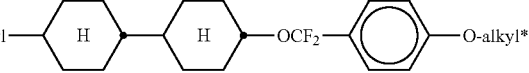

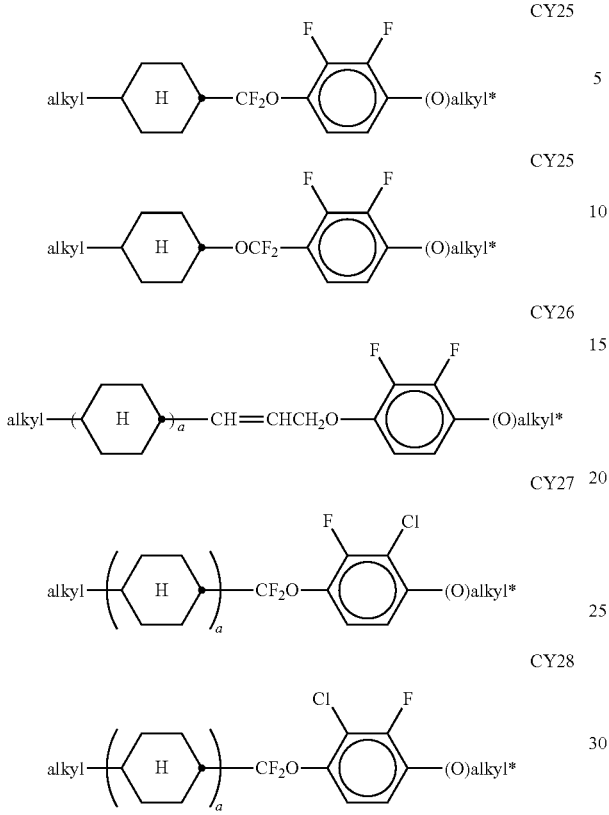

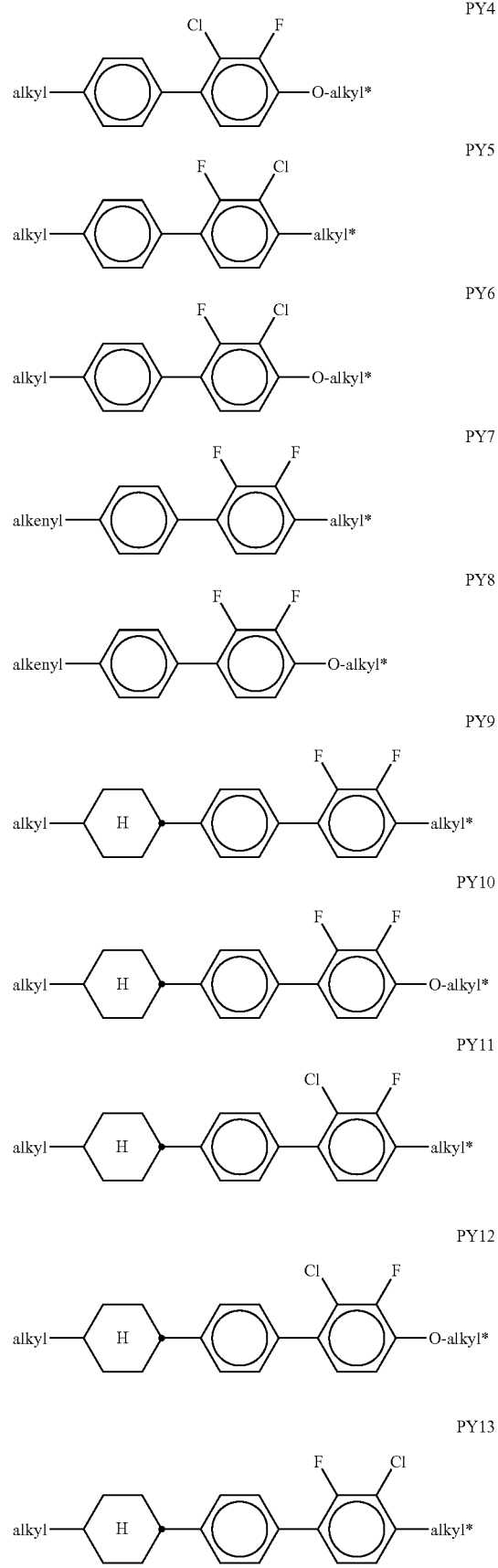

in which a denotes 1 or 2, alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

The compounds of the formula PY are preferably selected from the group consisting of the following sub-formulae:

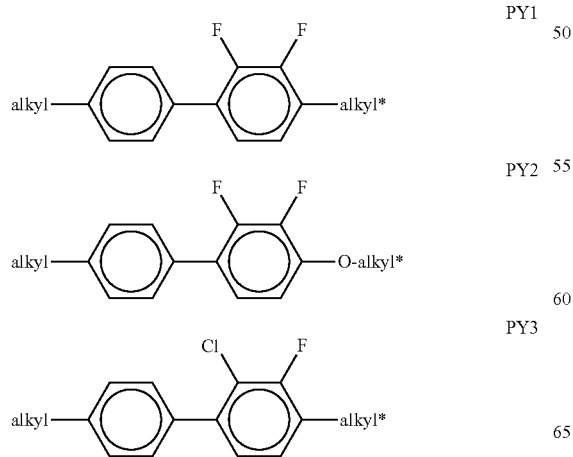

-continued

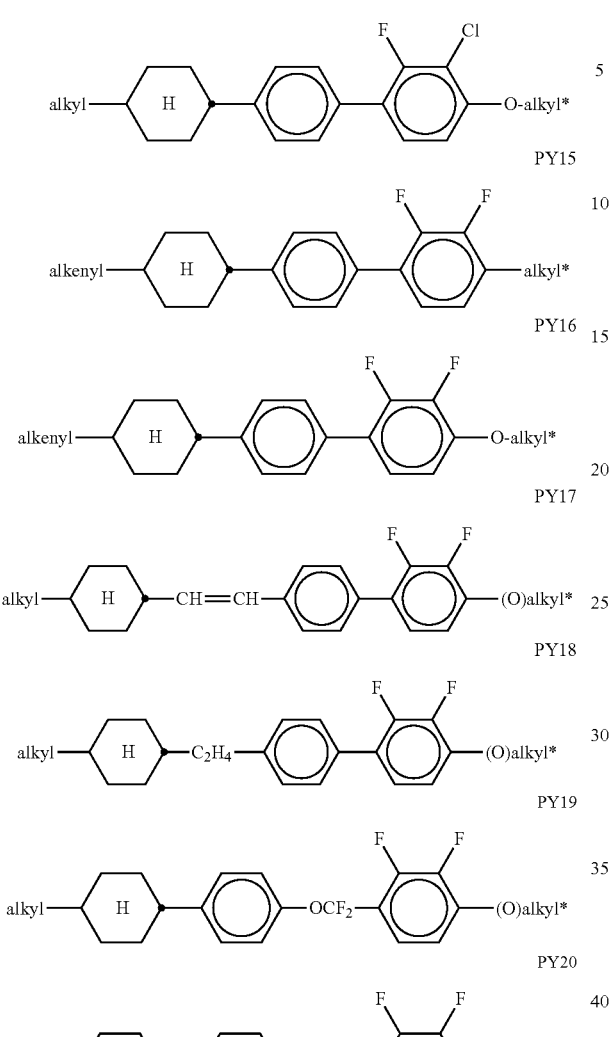

in which alkyl and alkyl* each, independently of one another, denote a straight-chain alkyl radical having 1-6 C atoms, and alkenyl denotes a straight-chain alkenyl radical having 2-6 C atoms, and (O) denotes an oxygen atom or a single bond. Alkenyl preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

b) LC medium which additionally comprises one or more compounds of the following formula:

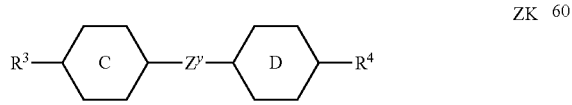

in which the individual radicals have the following meanings:

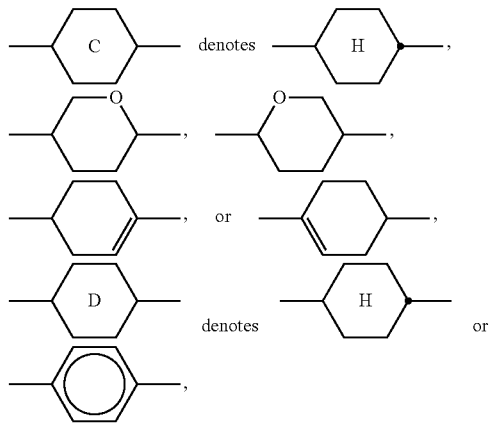

$R^3$ and $R^4$ each, independently of one another, denote alkyl having 1 to 12 C atoms, in which, in addition, one or two non-adjacent $CH_2$ groups may be replaced by $-O-$, $-CH=CH-$, $-CO-$, $-O-CO-$ or $-CO-O-$ in such a way that O atoms are not linked directly to one another, $Z^y$ denotes $-CH_2CH_2-$, $-CH=CH-$, $-CF_2O-$, $-OCF_2-$, $-CH_2O-$, $-OCH_2-$, $-CO-O-$, $-O-CO-$, $-C_2F_4-$, $-CF=CF-$, $-CH=CH-CH_2O-$ or a single bond, preferably a single bond.

The compounds of the formula ZK are preferably selected from the group consisting of the following sub-formulae:

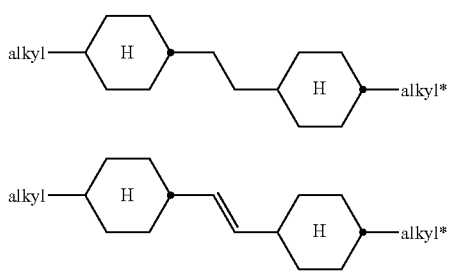

ZK9

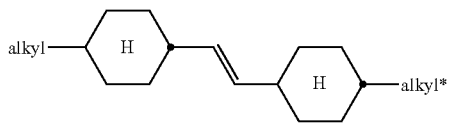

ZK10 in which alkyl and alkyl* each, independently of one another, denote a straight-chain alkyl radical having 1-6 C atoms, and alkenyl denotes a straight-chain alkenyl radical having 2-6 C atoms. Alkenyl preferably denotes CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

c) LC medium which additionally comprises one or more compounds of the following formula:

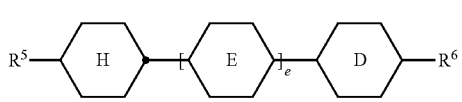

DK in which the individual radicals on each occurrence, identically or differently, have the following meanings:

R$^5$ and R$^6$ each, independently of one another, have one of the meanings indicated above for R$^1$,

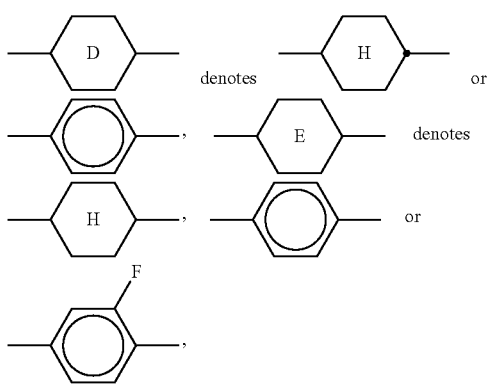

and e denotes 1 or 2.

The compounds of the formula DK are preferably selected from the group consisting of the following sub-formulae:

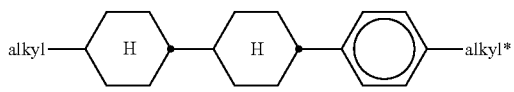

DK1

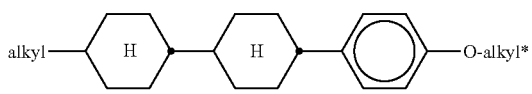

DK2

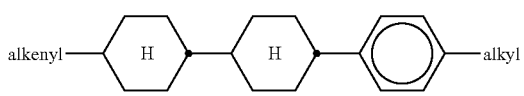

DK3

DK4

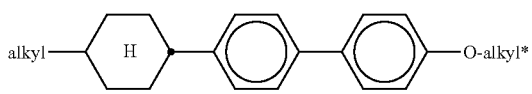

DK5

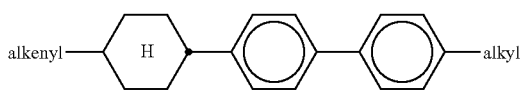

DK6

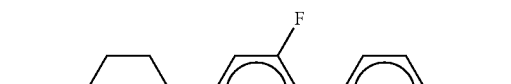

DK7

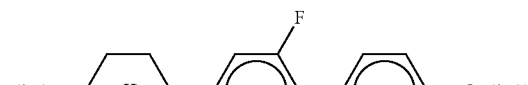

DK8

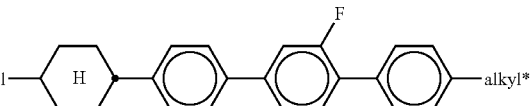

DK9

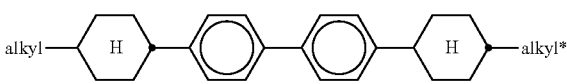

DK10

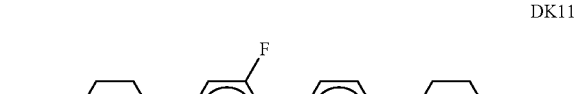

DK11 in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote CH$_2$=CH—, CH$_2$=CHCH$_2$CH$_2$—, CH$_3$—CH=CH—, CH$_3$—CH$_2$—CH=CH—, CH$_3$—(CH$_2$)$_2$—CH=CH—, CH$_3$—(CH$_2$)$_3$—CH=CH— or CH$_3$—CH=CH—(CH$_2$)$_2$—.

d) LC medium which additionally comprises one or more compounds of the following formula:

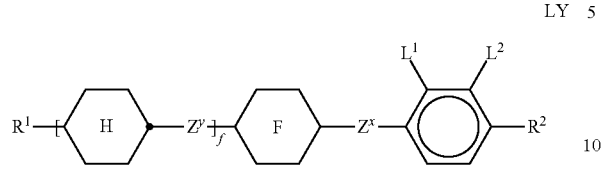

LY in which the individual radicals have the following meanings:

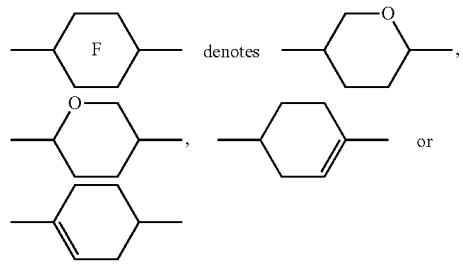

f denotes 0 or 1,
R$^1$ and R$^2$ each, independently of one another, denote alkyl having 1 to 12 C atoms, where, in addition, one or two non-adjacent CH$_2$ groups may be replaced by —O—, —CH=CH—, —CO—, —OCO— or —COO— in such a way that O atoms are not linked directly to one another,
Z$^x$ and Z$^y$ each, independently of one another, denote —CH$_2$CH$_2$—, —CH=CH—, —CF$_2$O—, —OCF$_2$—, —CH$_2$O—, —OCH$_2$—, —CO—O—, —O—CO—, —C$_2$F$_4$—, —CF=CF—, —CH=CH—CH$_2$O— or a single bond, preferably a single bond,
L$^1$ and L$^2$ each, independently of one another, denote F, Cl, OCF$_3$, CF$_3$, CH$_3$, CH$_2$F, CHF$_2$.

Preferably, both radicals L$^1$ and L$^2$ denote F or one of the radicals L$^1$ and L$^2$ denotes F and the other denotes Cl.

The compounds of the formula LY are preferably selected from the group consisting of the following sub-formulae:

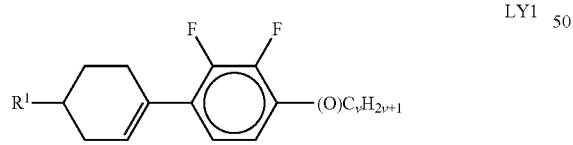
LY1

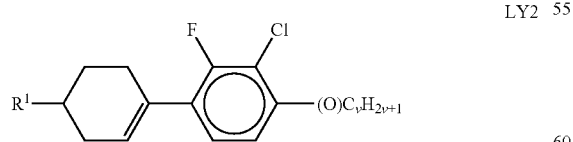
LY2

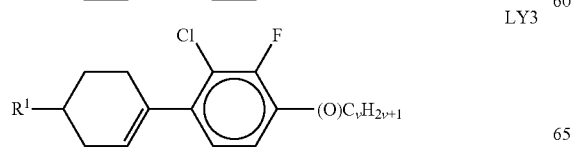
LY3

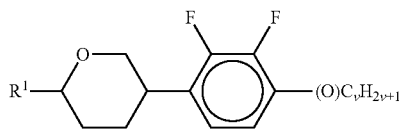
LY4

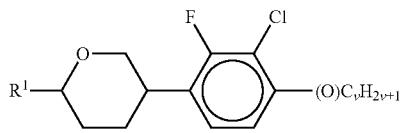
LY5

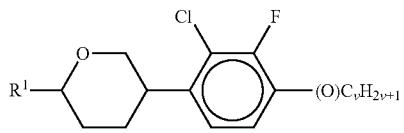
LY6

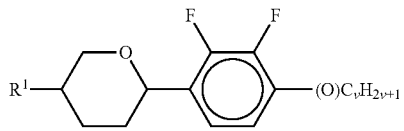
LY7

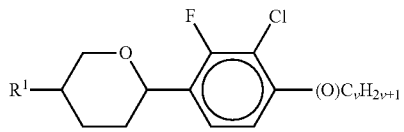
LY8

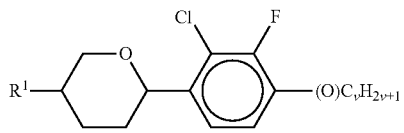
LY9

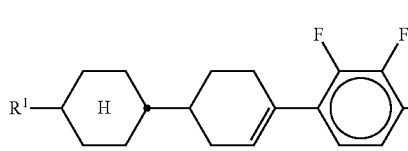
LY10

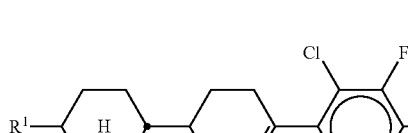
LY11

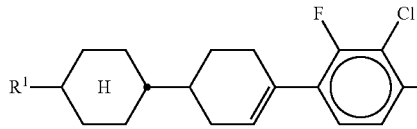
LY12

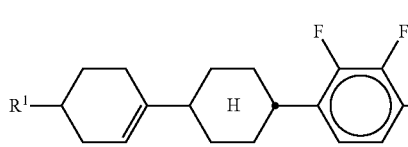
LY13

-continued

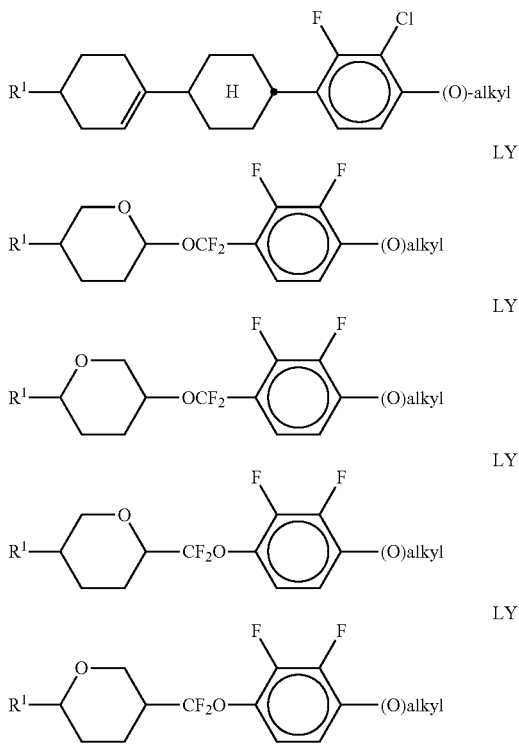

LY14
LY15
LY16
LY17
LY18 in which R¹ has the meaning indicated above, alkyl denotes a straight-chain alkyl radical having 1-6 C atoms, (O) denotes an oxygen atom or a single bond, and v denotes an integer from 1 to 6. R¹ preferably denotes straight-chain alkyl having 1 to 6 C atoms or straight-chain alkenyl having 2 to 6 C atoms, in particular $CH_3$, $C_2H_5$, n-$C_3H_7$, n-$C_4H_9$, n-$C_5H_{11}$, $CH_2$=CH—, $CH_2$=CHCH$_2$CH$_2$—, $CH_3$—CH=CH—, $CH_3$—$CH_2$—CH=CH—, $CH_3$—$(CH_2)_2$—CH=CH—, $CH_3$—$(CH_2)_3$—CH=CH— or $CH_3$—CH=CH—$(CH_2)_2$—.

e) LC medium which additionally comprises one or more compounds selected from the group consisting of the following formulae:

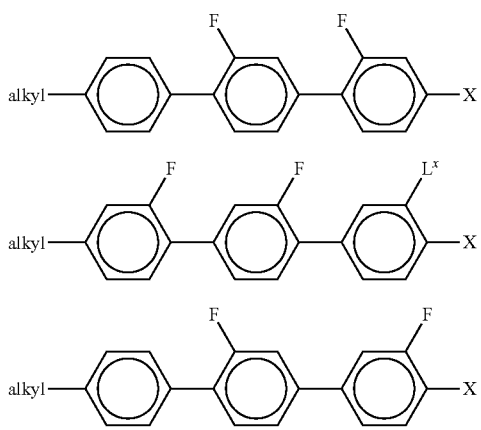

G1
G2
G3

-continued

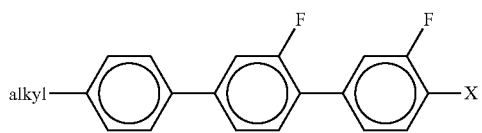

G4 in which alkyl denotes $C_{1-6}$-alkyl, $L^x$ denotes H or F, and X denotes F, Cl, $OCF_3$, $OCHF_2$ or OCH=$CF_2$. Particular preference is given to compounds of the formula G1 in which X denotes F.

f) LC medium which additionally comprises one or more compounds selected from the group consisting of the following formulae:

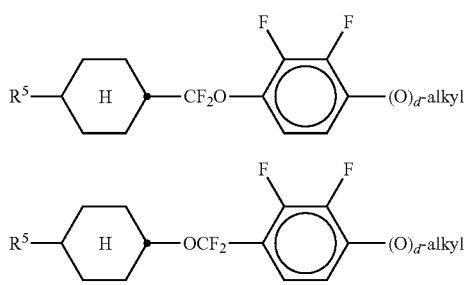

Y1
Y2

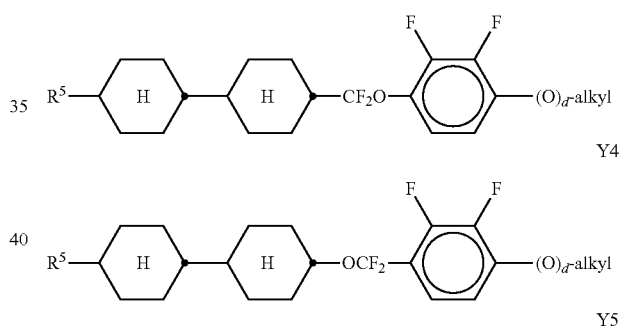

Y3
Y4

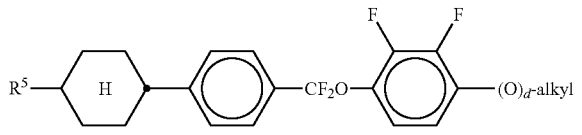

Y5

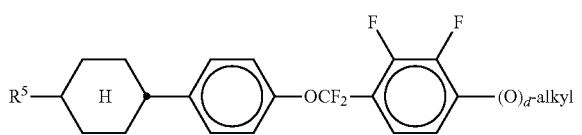

Y6

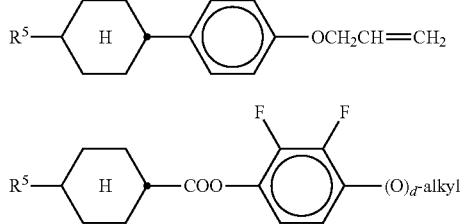

Y7
Y8

-continued

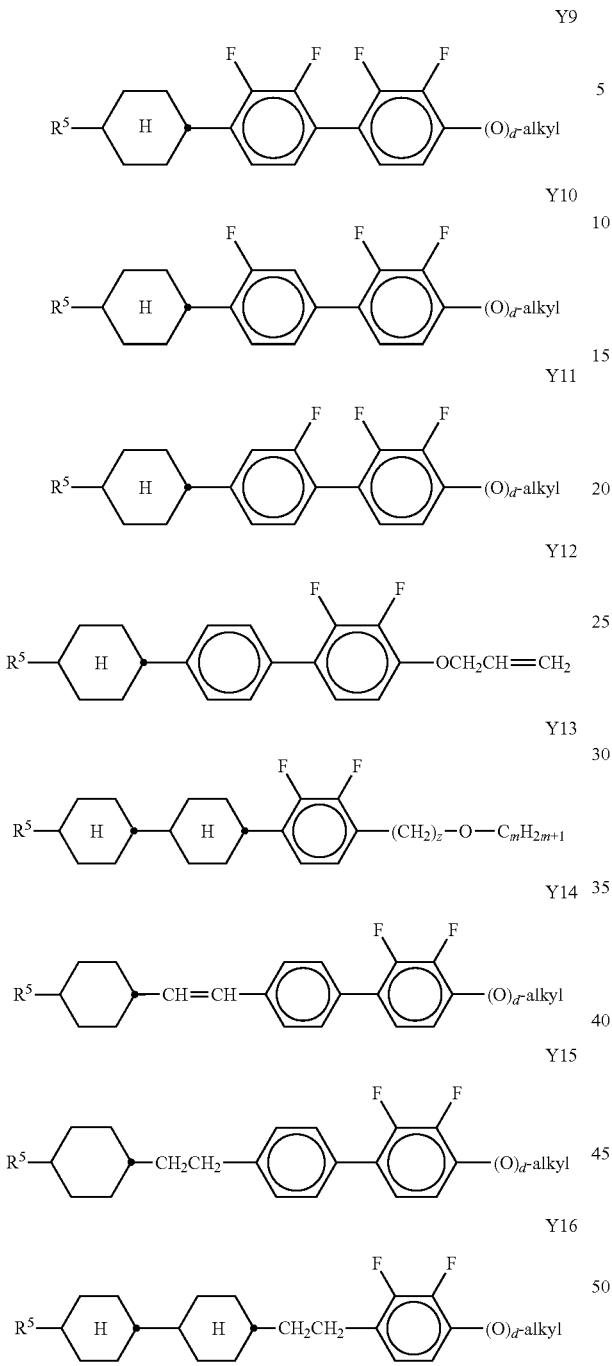

in which $R^5$ has one of the meanings indicated above for $R^1$, alkyl denotes $C_{1-6}$-alkyl, d denotes 0 or 1, and z and m each, independently of one another, denote an integer from 1 to 6. $R^5$ in these compounds is particularly preferably $C_{1-6}$-alkyl or -alkoxy or $C_{2-6}$-alkenyl, d is preferably 1. The LC medium according to the invention preferably comprises one or more compounds of the abovementioned formulae in amounts of ≥5% by weight.

g) LC medium which additionally comprises one or more biphenyl compounds selected from the group consisting of the following formulae:

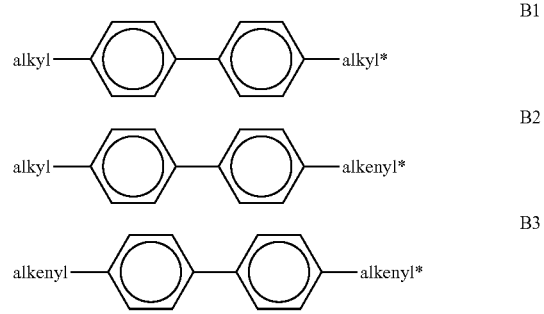

in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

The proportion of the biphenyls of the formulae B1 to B3 in the LC mixture is preferably at least 3% by weight, in particular ≥5% by weight.

The compounds of the formula B2 are particularly preferred.

The compounds of the formulae B1 to B3 are preferably selected from the group consisting of the following sub-formulae:

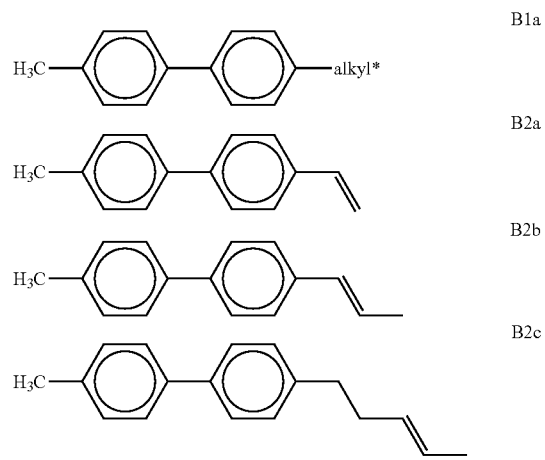

in which alkyl* denotes an alkyl radical having 1-6 C atoms. The medium according to the invention particularly preferably comprises one or more compounds of the formulae B1a and/or B2c.

h) LC medium which additionally comprises one or more terphenyl compounds of the following formula:

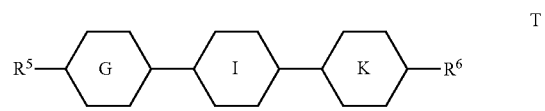

in which $R^5$ and $R^6$ each, independently of one another, have one of the meanings indicated above for $R^1$, and

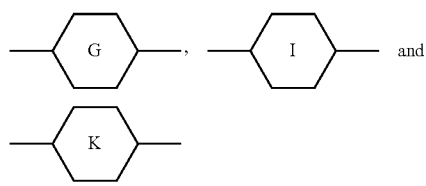
each, independently of one another, denote
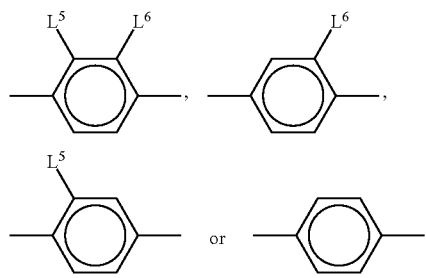
in which $L^5$ denotes F or Cl, preferably F, and $L^6$ denotes F, Cl, $OCF_3$, $CF_3$, $CH_3$, $CH_2F$ or $CHF_2$, preferably F.
The compounds of the formula T are preferably selected from the group consisting of the following sub-formulae:
T1
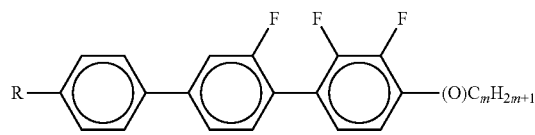
T2
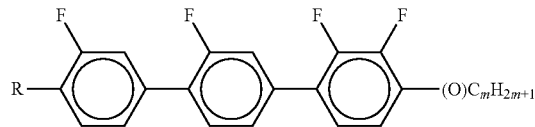
T3
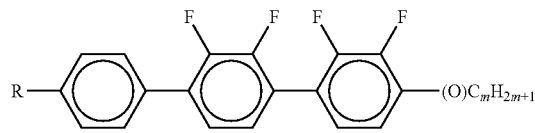
T4
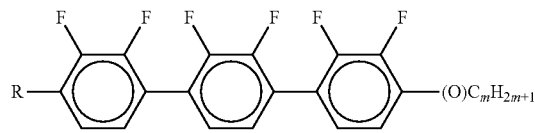
T5
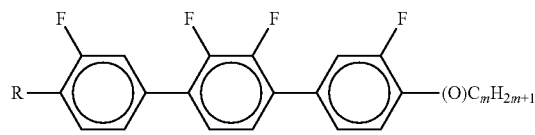
T6
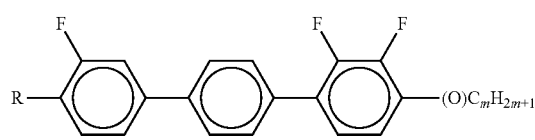
T7
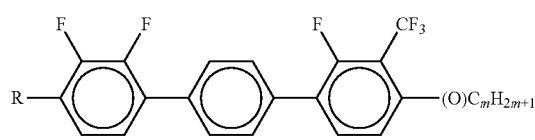
T8
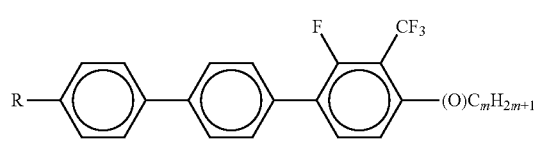
T9
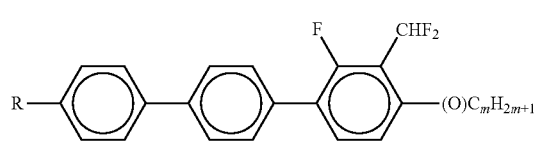
T10
T11
T12
T13
T14
T15
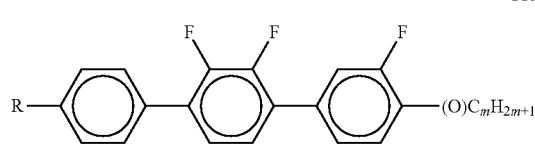

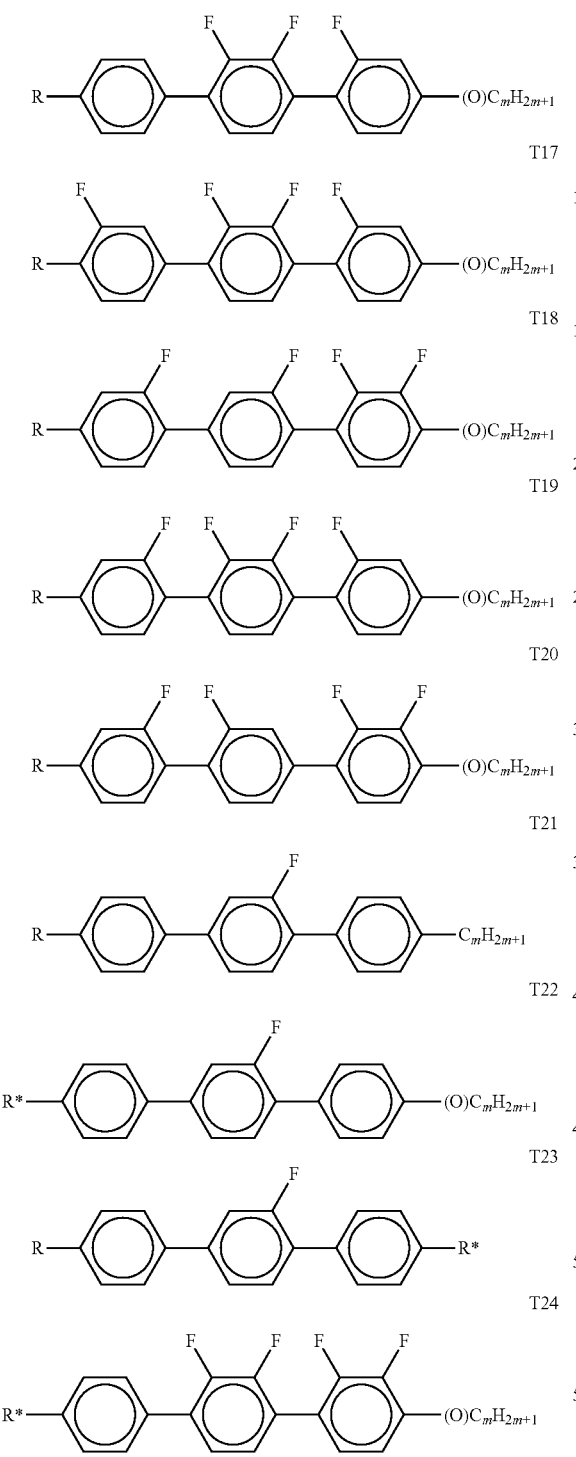

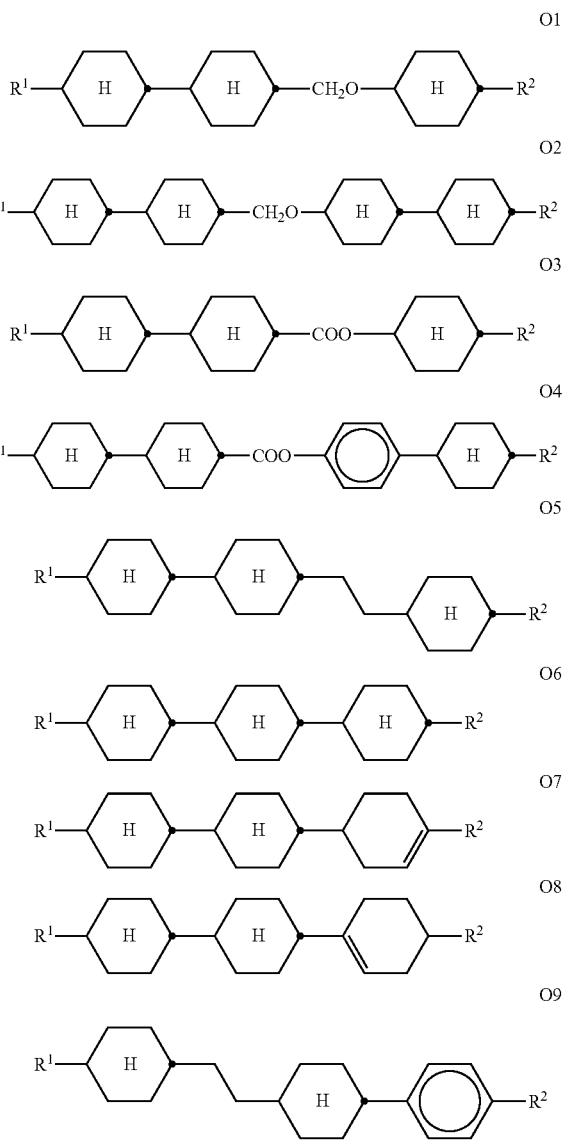

in which R denotes a straight-chain alkyl or alkoxy radical having 1-7 C atoms, R* denotes a straight-chain alkenyl radical having 2-7 C atoms, (O) denotes an oxygen atom or a single bond, and m denotes an integer from 1 to 6. R* preferably denotes $CH_2=CH-$, $CH_2=CHCH_2CH_2-$, $CH_3-CH=CH-$, $CH_3-CH_2-CH=CH-$, $CH_3-(CH_2)_2-CH=CH-$, $CH_3-(CH_2)_3-CH=CH-$ or $CH_3-CH=CH-(CH_2)_2-$.

R preferably denotes methyl, ethyl, propyl, butyl, pentyl, hexyl, methoxy, ethoxy, propoxy, butoxy or pentoxy.

The LC medium according to the invention preferably comprises the terphenyls of the formula T and the preferred sub-formulae thereof in an amount of 0.5-30% by weight, in particular 1-20% by weight.

Particular preference is given to compounds of the formulae T1, T2, T3 and T21. In these compounds, R preferably denotes alkyl, furthermore alkoxy, each having 1-5 C atoms.

The terphenyls are preferably employed in mixtures according to the invention if the Δn value of the mixture is to be ≥0.1. Preferred mixtures comprise 2-20% by weight of one or more terphenyl compounds of the formula T, preferably selected from the group of compounds T1 to T22.

i) LC medium which additionally comprises one or more compounds selected from the group consisting of the following formulae:

-continued

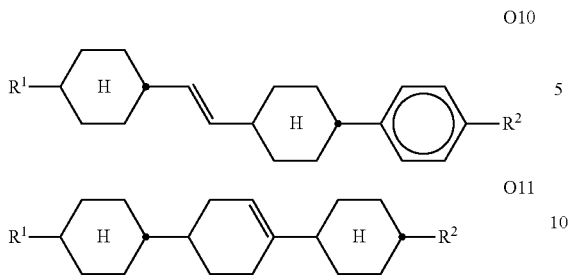

in which R¹ and R² have the meanings indicated above and preferably each, independently of one another, denote straight-chain alkyl having 1 to 6 C atoms or straight-chain alkenyl having 2 to 6 C atoms.

Preferred media comprise one or more compounds selected from the formulae O1, O3 and O4.

k) LC medium which additionally comprises one or more compounds of the following formula:

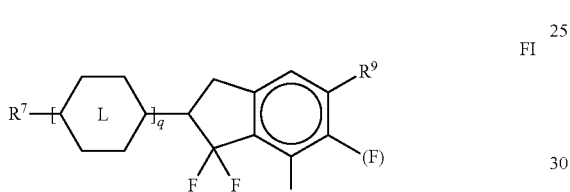

in which 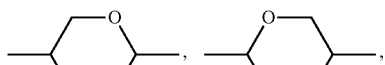 denotes ,

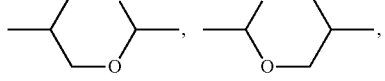

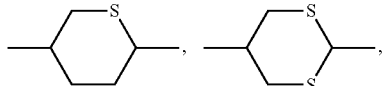

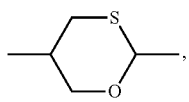

R⁹ denotes H, CH₃, C₂H₅ or n-C₃H₇, (F) denotes an optional fluorine substituent, and q denotes 1, 2 or 3, and R⁷ has one of the meanings indicated for R¹, preferably in amounts of >3% by weight, in particular ≥5% by weight and very particularly preferably 5-30% by weight.

Particularly preferred compounds of the formula FI are selected from the group consisting of the following subformulae:

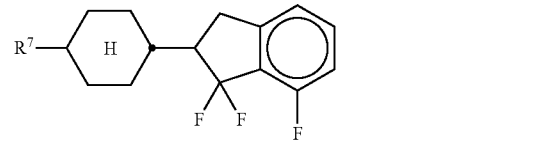

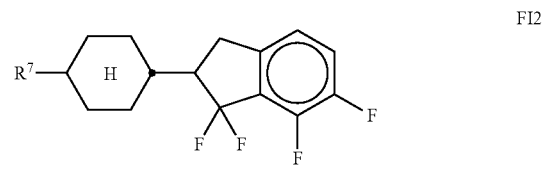

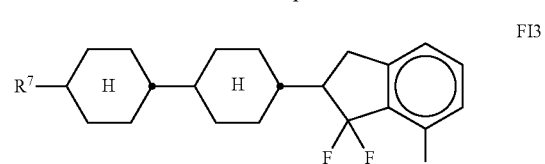

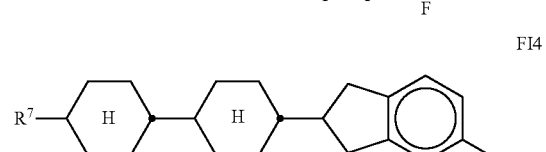

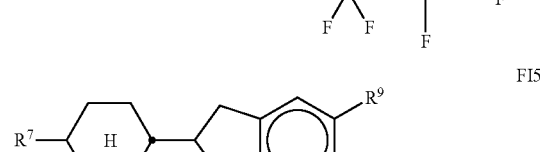

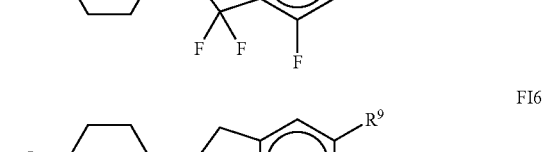

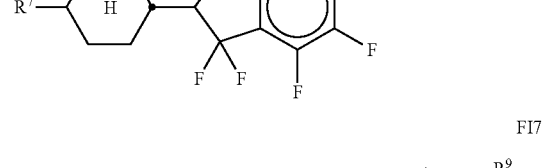

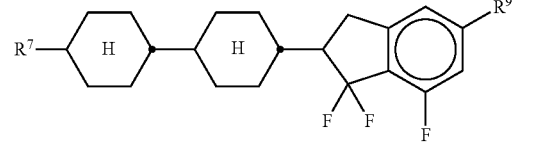

in which R⁷ preferably denotes straight-chain alkyl, and R⁹ denotes CH₃, C₂H₅ or n-C₃H₇. Particular preference is given to the compounds of the formulae FI1, FI2 and FI3.

m) LC medium which additionally comprises one or more compounds selected from the group consisting of the following formulae:

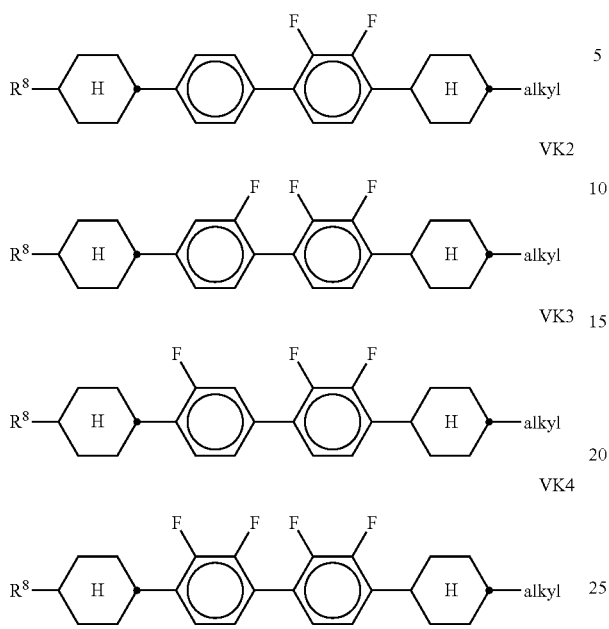

VK1
VK2
VK3
VK4 in which $R^8$ has the meaning indicated for $R^1$, and alkyl denotes a straight-chain alkyl radical having 1-6 C atoms.

n) LC medium which additionally comprises one or more compounds which contain a tetrahydronaphthyl or naphthyl unit, such as, for example, the compounds selected from the group consisting of the following formulae:

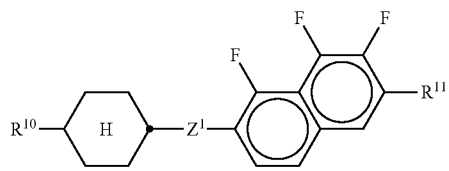

N1

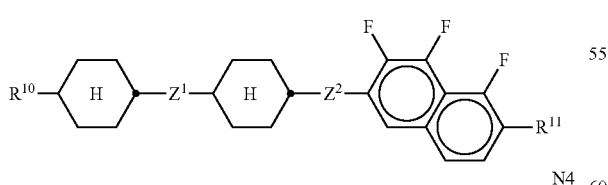

N2

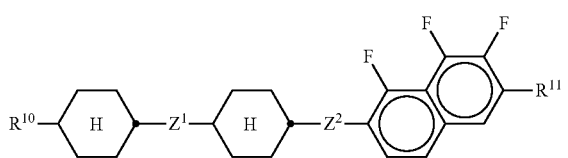

N3

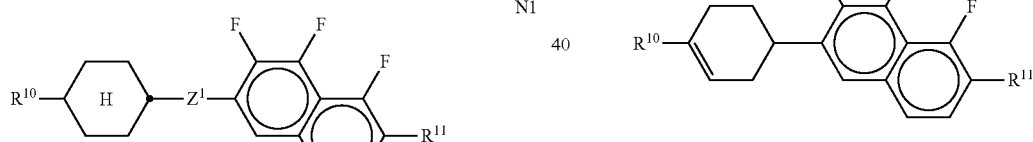

N4

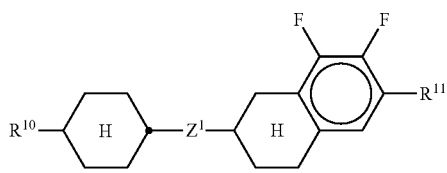

N5

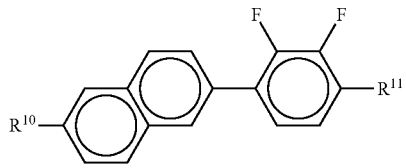

N6

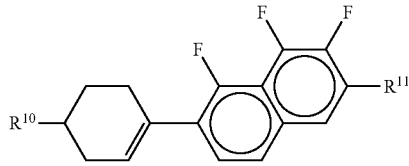

N7

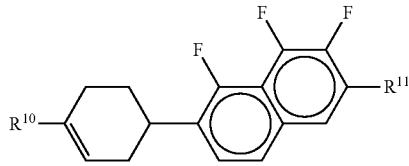

N8

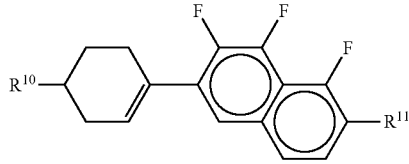

N9

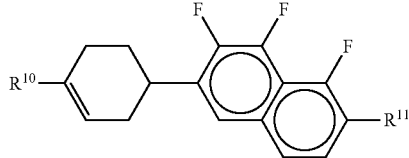

N10 in which $R^{10}$ and $R^{11}$ each, independently of one another, have one of the meanings indicated for $R^1$, preferably denote straight-chain alkyl or alkoxy having 1 to 6 C atoms or straight-chain alkenyl having 2 to 6 C atoms, and $Z^1$ and $Z^2$ each, independently of one another, denote —$C_2H_4$—, —CH=CH—, —$(CH_2)_4$—, —$(CH_2)_3O$—, —$O(CH_2)_3$—, —CH=CH—$CH_2CH_2$—, —$CH_2CH_2CH=CH$—, —$CH_2O$—, —$OCH_2$—, —CO—O—, —O—CO—, —$C_2F_4$—, —CF=CF—, —CF=CH—, —CH=CF—, —$CH_2$— or a single bond.

o) LC medium which additionally comprises one or more difluorodibenzo-chromans and/or chromans of the following formulae:

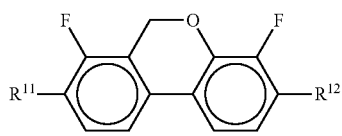

BC

-continued

CR

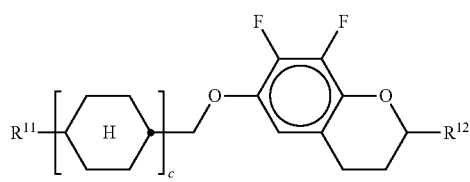

in which R¹¹ and R¹² each, independently of one another, have the meanings indicated above, and c denotes 0 or 1, preferably in amounts of 3 to 20% by weight, in particular in amounts of 3 to 15% by weight.

Particularly preferred compounds of the formulae BC and CR are selected from the group consisting of the following sub-formulae:

BC1

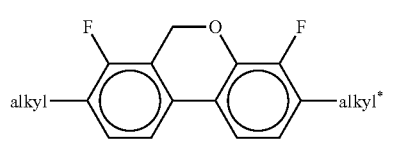

BC2

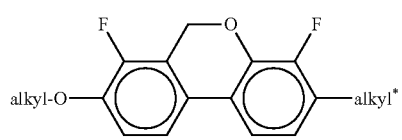

BC3

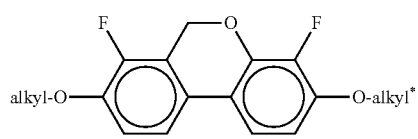

BC4

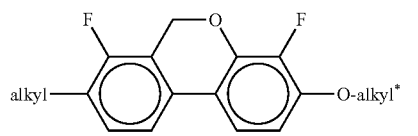

BC5

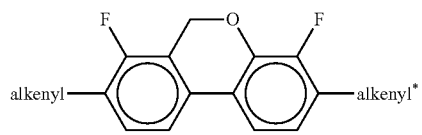

BC6

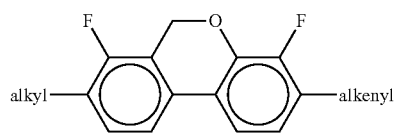

BC7

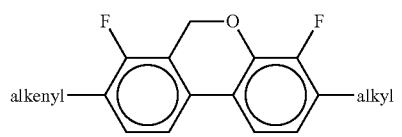

CR1

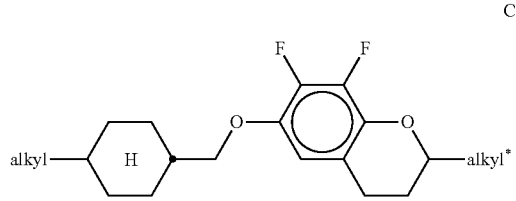

-continued

CR2

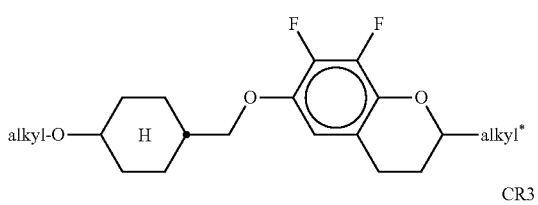

CR3

CR4

CR5 in which alkyl and alkyl* each, independently of one another, denote a straight-chain alkyl radical having 1-6 C atoms, and alkenyl and alkenyl* each, independently of one another, denote a straight-chain alkenyl radical having 2-6 C atoms. Alkenyl and alkenyl* preferably denote CH₂=CH—, CH₂=CHCH₂CH₂—, CH₃—CH=CH—, CH₃—CH₂—CH=CH—, CH₃—(CH₂)₂—CH=CH—, CH₃—(CH₂)₃—CH=CH— or CH₃—CH=CH—(CH₂)₂—.

Very particular preference is given to mixtures comprising one, two or three compounds of the formula BC2.

p) LC medium which additionally comprises one or more fluorinated phenanthrenes and/or dibenzofurans of the following formulae:

PH

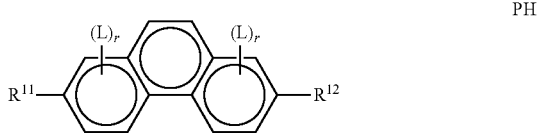

BF

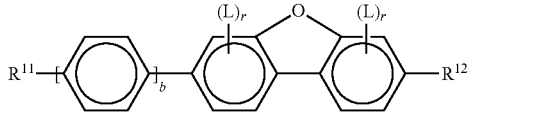

in which R¹¹ and R¹² each, independently of one another, have the meanings indicated above, b denotes 0 or 1, L denotes F, and r denotes 1, 2 or 3.

Particularly preferred compounds of the formulae PH and BF are selected from the group consisting of the following sub-formulae:

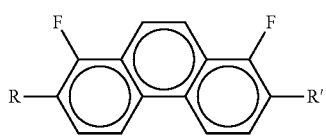
PH1

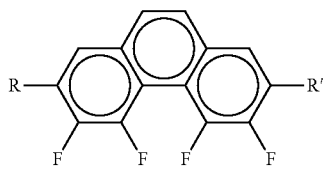
PH2

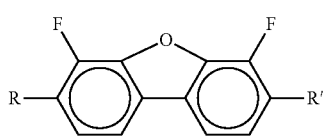
BF1

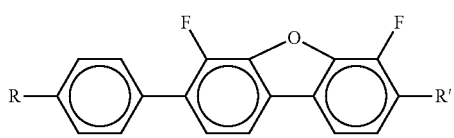
BF2 in which R and R' each, independently of one another, denote a straight-chain alkyl or alkoxy radical having 1-7 C atoms.

q) LC medium which comprises 1 to 8, preferably 1 to 5, compounds of the formulae CY1, CY2, PY1 and/or PY2. The proportion of these compounds in the mixture as a whole is preferably 5 to 60%, particularly preferably 10 to 35%. The content of these individual compounds is preferably in each case 2 to 20%.

r) LC medium which comprises 1 to 8, preferably 1 to 5, compounds of the formulae CY9, CY10, PY9 and/or PY10. The proportion of these compounds in the mixture as a whole is preferably 5 to 60%, particularly preferably 10 to 35%. The content of these individual compounds is preferably in each case 2 to 20%.

s) LC medium which comprises 1 to 10, preferably 1 to 8, compounds of the formula ZK, in particular compounds of the formulae ZK1, ZK2 and/or ZK6. The proportion of these compounds in the mixture as a whole is preferably 3 to 45%, particularly preferably 5 to 25%. The content of these individual compounds is preferably in each case 2 to 20%.

t) LC medium in which the proportion of compounds of the formulae CY, PY and ZK in the mixture as a whole is greater than 70%, preferably greater than 80%.

u) PSA-VA display in which the pretilt angle is preferably ≦86°.

Particularly preferred LC media for use in PSA-OCB, PSA-TN, PSA-IPS or PSA-FFS displays are indicated below:

a) LC medium which comprises one or more compounds selected from the group consisting of the following formulae:

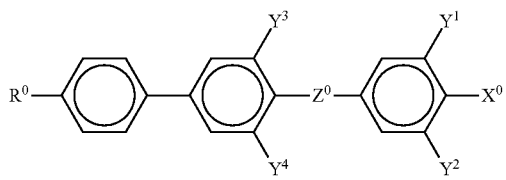
AA

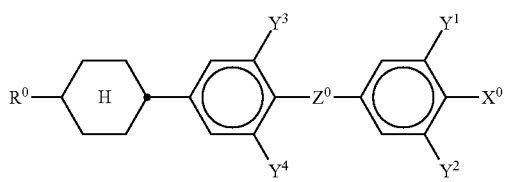
BB

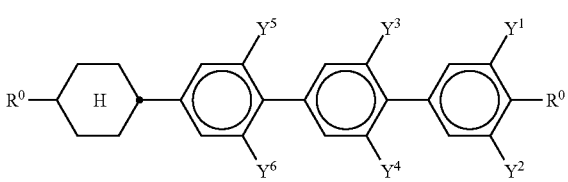
CC in which $R^0$ on each occurrence, identically or differently, denotes n-alkyl, alkoxy, oxaalkyl, fluoroalkyl or alkenyl, each having up to 9 C atoms, $X^0$ denotes F, Cl or in each case halogenated alkyl, alkenyl, alkenyloxy or alkoxy, each having up to 6 C atoms, $Z^0$ denotes —$CF_2O$— or a single bond, $Y^{1-6}$ each, independently of one another, denote H or F.

$X^0$ is preferably F, Cl, $CF_3$, $CHF_2$, $OCF_3$, $OCHF_2$, OCFHCF$_3$, OCFHCHF$_2$, $OCF_2CH_3$, $OCF_2CHF_2$, $OCF_2CF_2CHF_2$, $OCFHCF_2CF_3$, $OCFHCF_2CHF_2$, $OCF_2CF_2CF_3$, $OCF_2CF_2CClF_2$, $OCClFCF_2CF_3$ or CH=$CF_2$, particularly preferably F or $OCF_3$.

The compounds of the formula AA are preferably selected from the group consisting of the following sub-formulae:

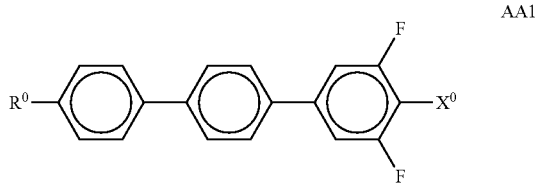
AA1

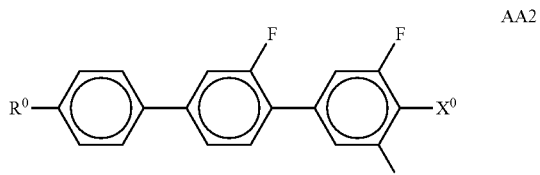
AA2

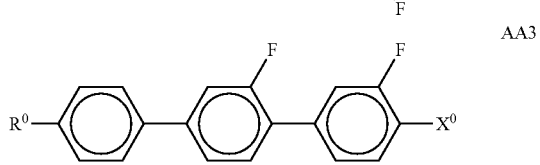
AA3

AA4
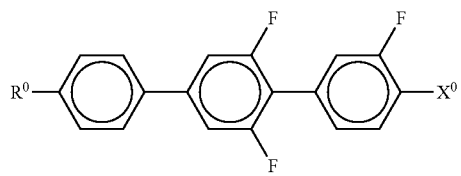

AA5
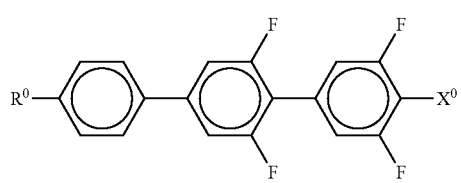

AA6
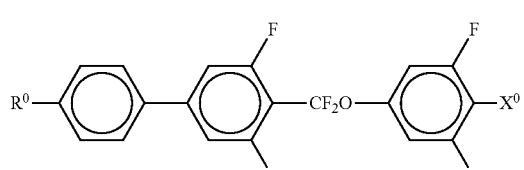

AA7
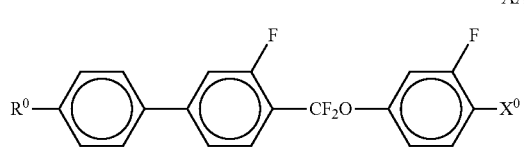

AA8
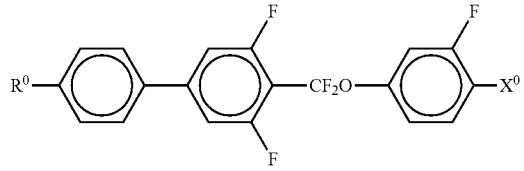

AA9
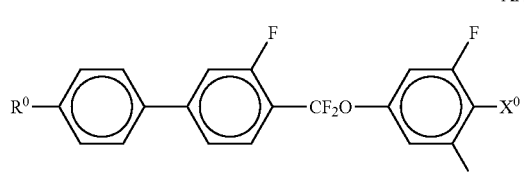

in which $R^0$ and $X^0$ have the meanings indicated above, and $X^0$ preferably denotes F. Particular preference is given to compounds of the formulae AA2 and AA6.

The compounds of the formula BB are preferably selected from the group consisting of the following sub-formulae:

BB1
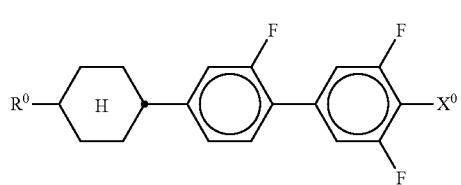

BB2
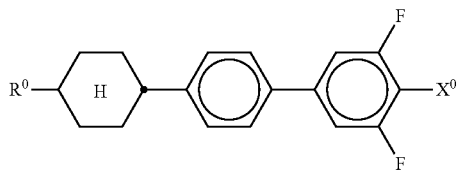

BB3

BB4
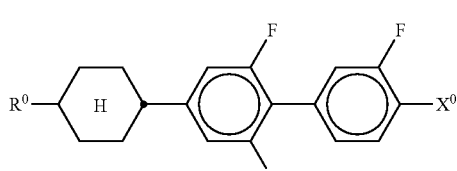

BB5
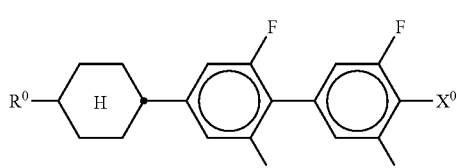

BB6
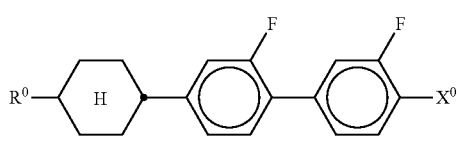

in which $R^0$ and $X^0$ have the meanings indicated above, and $X^0$ preferably denotes F. Particular preference is given to compounds of the formulae BB1, BB2 and BB5.

The compounds of the formula CC are preferably selected from the following sub-formula:

CC1
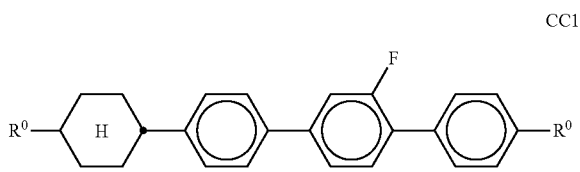

in which $R^0$ on each occurrence, identically or differently, has the meaning indicated above and preferably denotes alkyl having 1 to 6 C atoms.

The combination of compounds of the preferred embodiments a)-y) mentioned above with the polymerised compounds described above causes low threshold voltages, low rotational viscosities and very good low-temperature stabilities in the LC media according to the invention at the same time as constantly high clearing points and high HR values, and allows the rapid establishment of a particularly low pretilt angle in PSA displays. In particular, the LC media exhibit significantly shortened response times, in particular also the grey-shade response times, in PSA displays compared with the media from the prior art.

The liquid-crystal mixture preferably has a nematic phase range of at least 80 K, particularly preferably at least 100 K, and a rotational viscosity of not greater than 250 mPa·s, preferably not greater than 200 mPa·s, at 20° C. LC media according to the invention for use in displays of the PSA-VA type have negative dielectric anisotropy Δ∈, preferably from about −0.5 to −10, in particular from about −2.5 to −7.5 at 20° C. and 1 kHz.

In VA-type displays according to the invention, the molecules in the layer of the LC medium in the switched-off state are aligned perpendicular to the electrode surfaces (homeotropically) or have a tilted homeotropic alignment. On application of an electrical voltage to the electrodes, a realignment of the LC molecules takes place with the longitudinal molecular axes parallel to the electrode surfaces.

In OCB-type displays according to the invention, the molecules in the layer of the LC medium have a "bend" alignment. On application of an electrical voltage, re-alignment of the LC molecules takes place with the longitudinal molecular axes perpendicular to the electrode surfaces.

LC media according to the invention for use in displays of the PSA-OCB type preferably have positive dielectric anisotropy Δ∈, preferably from about +4 to +17 at 20° C. and 1 kHz.

The birefringence Δn in LC media according to the invention for use in displays of the VA type is preferably less than 0.16, particularly preferably between 0.06 and 0.14, in particular between 0.07 and 0.12.

The birefringence Δn in LC media according to the invention for use in displays of the OCB type is preferably between 0.14 and 0.22, in particular between 0.16 and 0.22.

The birefringence Δn in LC media according to the invention for use in displays of the PSA-TN, PSA-IPS or PSA-FFS type is preferably between 0.07 and 0.15, in particular between 0.08 and 0.13. The dielectric anisotropy of these media is preferably between +2 and +17, in particular between +3 and +15.

The LC media according to the invention may also comprise further additives known to the person skilled in the art and described in the literature, such as, for example, polymerisation initiators, inhibitors, stabilisers, surface-active substances or chiral dopants. These may be polymerisable or unpolymerisable. Polymerisable additives are accordingly ascribed to the polymerisable component. Unpolymerisable additives are accordingly ascribed to the liquid-crystalline component.

The LC media may, for example, comprise one or more chiral dopants, preferably those selected from the group consisting of compounds from Table B below.

Furthermore, it is possible to add to the LC media, for example, 0 to 15% by weight of pleochroic dyes, furthermore nanoparticles, conductive salts, preferably ethyldimethyldodecylammonium 4-hexoxybenzoate, tetrabutylammonium tetraphenylborate or complex salts of crown ethers (cf., for example, Haller et al., Mol. Cryst. Liq. Cryst. 24, 249-258 (1973)), for improving the conductivity, or substances for modifying the dielectric anisotropy, the viscosity and/or the alignment of the nematic phases. Substances of this type are described, for example, in DE-A 22 09 127, 22 40 864, 23 21 632, 23 38 281, 24 50 088, 26 37 430 and 28 53 728.

The individual components of the preferred embodiments a)-z) of the LC media according to the invention are either known or methods for the preparation thereof can readily be derived from the prior art by the person skilled in the relevant art, since they are based on standard methods described in the literature. Corresponding compounds of the formula CY are described, for example, in EP-A-0 364 538. Corresponding compounds of the formula ZK are described, for example, in DE-A-26 36 684 and DE-A-33 21 373.

The LC media which can be used in accordance with the invention are prepared in a manner conventional per se, for example by mixing one or more of the above-mentioned compounds with one or more polymerisable compounds as defined above, and optionally with further liquid-crystalline compounds and/or additives. In general, the desired amount of the components used in lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing. The invention furthermore relates to the process for the preparation of the LC media according to the invention.

It goes without saying to the person skilled in the art that the LC media according to the invention may also comprise compounds in which, for example, H, N, O, Cl, F have been replaced by the corresponding isotopes.

The structure of the PSA displays according to the invention corresponds to the usual geometry for PSA displays, as described in the prior art cited at the outset. Geometries without protrusions are preferred, in particular those in which, in addition, the electrode on the colour filter side is unstructured and only the electrode on the TFT side has slots. Particularly suitable and preferred electrode structures for PSA-VA displays are described, for example, in US 2006/0066793 A1.

The following examples explain the present invention without restricting it. However, they show the person skilled in the art preferred mixture concepts with compounds preferably to be employed and the respective concentrations thereof and combinations thereof with one another. In addition, the examples illustrate which properties and property combinations are accessible.

The following abbreviations are used:

(n, m, z: in each case, independently of one another, 1, 2, 3, 4, 5 or 6)

TABLE A

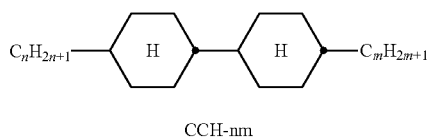

CCH-nm

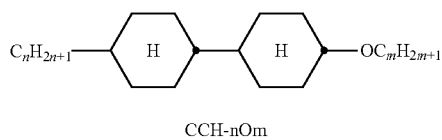

CCH-nOm

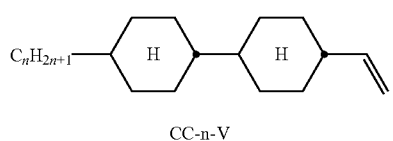

CC-n-V

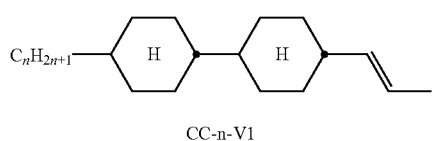

CC-n-V1

TABLE A-continued
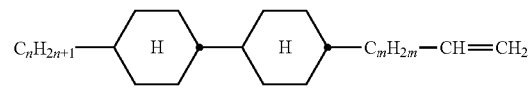
CC-n-mV
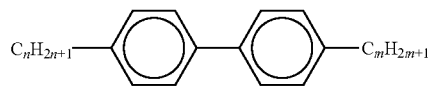
PP-n-m
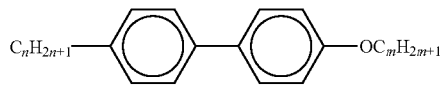
PP-n-Om
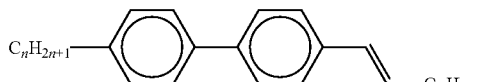
PP-n-Vm
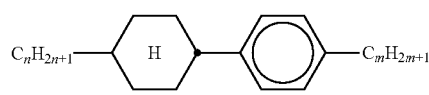
PCH-nm
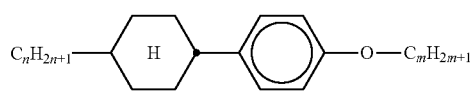
PCH-nOm
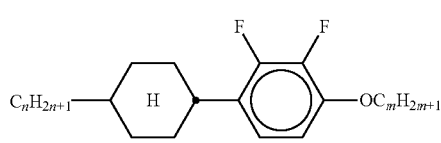
CY-n-Om
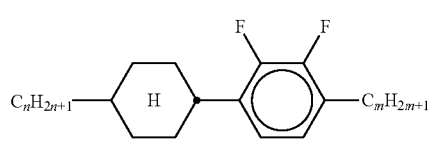
CY-n-m
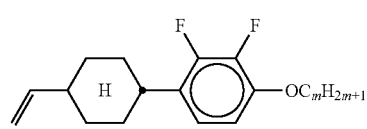
CY-V-Om
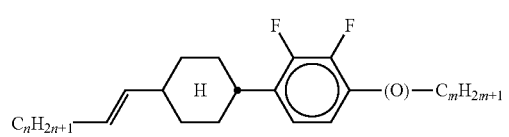
CY-nV-(O)m
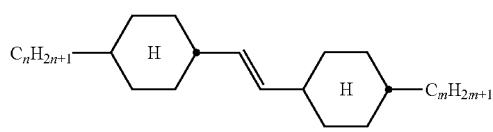
CVC-n-m
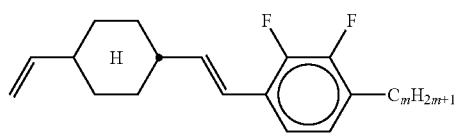
CVY-V-m
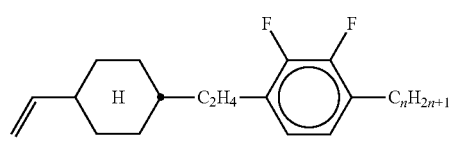
CEY-V-m
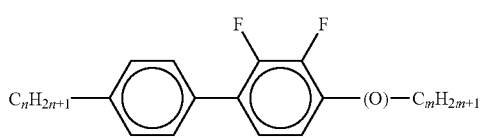
PY-n-(O)m
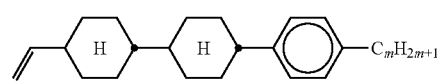
CCP-V-m
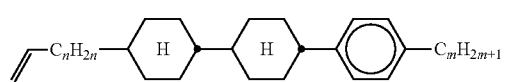
CCP-Vn-m
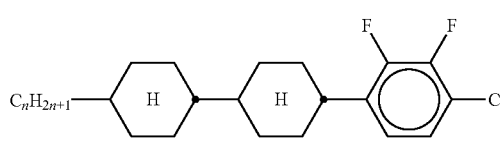
CCY-n-m
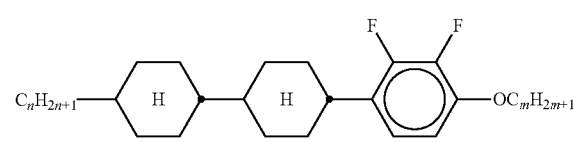
CCY-n-Om TABLE A-continued
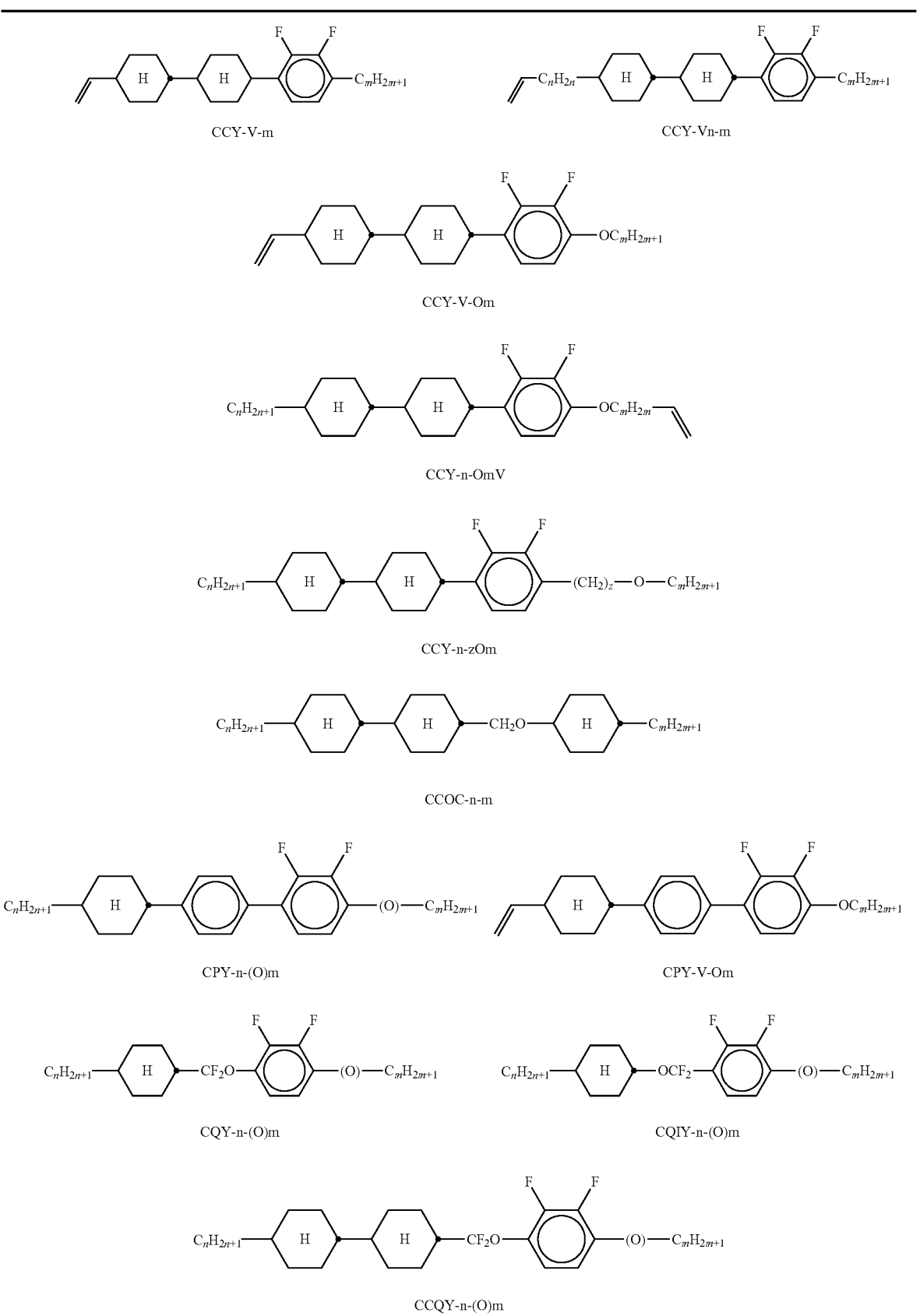

TABLE A-continued
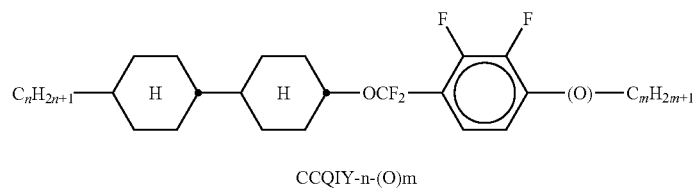
CCQIY-n-(O)m
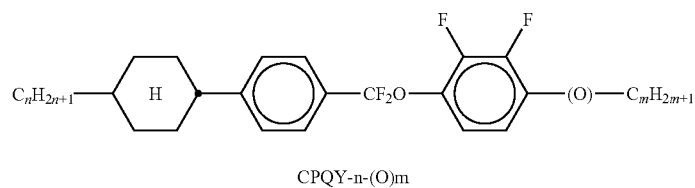
CPQY-n-(O)m
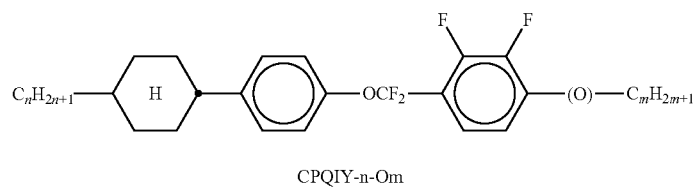
CPQIY-n-Om
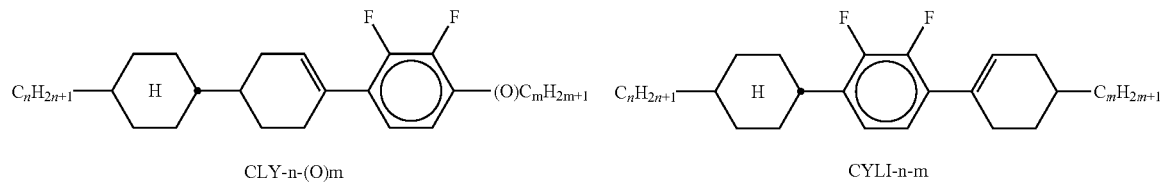
CLY-n-(O)m          CYLI-n-m
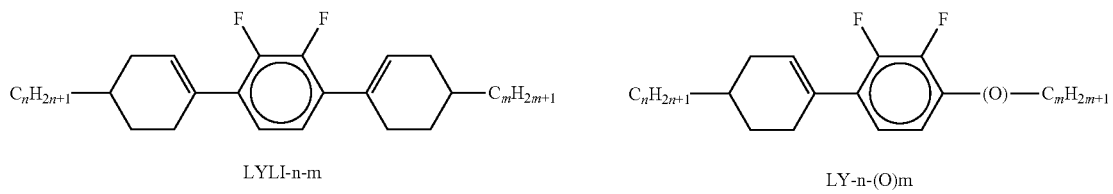
LYLI-n-m          LY-n-(O)m
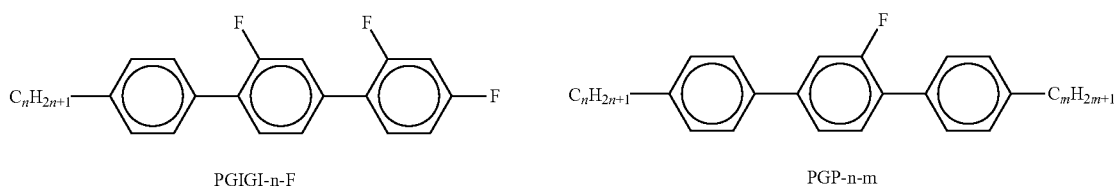
PGIGI-n-F          PGP-n-m
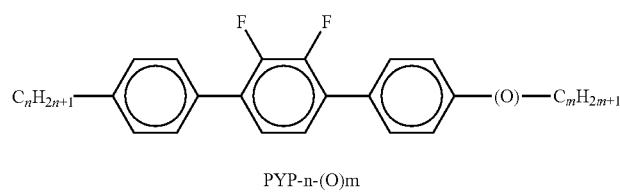
PYP-n-(O)m
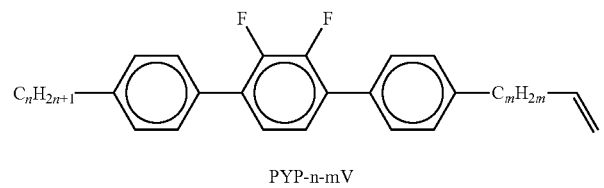
PYP-n-mV TABLE A-continued
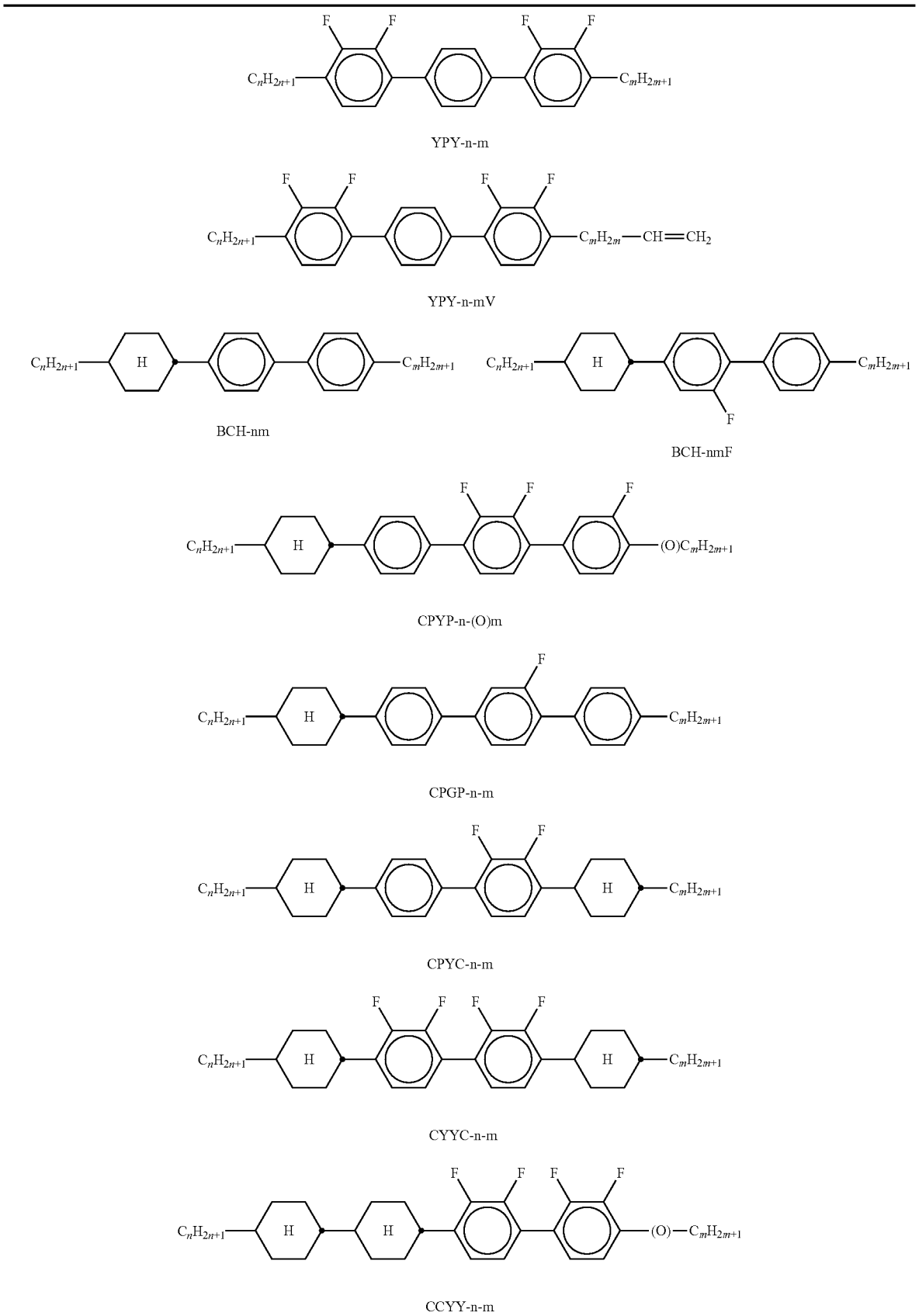

TABLE A-continued
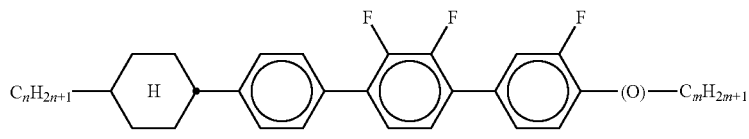
CPYG-n-(O)m
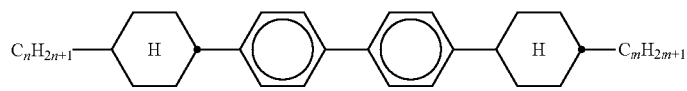
CBC-nm
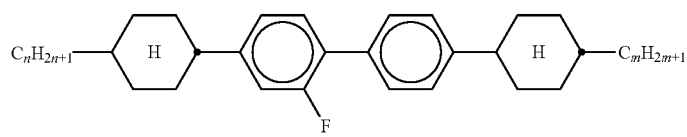
CBC-nmF
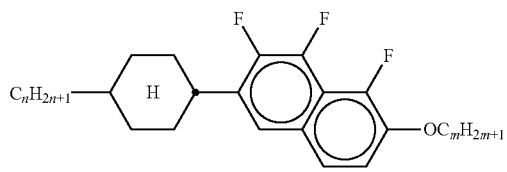
CNap-n-Om
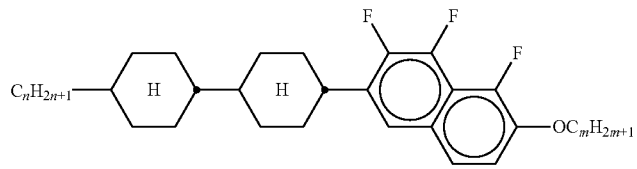
CCNap-n-Om
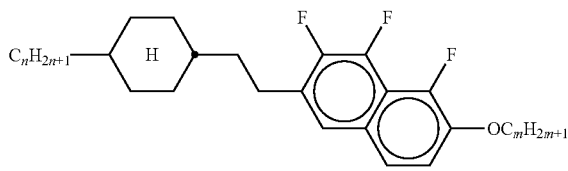
CENap-n-Om
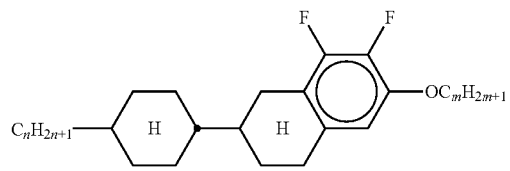
CTNap-n-Om
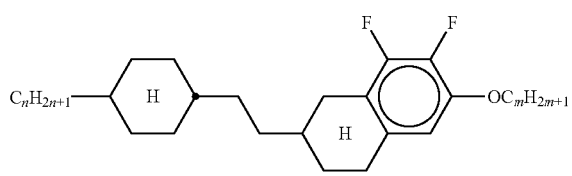
CETNap-n-Om TABLE A-continued
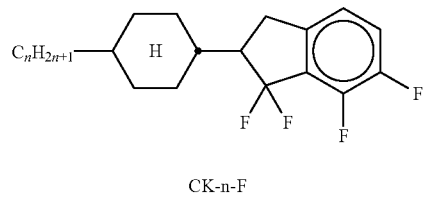
CK-n-F
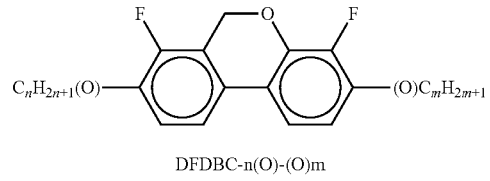
DFDBC-n(O)-(O)m
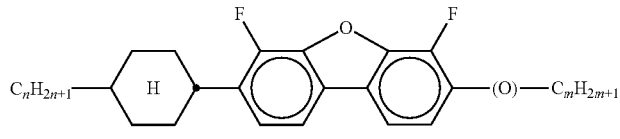
C-DFDBF-n-(O)m
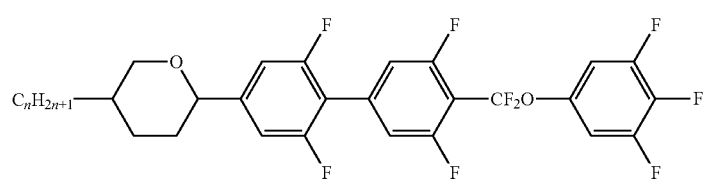
AUUQU-n-F
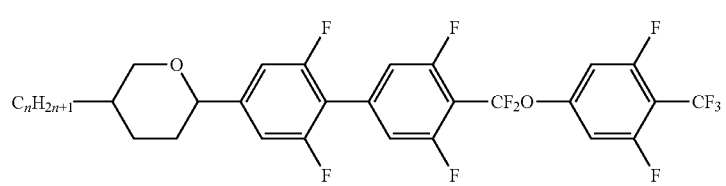
AUUQU-n-T
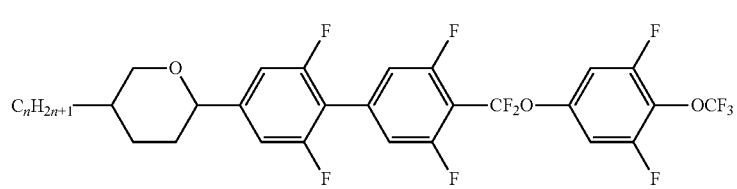
AUUQU-n-OT
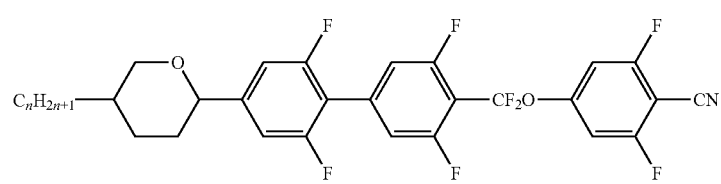
AUUQU-n-N
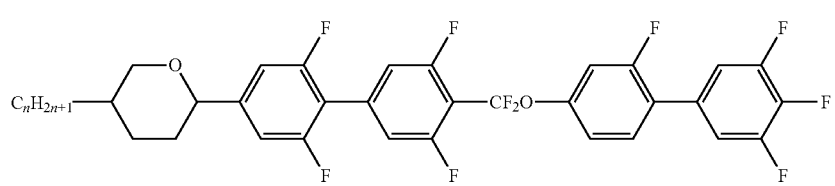
AUUQGU-n-F TABLE A-continued
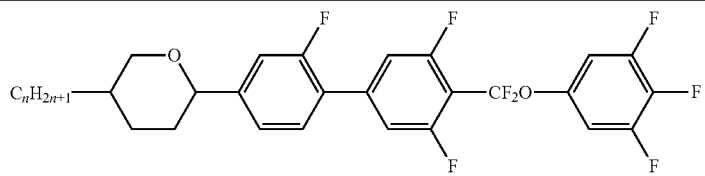
AGUQU-n-F
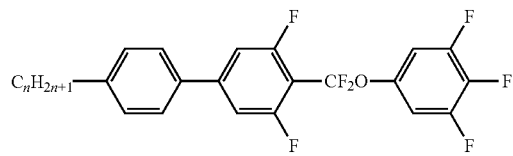
PUQU-n-F
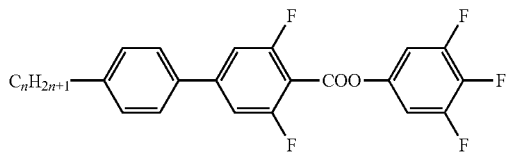
PUZU-n-F
In a preferred embodiment of the present invention, the LC media according to the invention comprise one or more compounds selected from the group consisting of compounds from Table A.
TABLE B
Table B shows possible chiral dopants which can be added to the LC media according to the invention.
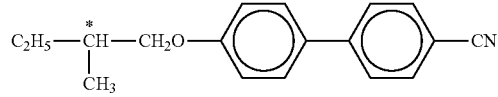
C 15
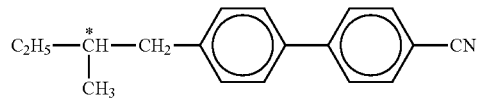
CB 15
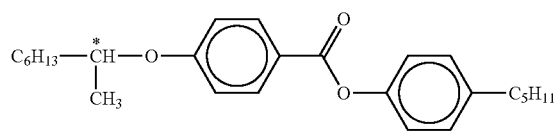
CM 21
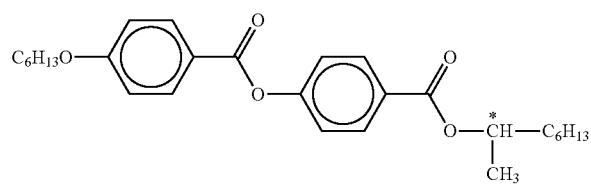
R/S-811
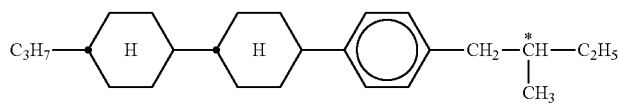
CM 44

TABLE B-continued
Table B shows possible chiral dopants which can be added to the LC media according to the invention.
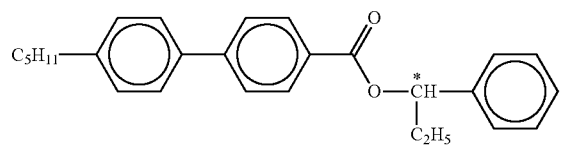
CM 45
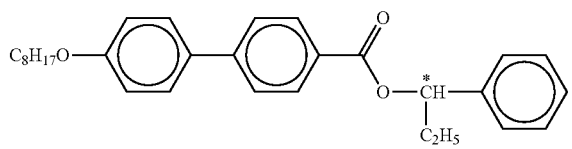
CM 47
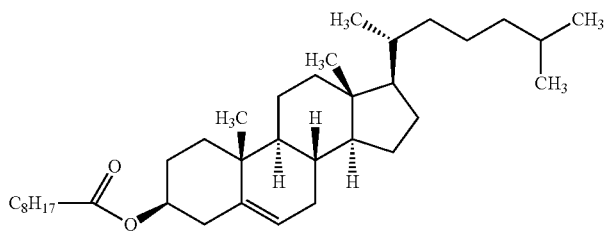
CN
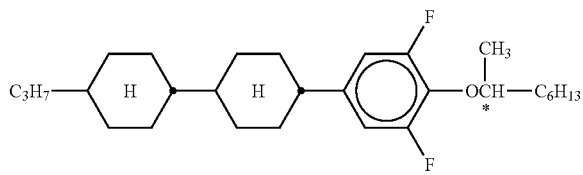
R/S-2011
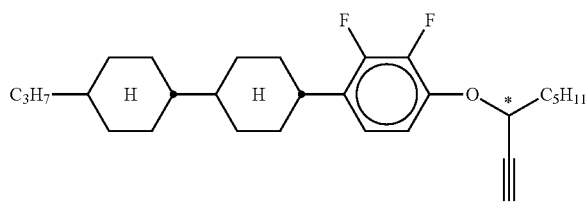
R/S-3011
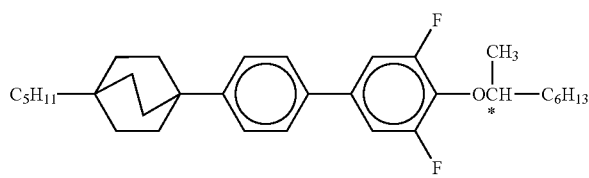
R/S-4011

TABLE B-continued

Table B shows possible chiral dopants which can be added to the LC media according to the invention.

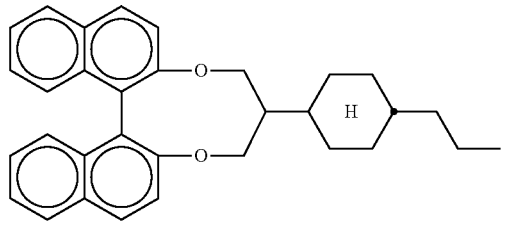

R/S-5011

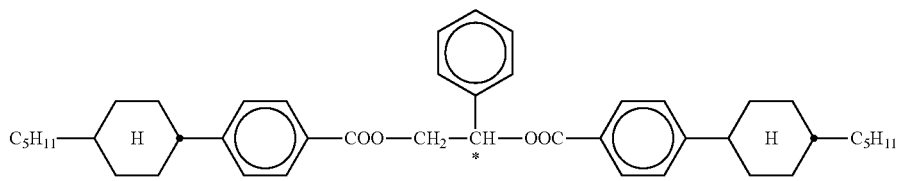

R/S-1011

The LC media preferably comprise 0 to 10% by weight, in particular 0.01 to 5% by weight, particularly preferably 0.1 to 3% by weight, of dopants. The LC media preferably comprise one or more dopants selected from the group consisting of compounds from Table B.

TABLE C

Table C shows possible stabilisers whiich can be added to the LC media according to the invention.

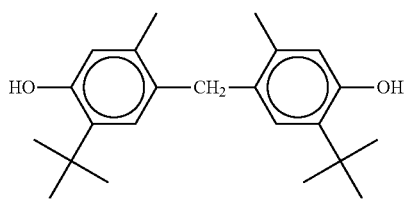

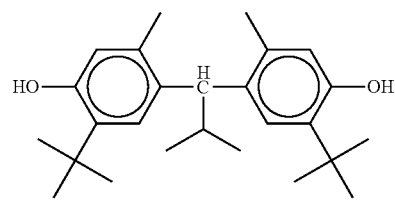

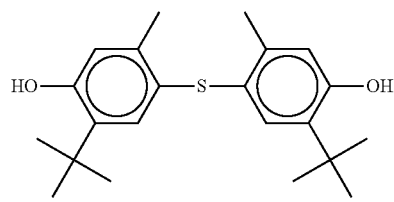

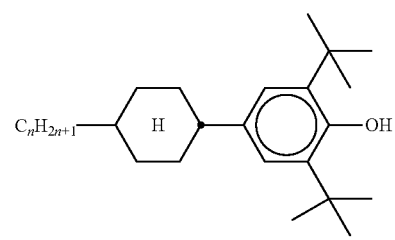

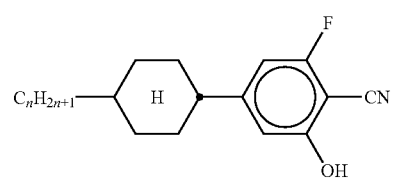

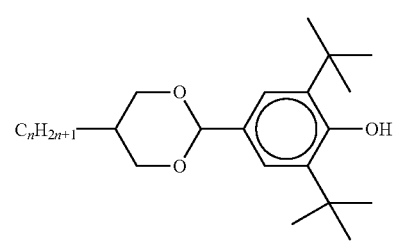

TABLE C-continued
Table C shows possible stabilisers whiich can be added to the LC media according to the invention.
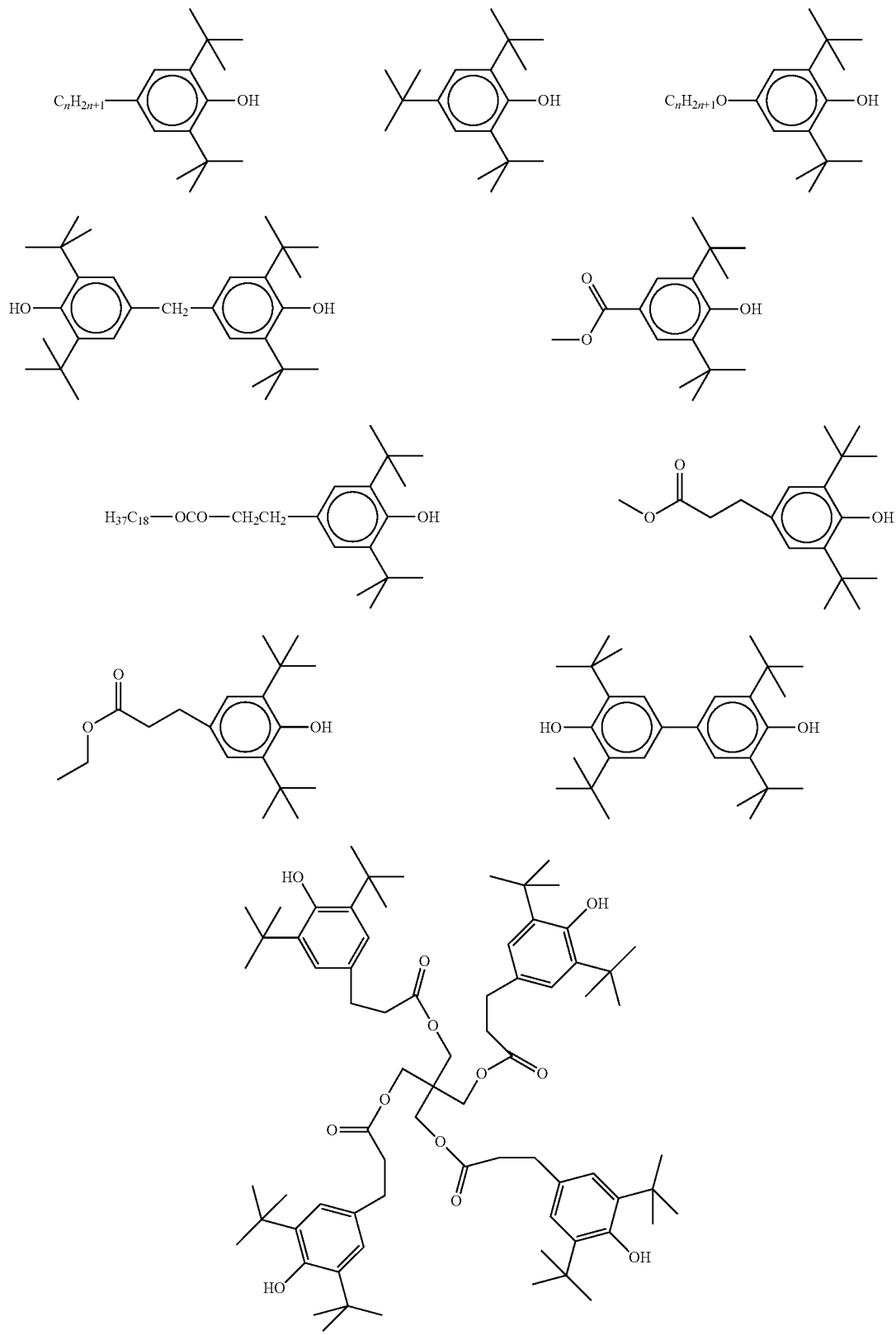

TABLE C-continued
Table C shows possible stabilisers whiich can be added to the LC media according to the invention.
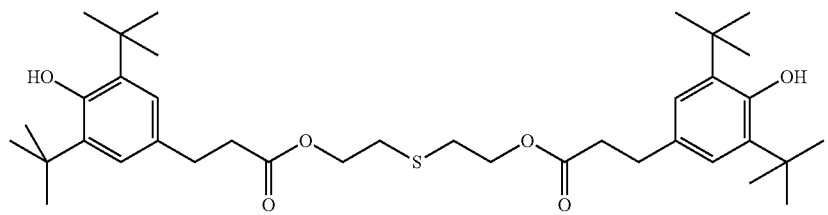 [SMILES: CC(C)(C)c1cc(CCC(=O)OCCSCCOC(=O)CCc2cc(C(C)(C)C)c(O)c(C(C)(C)C)c2)cc(C(C)(C)C)c1O]
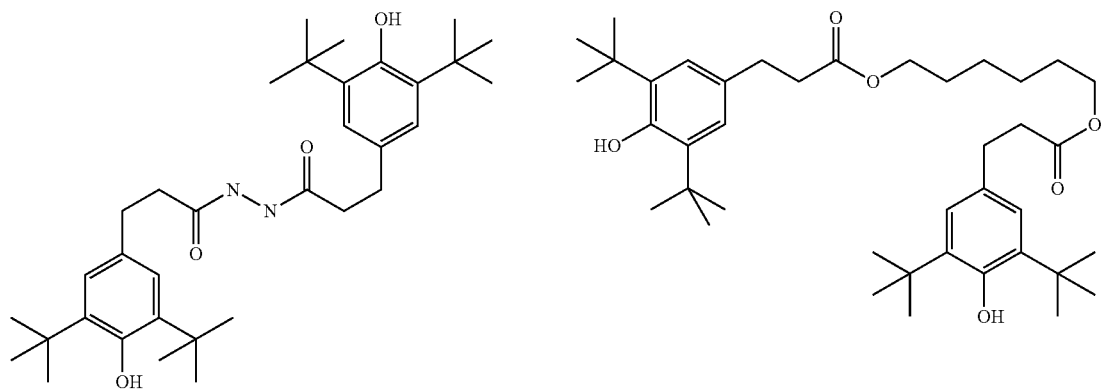
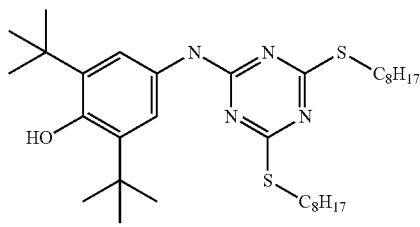
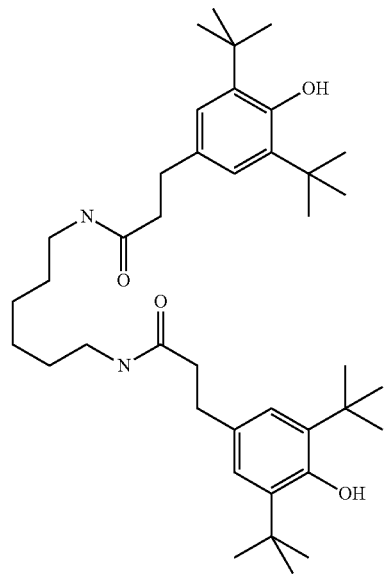 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]

TABLE C-continued
Table C shows possible stabilisers whiich can be added to the LC media according to the invention.
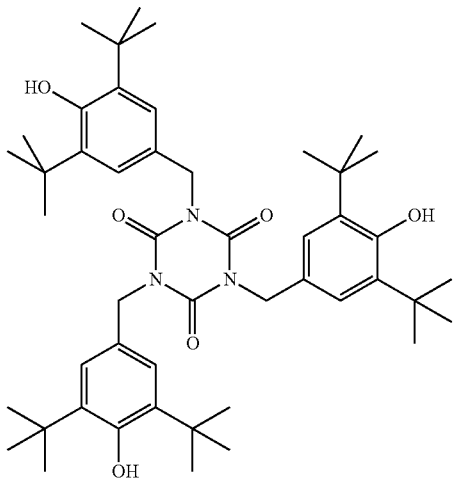 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
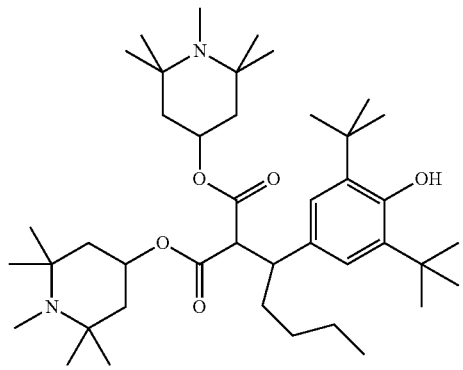 [SMILES: CCCCC(c1cc(C(C)(C)C)c(O)c(C(C)(C)C)c1)C(C(=O)OC1CC(C)(C)N(C)C(C)(C)C1)C(=O)OC1CC(C)(C)N(C)C(C)(C)C1]
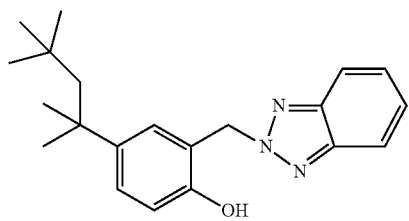 [SMILES: CC(C)(C)CC(C)(C)c1ccc(O)c(Cn2nc3ccccc3n2)c1]
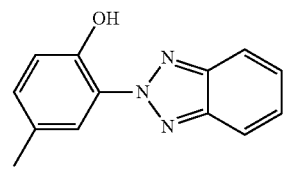 [SMILES: Cc1ccc(O)c(-n2nc3ccccc3n2)c1]
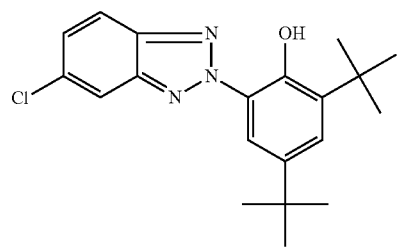 [SMILES: CC(C)(C)c1cc(-n2nc3ccc(Cl)cc3n2)c(O)c(C(C)(C)C)c1]
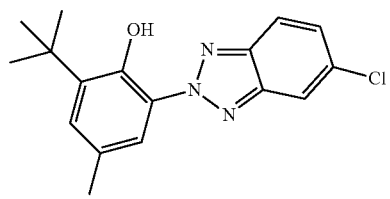 [SMILES: Cc1cc(-n2nc3ccc(Cl)cc3n2)c(O)c(C(C)(C)C)c1]
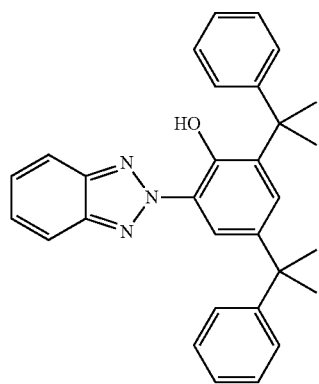 [SMILES: CC(C)(c1ccccc1)c1cc(-n2nc3ccccc3n2)c(O)c(C(C)(C)c2ccccc2)c1]
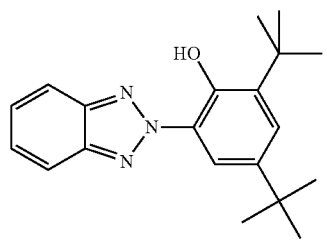 [SMILES: CC(C)(C)c1cc(-n2nc3ccccc3n2)c(O)c(C(C)(C)C)c1]

TABLE C-continued
Table C shows possible stabilisers whiich can be added to the LC media according to the invention.
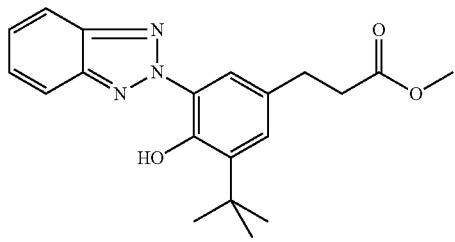 [SMILES: COC(=O)CCc1cc(-n2nc3ccccc3n2)c(O)c(C(C)(C)C)c1]
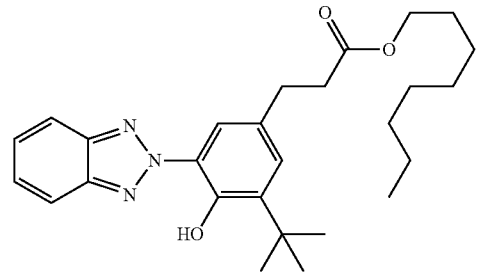 [SMILES: CCCCCCCCOC(=O)CCc1cc(-n2nc3ccccc3n2)c(O)c(C(C)(C)C)c1]
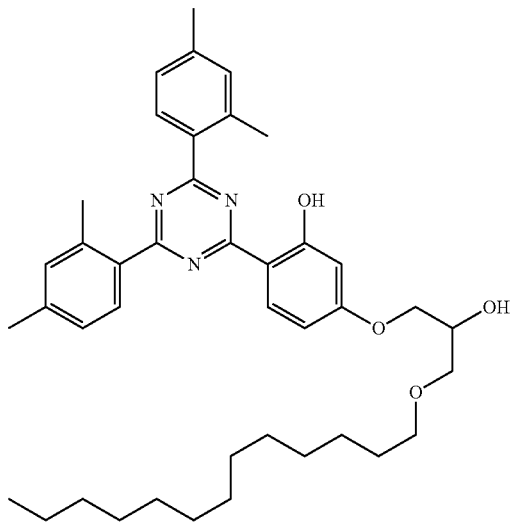 [SMILES: CCCCCCCCCCCCCOCC(O)COc1ccc(-c2nc(-c3ccc(C)cc3C)nc(-c3ccc(C)cc3C)n2)c(O)c1]
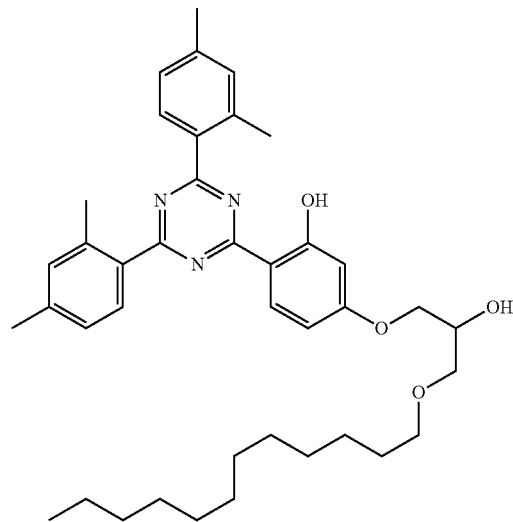 [SMILES: CCCCCCCCCCCCOCC(O)COc1ccc(-c2nc(-c3ccc(C)cc3C)nc(-c3ccc(C)cc3C)n2)c(O)c1]
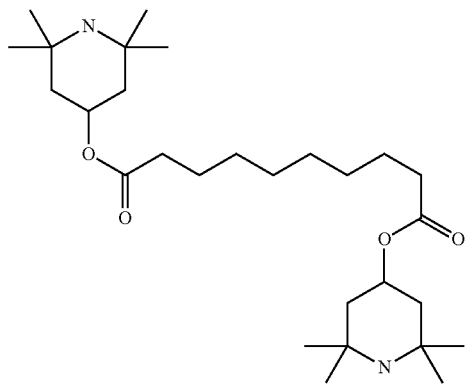
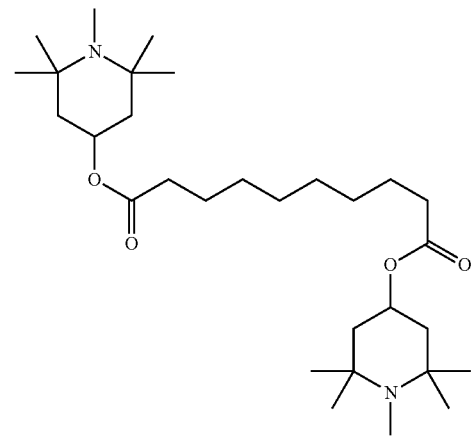
(n here denotes an integer from 1 to 12, preferably 1, 2, 3, 4, 5, 6, 7 or 8, terminal methyl groups are not shown).

The LC media preferably comprise 0 to 10% by weight, in particular 1 ppm to 5% by weight, particularly preferably 1 ppm to 1% by weight, of stabilisers. The LC media preferably comprise one or more stabilisers selected from the group consisting of compounds from Table C.

TABLE D

Table D shows illustrative compounds which can be used in the LC media in accordance with the present invention, preferably as reactive mesogenic compounds.

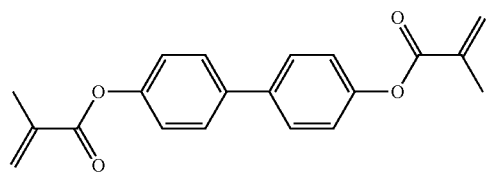

RM-1

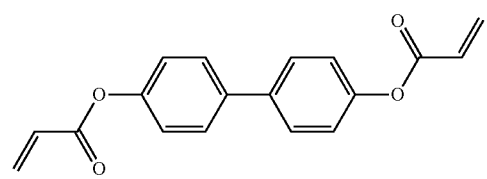

RM-2

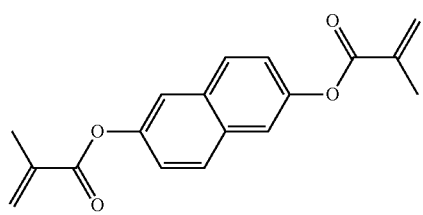

RM-3

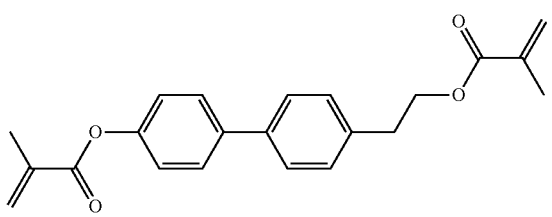

RM-4

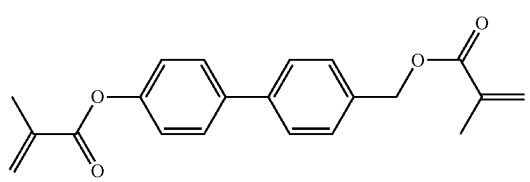

RM-5

TABLE D-continued
Table D shows illustrative compounds which can be used in the LC media in accordance with the present invention, preferably as reactive mesogenic compounds.
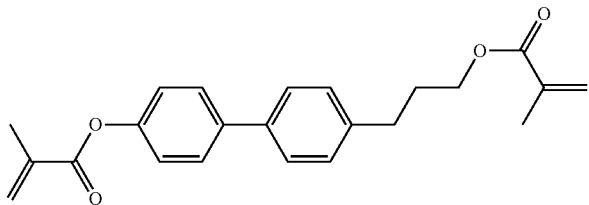
RM-6
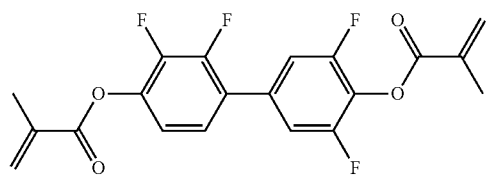
RM-7
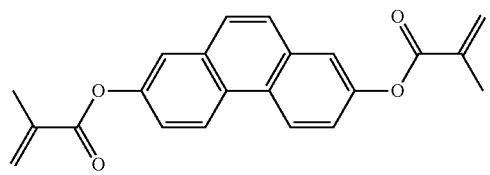
RM-8
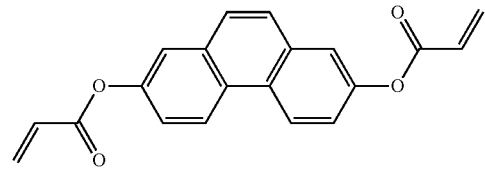
RM-9
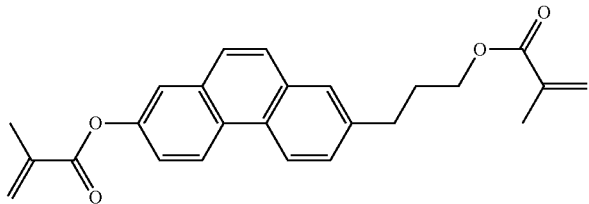
RM-10
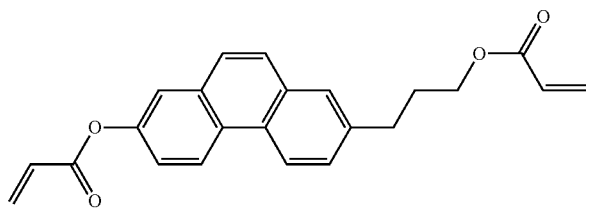
RM-11

TABLE D-continued
Table D shows illustrative compounds which can be used in the LC media in accordance with the present invention, preferably as reactive mesogenic compounds.
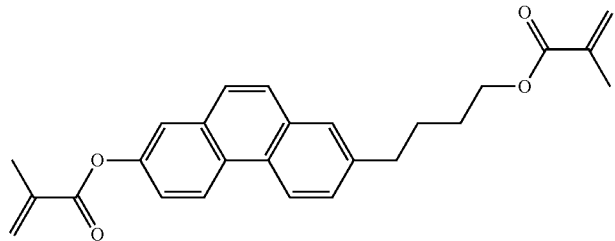
RM-12
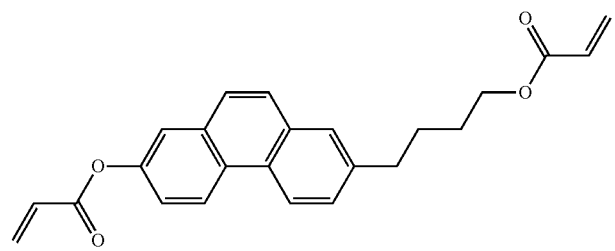
RM-13
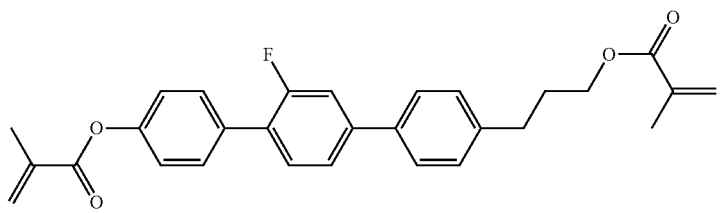
RM-14
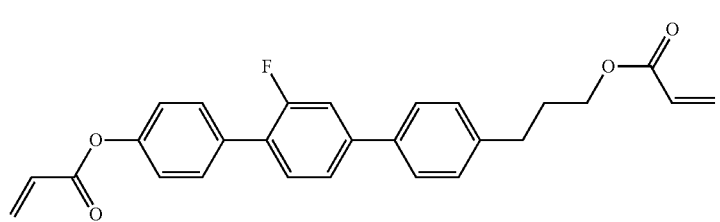
RM-15
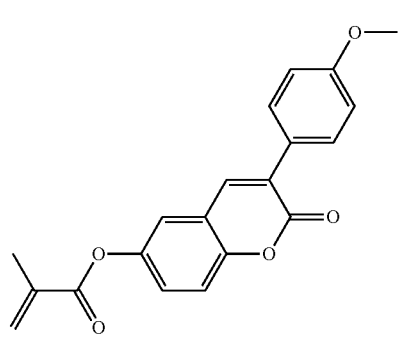
RM-16

TABLE D-continued
Table D shows illustrative compounds which can be used in the LC media in accordance with the present invention, preferably as reactive mesogenic compounds.
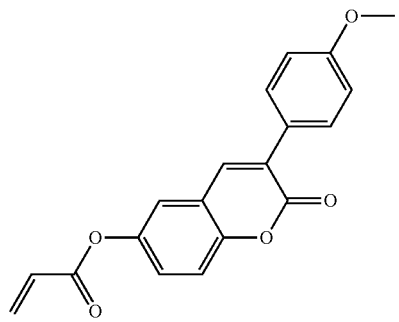
RM-17
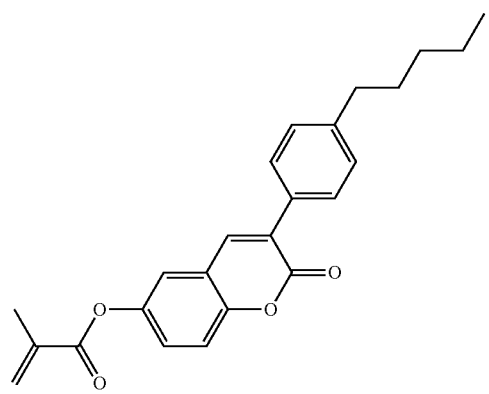
RM-18
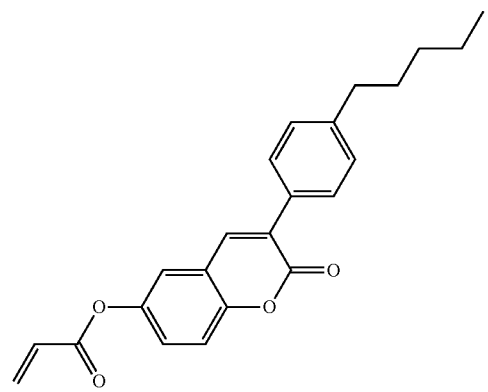
RM-19
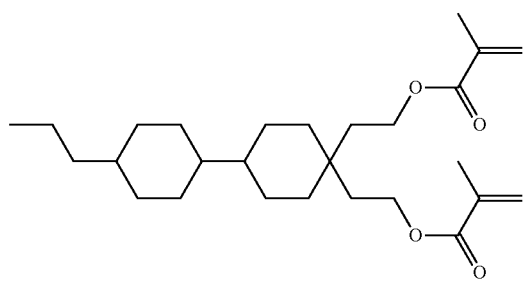
RM-20

TABLE D-continued
Table D shows illustrative compounds which can be used in the LC media in accordance with the present invention, preferably as reactive mesogenic compounds.
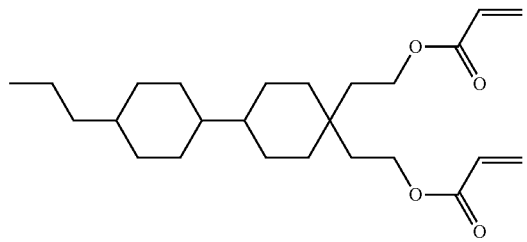
RM-21
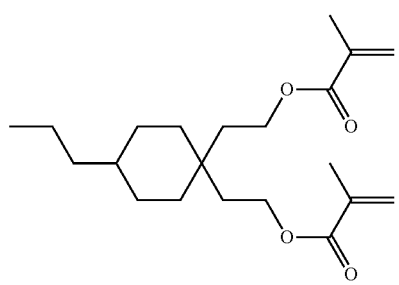
RM-22
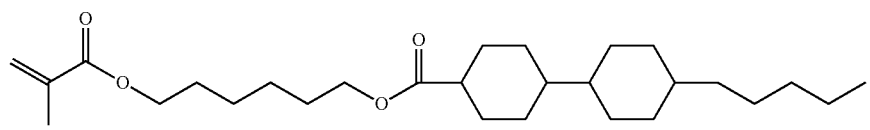
RM-23
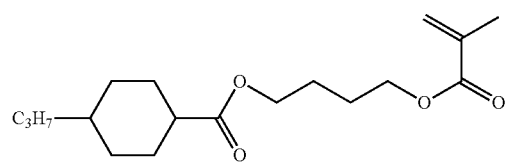
RM-24
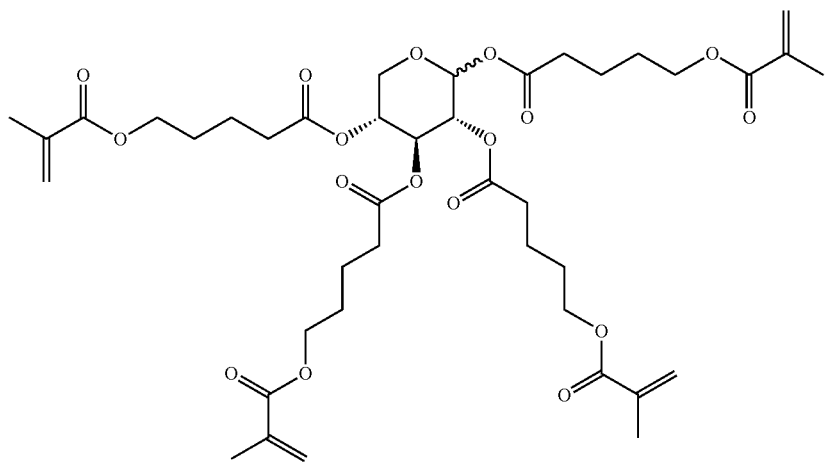
RM-25

TABLE D-continued

Table D shows illustrative compounds which can be used in the LC media in accordance with the present invention, preferably as reactive mesogenic compounds.

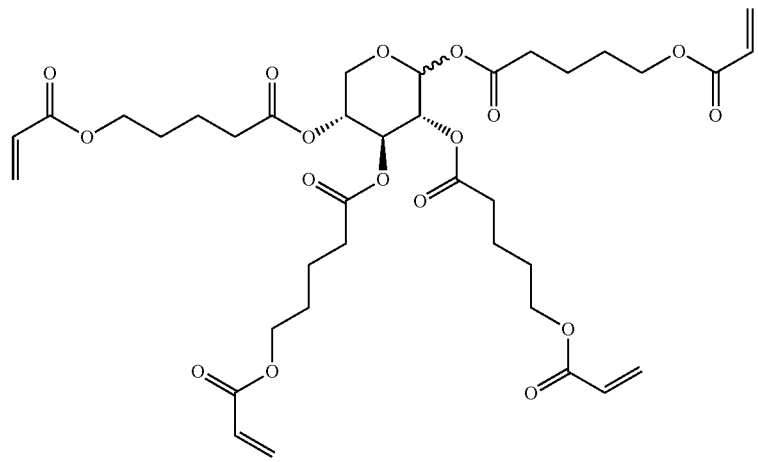

RM-26

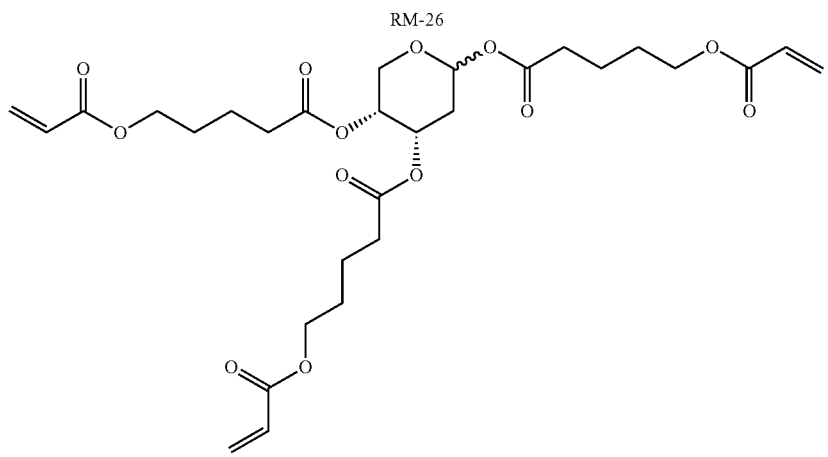

RM-27

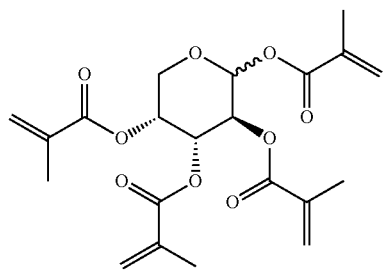

RM-28

In a preferred embodiment of the present invention, the mesogenic media comprise one or more compounds selected from the group of the compounds from Table D.

In addition, the following abbreviations and symbols are used:

$V_0$ threshold voltage, capacitive [V] at 20° C.,
$n_e$ extraordinary refractive index at 20° C. and 589 nm,
$n_o$ ordinary refractive index at 20° C. and 589 nm,
$\Delta n$ optical anisotropy at 20° C. and 589 nm,
$\epsilon_\perp$ dielectric permittivity perpendicular to the director at 20° C. and 1 kHz,
$\epsilon_\parallel$ dielectric permittivity parallel to the director at 20° C. and 1 kHz,
$\Delta\epsilon$ dielectric anisotropy at 20° C. and 1 kHz,
cl.p., T(N,I) clearing point [° C.],
$\gamma_1$ rotational viscosity at 20° C. [mPa·s],
$K_1$ elastic constant, "splay" deformation at 20° C. [pN],
$K_2$ elastic constant, "twist" deformation at 20° C. [pN],
$K_3$ elastic constant, "bend" deformation at 20° C. [pN].

Unless explicitly noted otherwise, all concentrations in the present application are quoted in percent by weight and relate to the corresponding mixture as a whole, comprising all solid or liquid-crystalline components, without solvents.

Unless explicitly noted otherwise, all temperature values indicated in the present application, such as, for example, for the melting point T(C,N), the transition from the smectic (S) to the nematic (N) phase T(S,N) and the clearing point T(N,I), are quoted in degrees Celsius (° C.). M.p. denotes melting point, cl.p.=clearing point. Furthermore, Tg=glass state, C=crystalline state, N=nematic phase, S=smectic phase and I=isotropic phase. The data between these symbols represent the transition temperatures.

All physical properties are and have been determined in accordance with "Merck Liquid Crystals, Physical Properties of Liquid Crystals", Status November 1997, Merck KGaA, Germany, and apply for a temperature of 20° C., and An is determined at 589 nm and $\Delta\in$ at 1 kHz, unless explicitly indicated otherwise in each case.

The term "threshold voltage" for the present invention relates to the capacitive threshold ($V_0$), also known as the Freedericks threshold, unless explicitly indicated otherwise. In the examples, the optical threshold may also, as generally usual, be quoted for 10% relative contrast ($V_{10}$).

The display used for measurement of the capacitive threshold voltage consists of two plane-parallel glass outer plates at a separation of 20 µm, each of which has on the inside an electrode layer and an unrubbed polyimide alignment layer on top, which effect a homeotropic edge alignment of the liquid-crystal molecules.

The display or test cell used for measurement of the tilt angles consists of two plane-parallel glass outer plates at a separation of 4 µm, each of which has on the inside an electrode layer and a polyimide alignment layer on top, where the two polyimide layers are rubbed antiparallel to one another and effect a homeotropic edge alignment of the liquid-crystal molecules.

The polymerisable compounds are polymerised in the display or test cell by irradiation with UVA light (usually 365 nm) of defined intensity for a prespecified time, with a voltage simultaneously being applied to the display (usually 10 V to 30 V alternating current, 1 kHz). In the examples, unless indicated otherwise, a 50 mW/cm² mercury vapour lamp is used, and the intensity is measured using a standard UV meter (model Ushio UNI meter) fitted with a 365 nm band-pass filter.

The tilt angle is determined by a crystal rotation experiment (Autronic-Melchers TBA-105). A low value (i.e. a large deviation from the 90° angle) corresponds to a large tilt here.

The VHR value is measured as follows: 0.3% of a polymerisable monomeric compound is added to the LC host mixture, and the resultant mixture is introduced into TN-VHR test cells (rubbed at 90°, TN-polyimide alignment layer, layer thickness d≈6 µm). The HR value is determined after 5 min at 100° C. before and after UV exposure for 2 h (sun test) at 1 V, 60 Hz, 64 µs pulse (measuring instrument: Autronic-Melchers VHRM-105).

In order to investigate the low-temperature stability, also referred to as "LTS", i.e. the stability of the LC mixture to individual components spontaneously crystallising out at low temperatures, bottles containing 1 g of LC/RM mixture are placed in storage at −10° C., and it is regularly checked whether the mixtures have crystallised out.

The so-called "HTP" ("helical twisting power") denotes the helical twisting power of an optically active or chiral substance in an LC medium (in µm). Unless indicated otherwise, the HTP is measured in the commercially available nematic LC host mixture MLD-6260 (Merck KGaA) at a temperature of 20° C.

EXAMPLE 1

Compound (1): 5-{4-[(4-{[4-(5-Acryloyloxypent-1-ynyl)phenyl]difluoromethoxy}-3-methylphenoxy)difluoromethyl]phenyl}pent-4-ynyl acrylate

1.1. 1,4-Bis-[(4-bromophenyl)difluoromethoxy]-2-methylbenzene

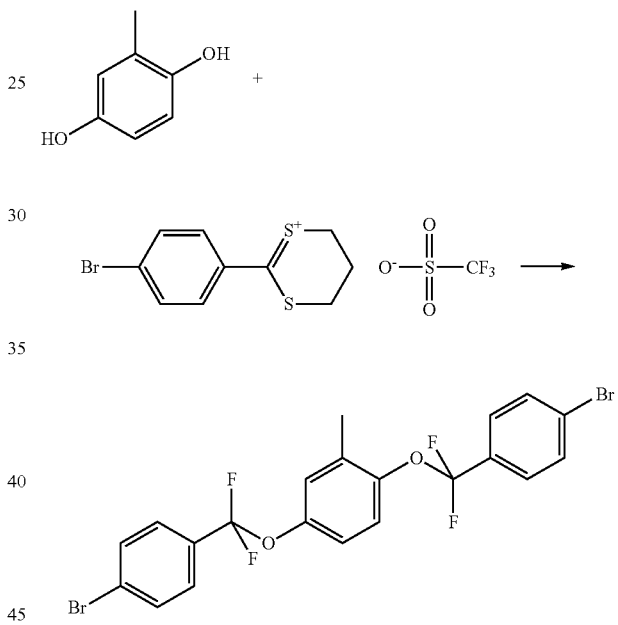

102 g (0.24 mol) of 2-(4-bromophenyl)-5,6-dihydro-4H-1, 3-dithiyn-1-ylium triflate are initially introduced in 500 ml of dichloromethane at −70° C., 38 ml (0.27 mol) of triethylamine are added, and a solution of 9.0 g (72.5 mmol) of 2-methylhydroquinone in 100 ml of dichloromethane is added. After 30 min, 117 ml (0.73 mol) of triethylamine trishydrofluoride are added, and a solution of 37 ml (0.72 mol) of bromine in 100 ml of dichloromethane is subsequently allowed to run in dropwise. The mixture is subsequently stirred for 1 h, the cooling is removed, and the batch is allowed to thaw to 5° C. and added to 1 l of 10 percent sodium hydroxide solution. The aqueous phase is separated off and extracted three times with dichloromethane. The combined org. phases are washed with water, dried over sodium sulfate, and the solvent is removed in vacuo. The residue is filtered through silica gel with heptane/toluene (4:1), and the crude product is recrystallised from ethanol, giving 1,4-bis-[(4-bromophenyl)difluoromethoxy]-2-methylbenzene as a colourless solid.

1.2. 5-{4-[(4-{Difluoro-[4-(5-hydroxypent-1-ynyl)phenyl]methoxy}-3-methylphenoxy)difluoromethyl]phenyl}pent-4-yn-1-ol

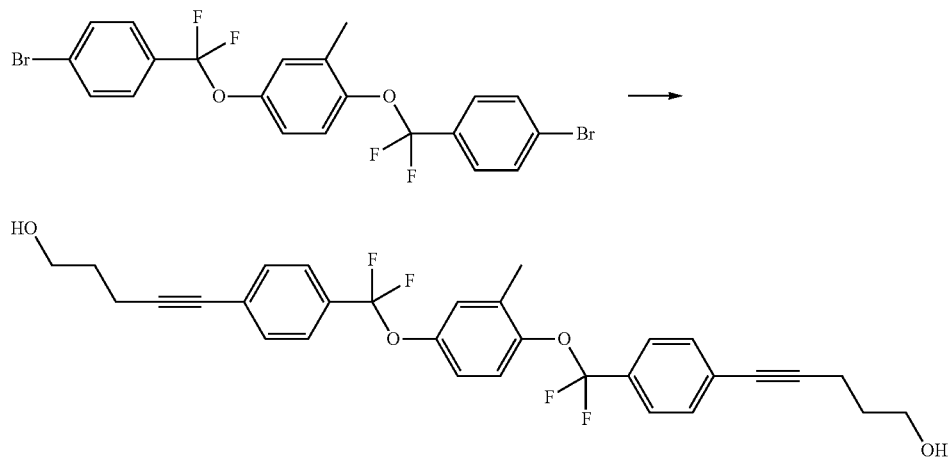

29.5 g (55.2 mmol) of 1,4-bis-[(4-bromophenyl)difluoromethoxy]-2-methylbenzene are initially introduced in 400 ml of DMF and 30 ml of triethylamine, 1 g (5.2 mmol) of copper(I) iodide and 4.0 g (5.7 mmol) of bis(triphenylphosphine) palladium(II) chloride are added, the mixture is warmed to 60° C., and a solution of 17.0 g (0.2 mol) of 1-pentynol in 100 ml of DMF is added. The batch is left to stir overnight at 75° C., MTB ether is added, and the mixture is washed twice with water. The aqueous phase is extracted with MTB ether, and the combined org. phases are washed with sat. sodium chloride solution and dried over sodium sulfate.

The solvent is removed in vacuo, and the residue is recrystallised from heptane/toluene (1:1), giving 5-{4-[(4-{difluoro-[4-(5-hydroxypent-1-ynyl)phenyl]methoxy}-3-methylphenoxy)difluoromethyl]phenyl}pent-4-yn-1-ol as a colourless solid.

1.3. 5-{4-[(4-{[4-(5-Acryloyloxypent-1-ynyl)phenyl]difluoromethoxy}-3-methylphenoxy)difluoromethyl]phenyl}pent-4-ynyl acrylate

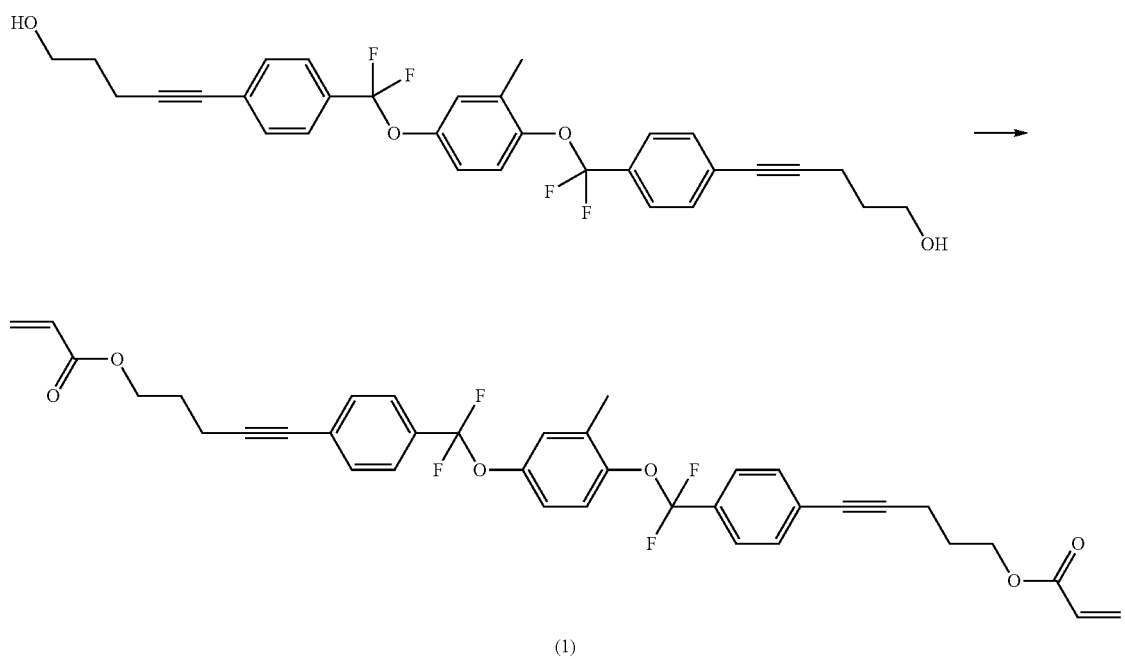 [SMILES: Cc1cc(OC(F)(F)c2ccc(C#CCCCO)cc2)ccc1OC(F)(F)c1ccc(C#CCCCO)cc1 ; C=CC(=O)OCCCC#Cc1ccc(C(F)(F)Oc2ccc(OC(F)(F)c3ccc(C#CCCCOC(=O)C=C)cc3)c(C)c2)cc1]

(1)

2.20 g (4.07 mmol) of 5-{4-[(4-{difluoro-[4-(5-hydroxypent-1-ynyl)phenyl]-methoxy}-3-methylphenoxy)difluoromethyl]phenyl}pent-4-yn-1-ol are initially introduced in 70 ml of dichloromethane, and 2.5 ml (18 mmol) of triethylamine and subsequently 1.2 ml (15 mmol) of acryloyl chloride in 10 ml of dichloromethane are added with ice-cooling. The cooling is removed, and the batch is left to stir for 2 h at room temp. The solvent is removed in vacuo, and the residue is chromatographed on silica gel with heptene/MTB ether (3:2), giving 5-{4-[(4-{[4-(5-acryloyloxypent-1-ynyl)phenyl]difluoromethoxy}-3-methylphenoxy)difluoromethyl]phenyl}pent-4-ynyl acrylate as a colourless solid of m.p. 51° C.

Phase behaviour Tg −50 C 51 I.

EXAMPLE 2

Compound (2): 5-{4-[(4-{[4-(5-Methacryloyloxypentyl)phenyl]difluoromethoxy}-3-methylphenoxy)difluoromethyl]phenyl}pentyl methacrylate 2.1. 5-{4-[(4-{Difluoro-[4-(5-hydroxypentyl)phenyl]methoxy}-2-methylphenoxy)difluoromethyl]phenyl}pentan-1-ol

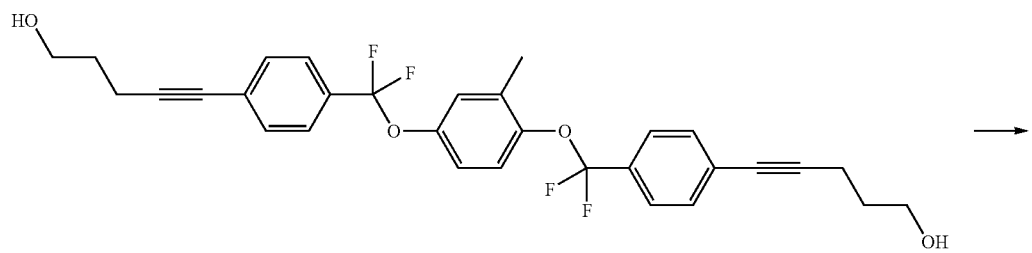

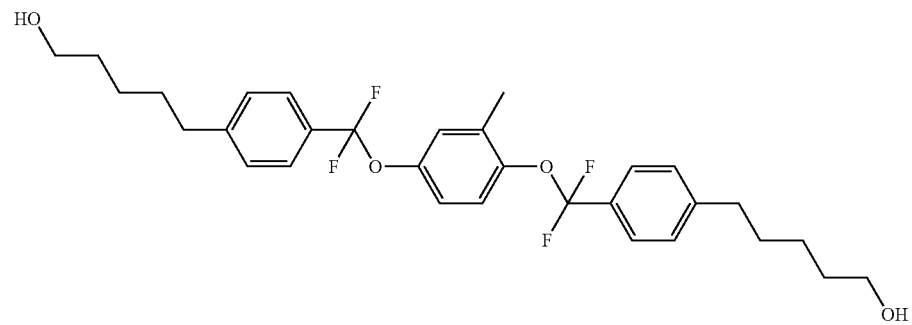

5-{4-[(4-{Difluoro-[4-(5-hydroxypent-1-ynyl)phenyl]methoxy}-3-methylphenoxy)difluoromethyl]phenyl}pent-4-yn-1-ol is hydrogenated to completion on palladium/active carbon catalyst in THF. The catalyst is filtered off, and the filtrate is evaporated in vacuo, giving 5-{4-[(4-{difluoro-[4-(5-hydroxypentyl)phenyl]methoxy}-2-methylphenoxy)difluoromethyl]phenyl}-pentan-1-ol, which is sufficiently pure for further reactions.

2.2. 5-{4-[(4-{[4-(5-Methacryloyloxypentyl)phenyl]difluoromethoxy}-3-methylphenoxy)difluoromethyl]phenyl}pentyl methacrylate An analogous synthesis to that described under 1.3. starting from 5-{4-[(4-{difluoro-[4-(5-hydroxypentyl)phenyl]methoxy}-2-methylphenoxy)difluoromethyl]phenyl}pentan-1-ol and methacryloyl chloride gives 5-{4-[(4-{[4-(5-methacryloyloxypentyl)phenyl]difluoromethoxy}-3-methylphenoxy)difluoromethyl]phenyl}pentyl methacrylate as a colourless solid of m.p. 26° C.

Phase behaviour Tg –56 C 26 N (–11) I

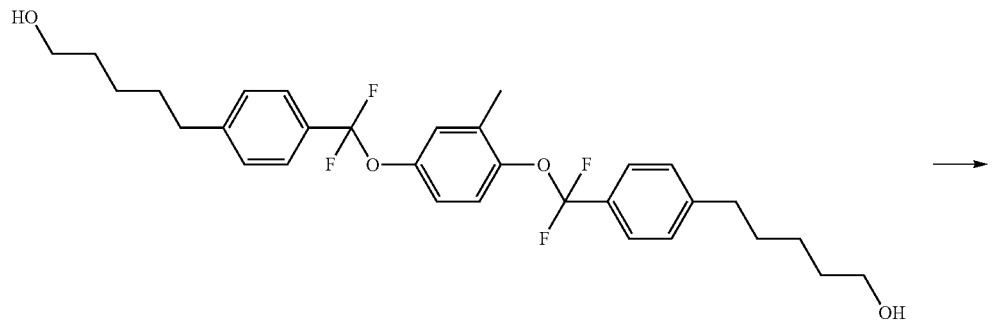

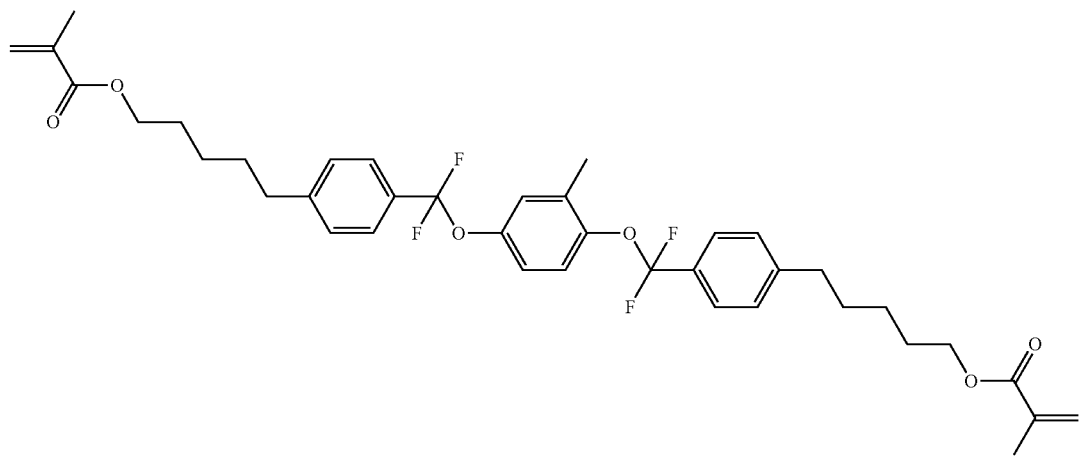

EXAMPLES 3-25
The following compounds according to the invention are prepared analogously to Examples 1 and 2.
(3)
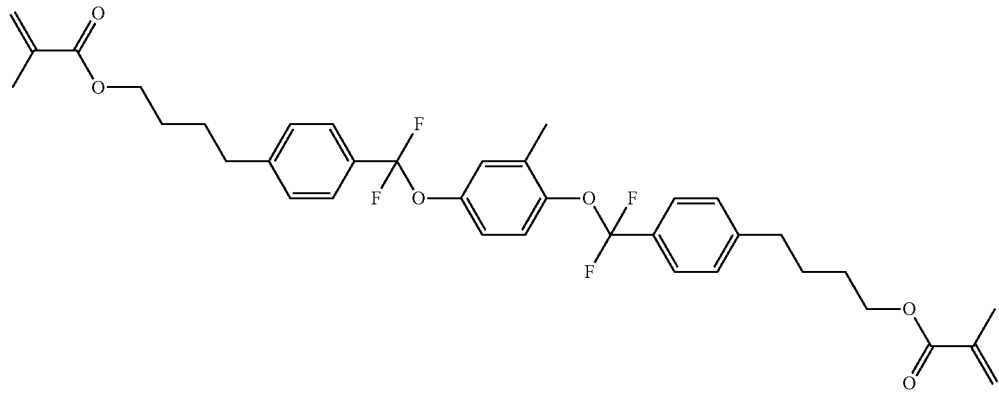
Tg -56 C 11 N (-27) I
(4)
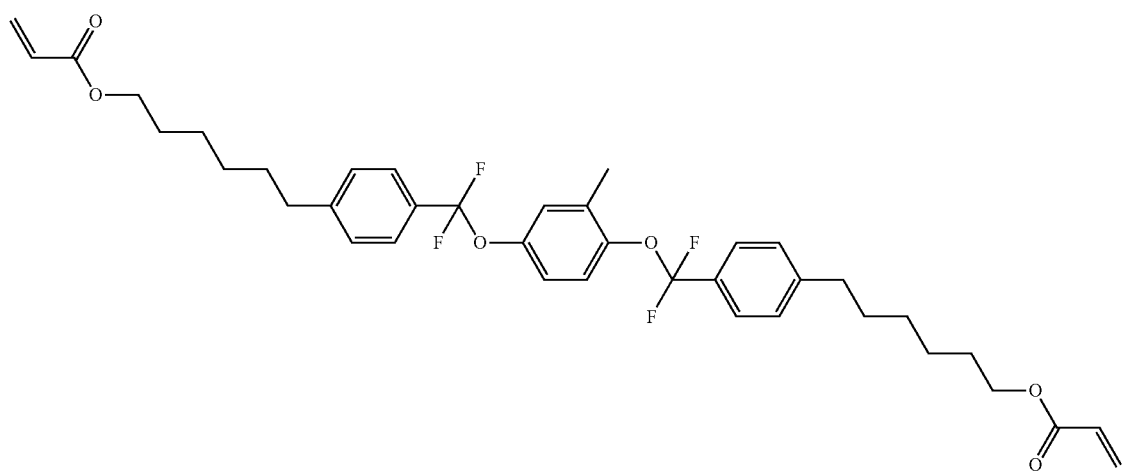
Tg -62 C 7 N 11 I
(5)
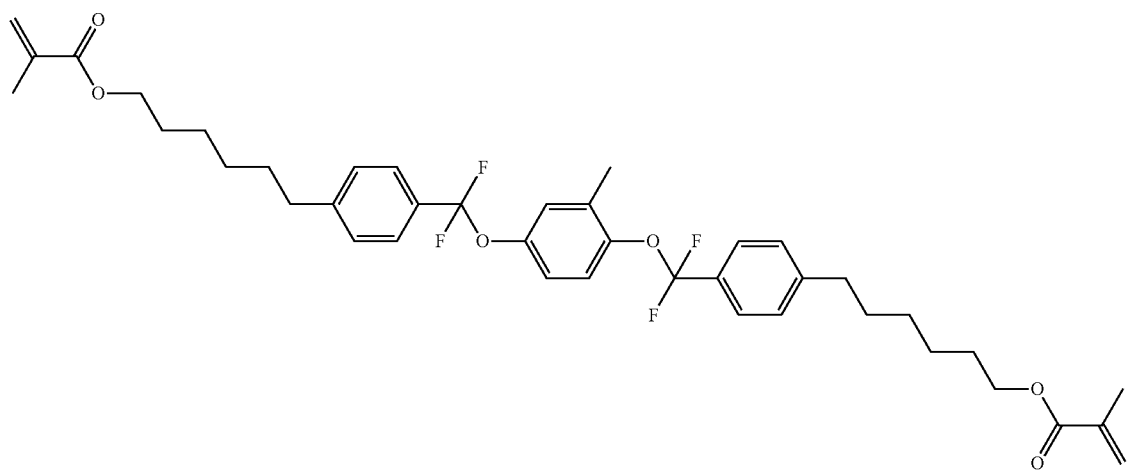
Tg -63 C 12 N (-1) I (6)
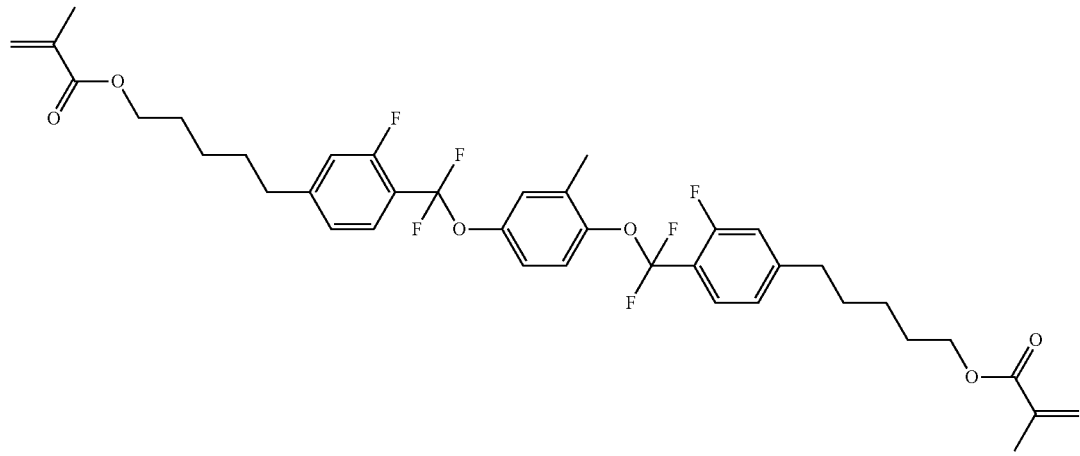
Tg -54 C -42 I
(7)
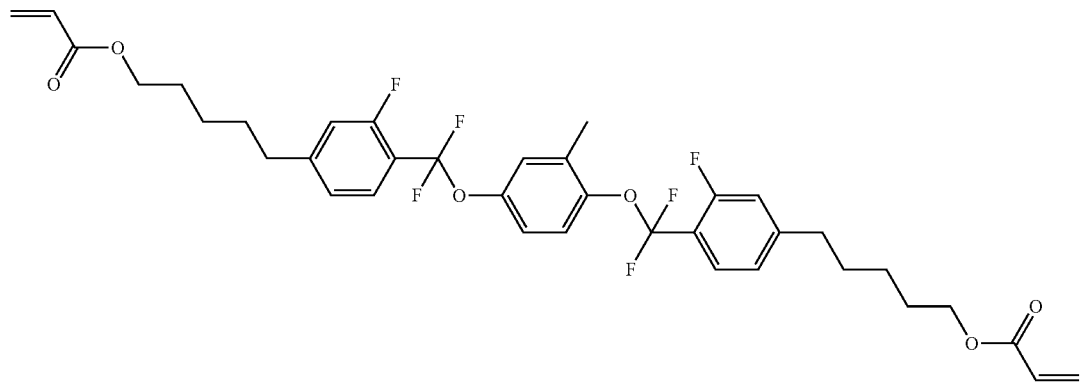
C 35 I
(8)
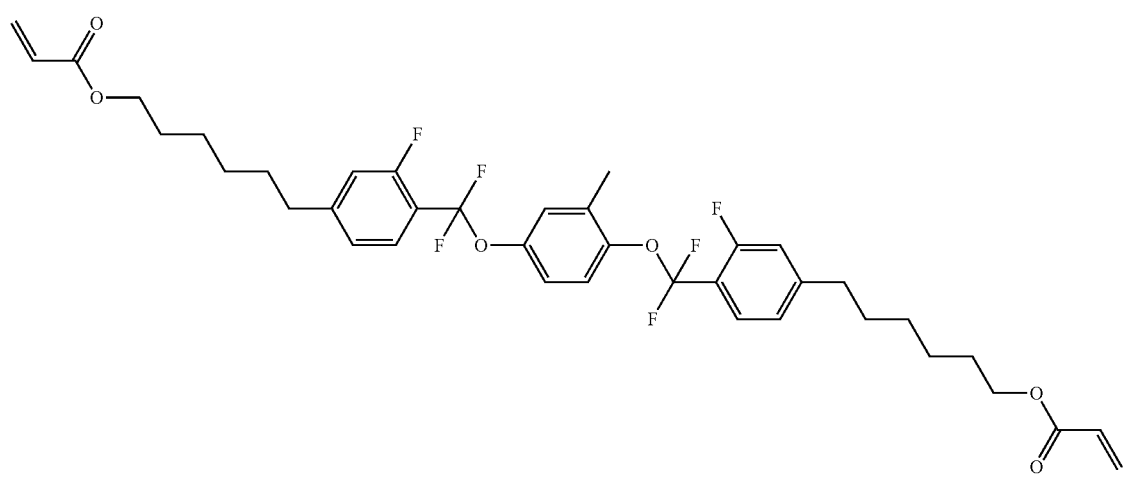
Tg -60 C -1 N (-23) I (9)
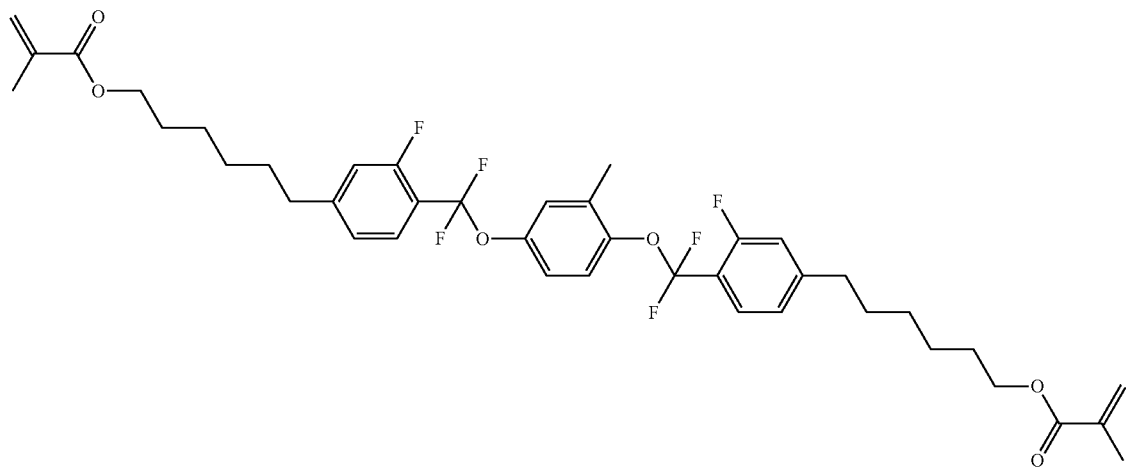
Tg -59 C 11 N (-32) I
(10)
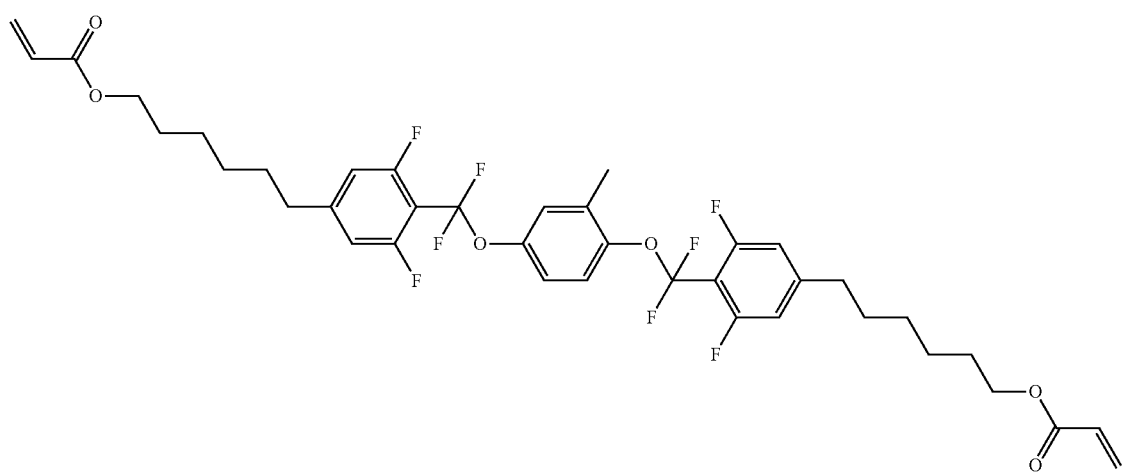
C 33 I
(11)
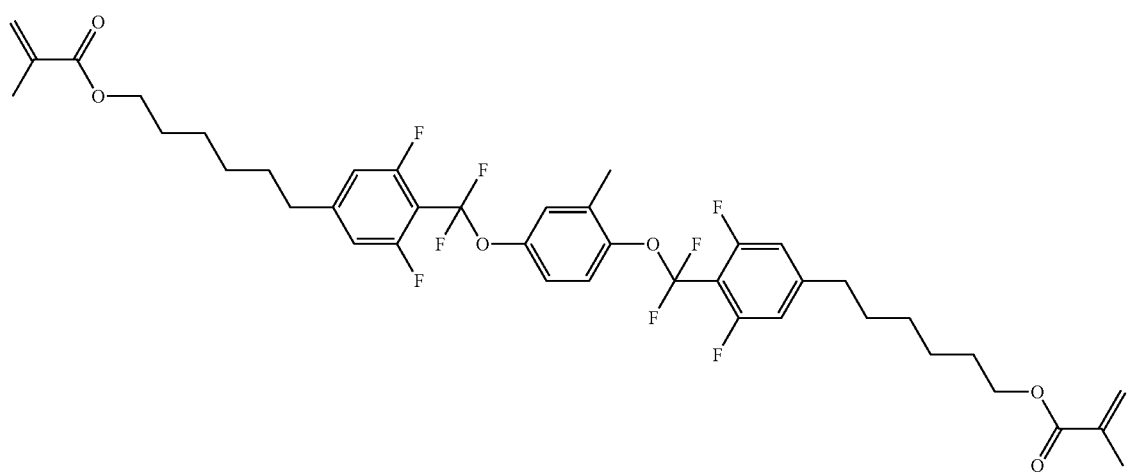
Tg -53 C 22 I

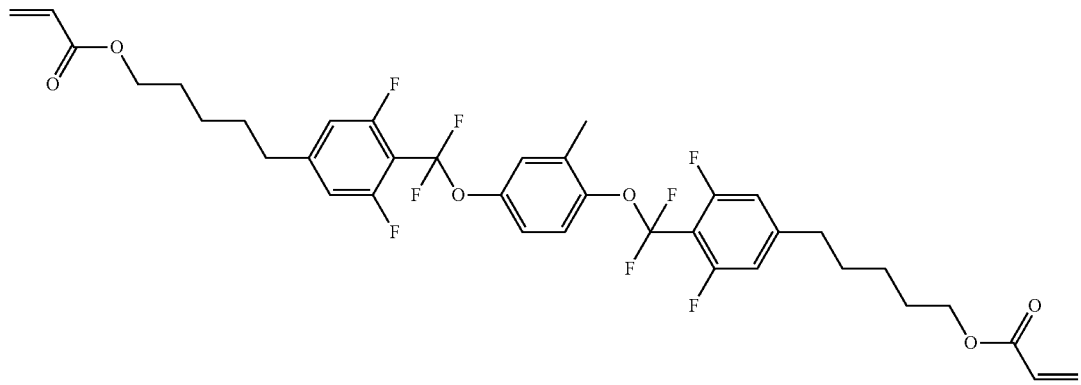
(12)
C 75 I
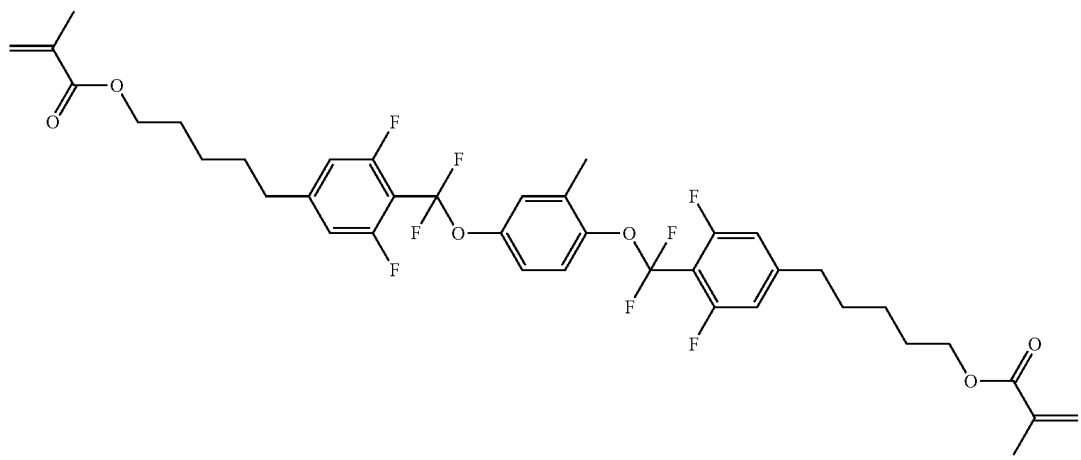
(13)
C 71 I
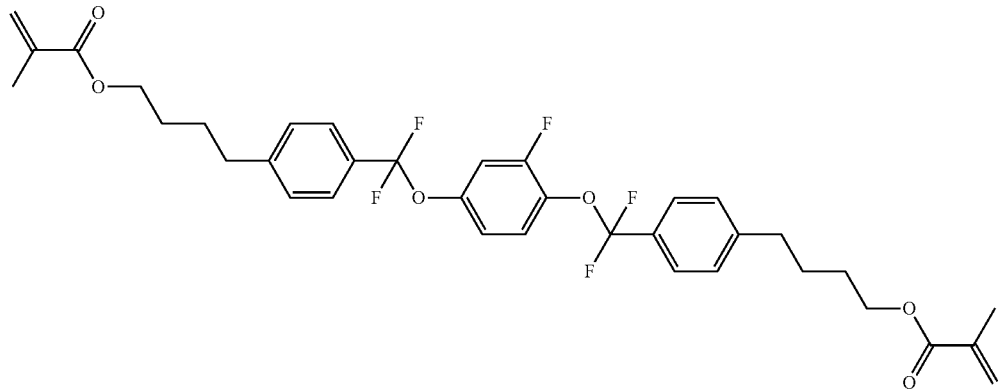
(14)
C 39 I

-continued
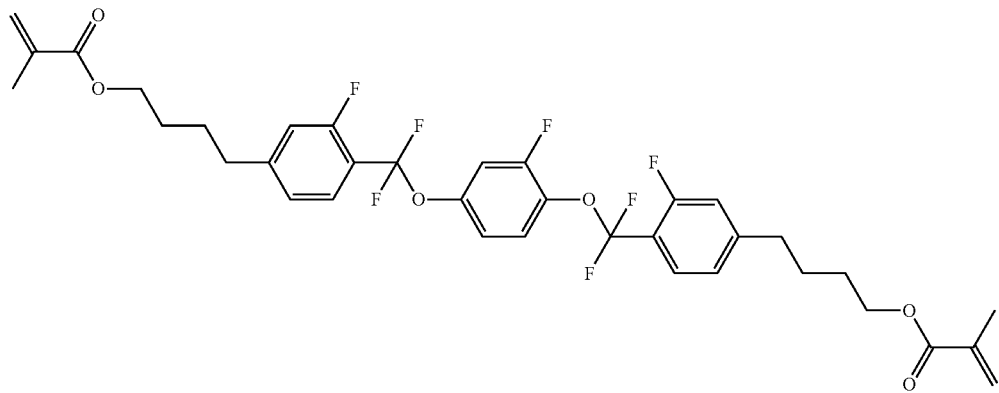
C 53 I
(15)
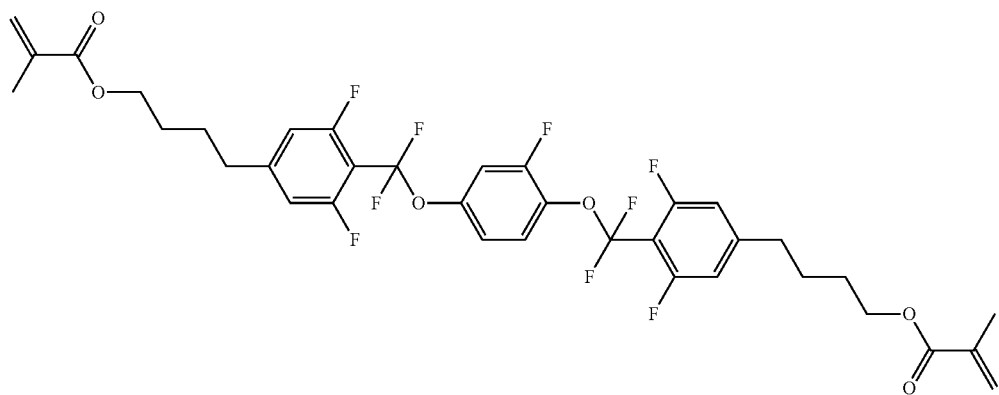
C 78 I
(16)
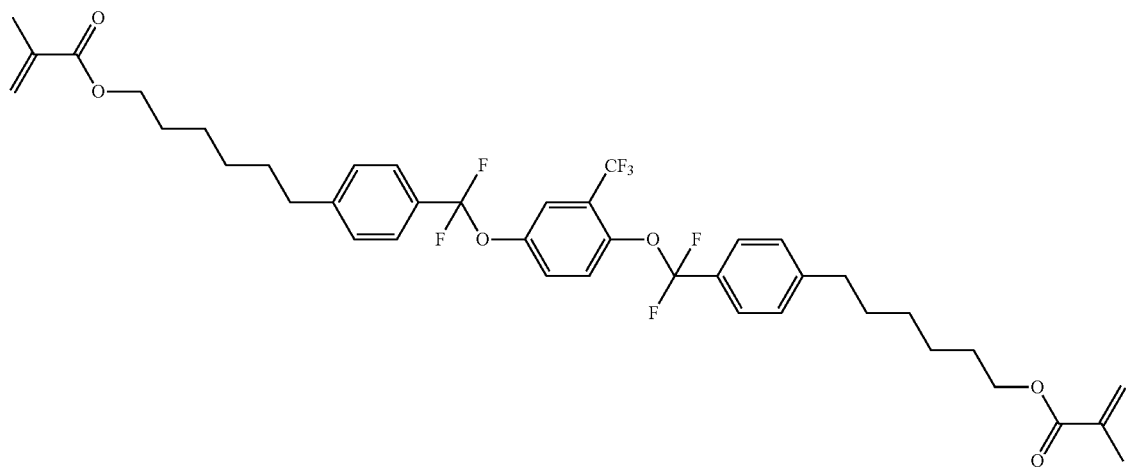
Tg -38 I
(17)
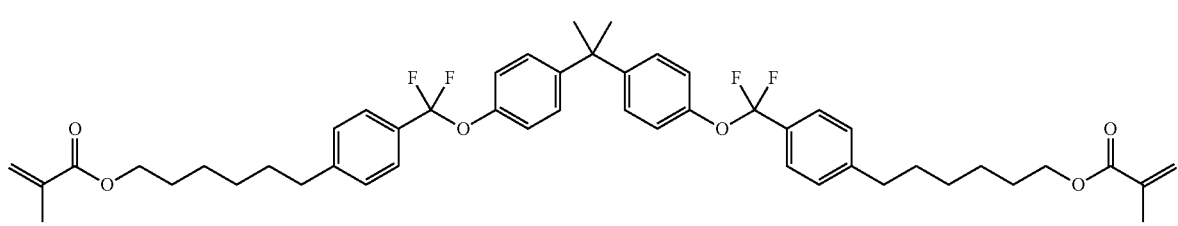
Tg -45 I
(18)

-continued
(19)
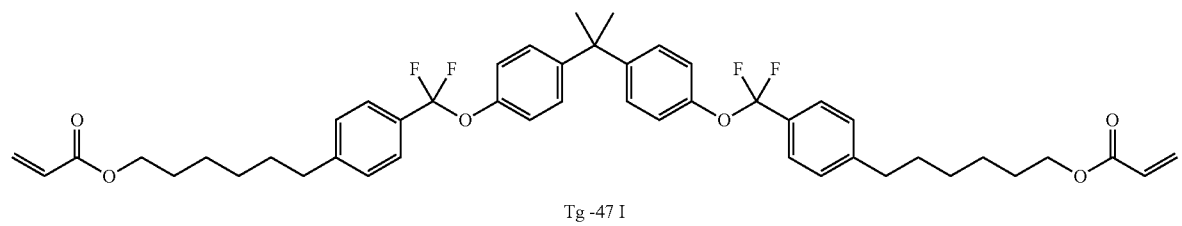
Tg -47 I
(20)
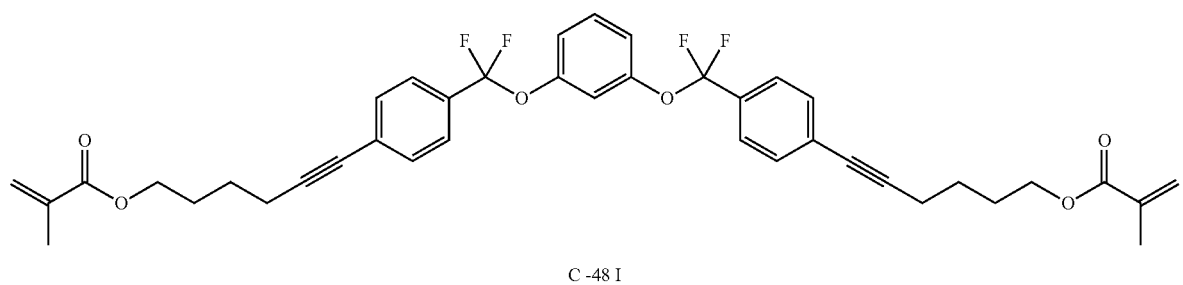
C -48 I
(21)
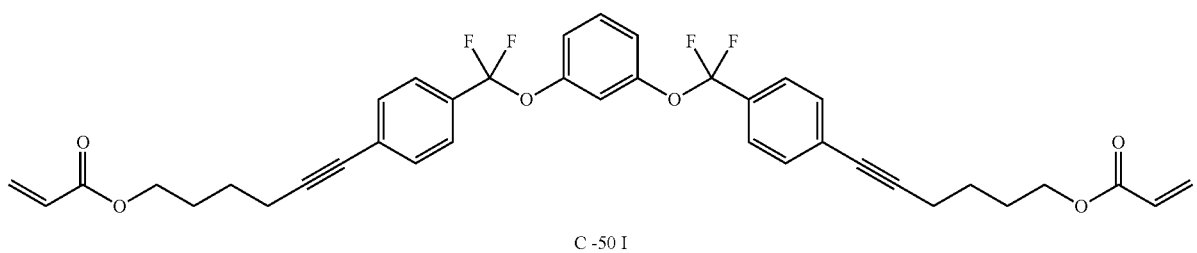
C -50 I
(22)
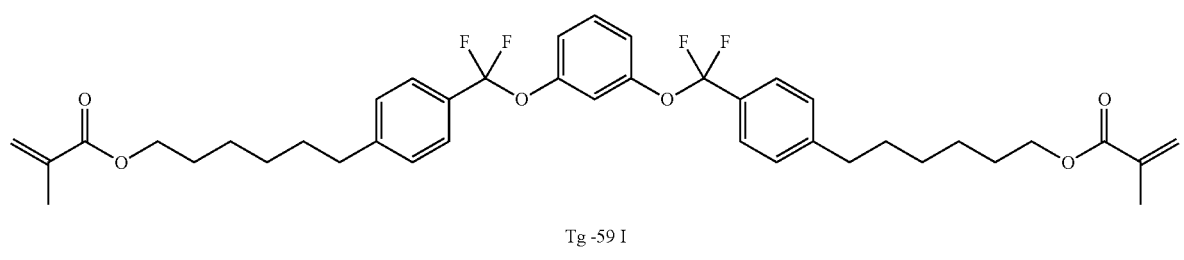
Tg -59 I
(23)
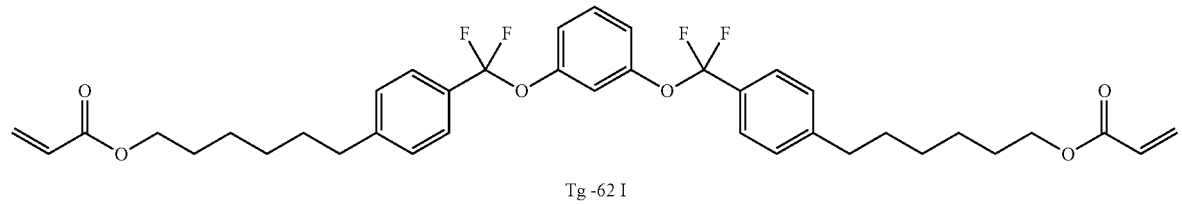
Tg -62 I

(24)
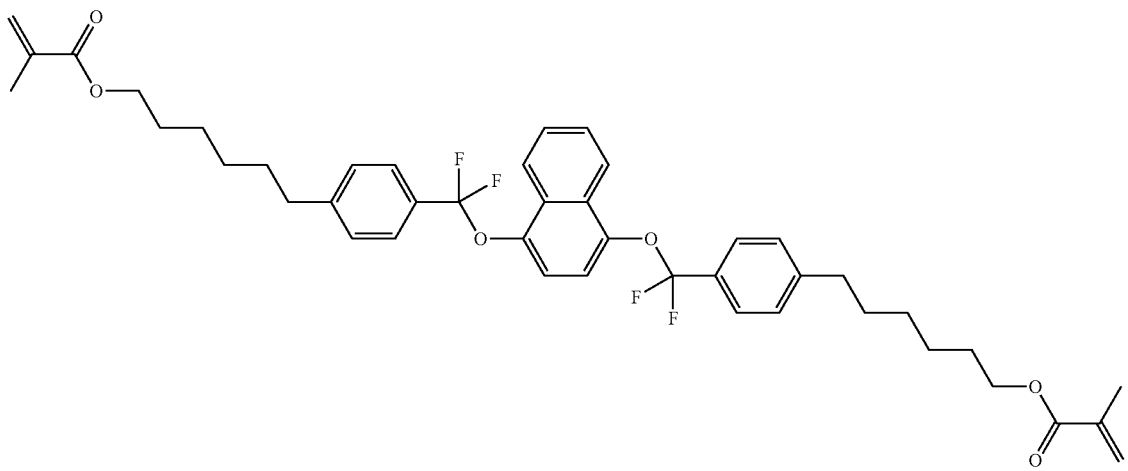
C 40 I
(25)
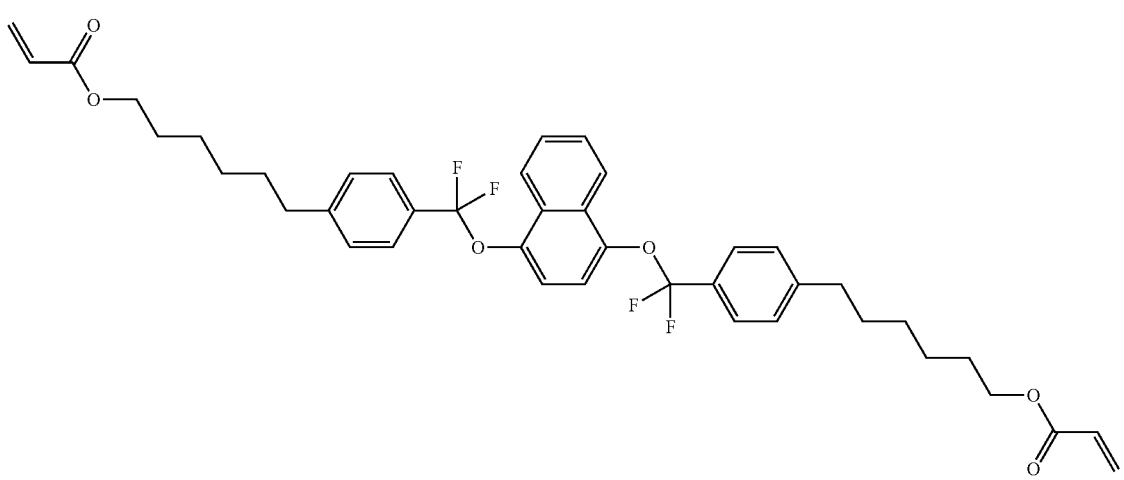
Tg -49 C 30 N (-18.6) I
(26)
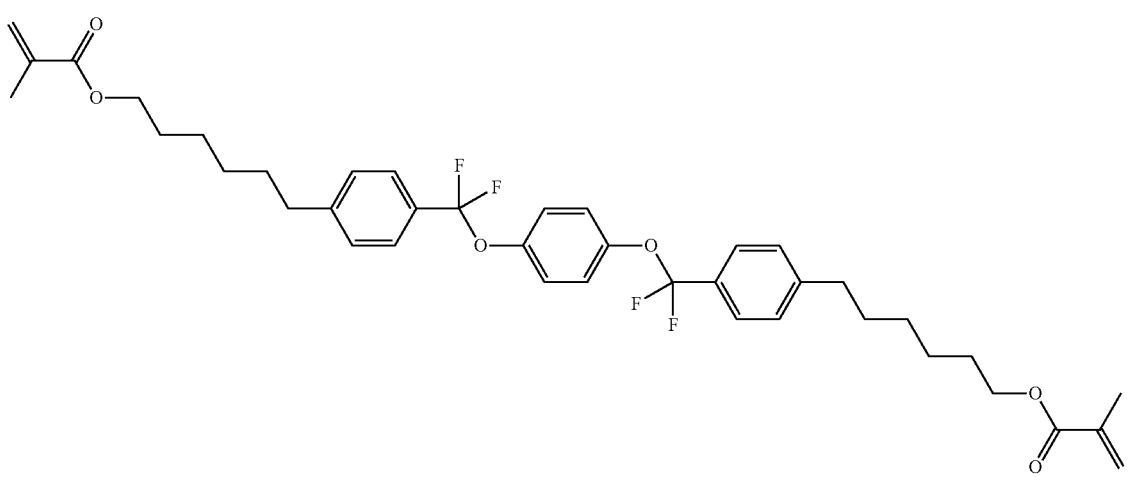
C 41 SmB 43 I

(27)
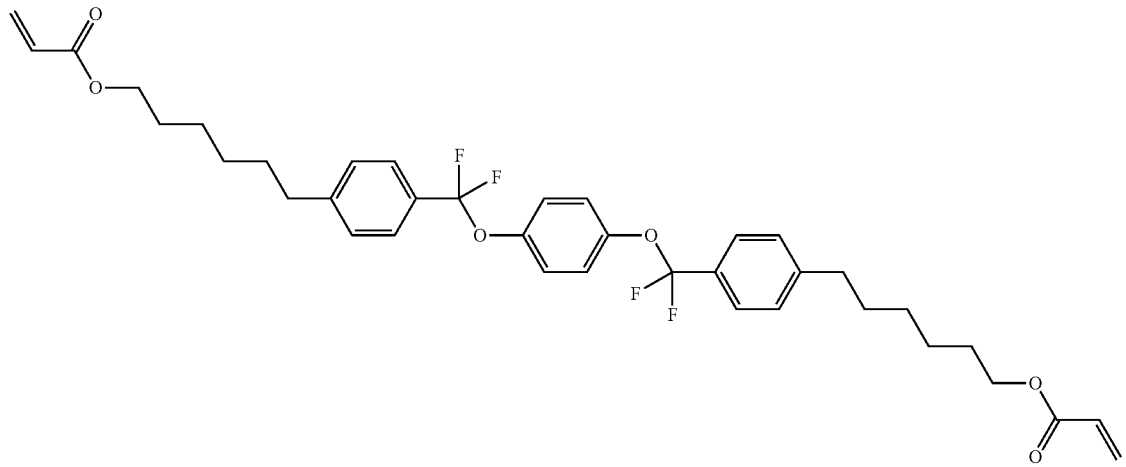
C 46 SmB (43) I
Use Example 1
The following monomers are used:
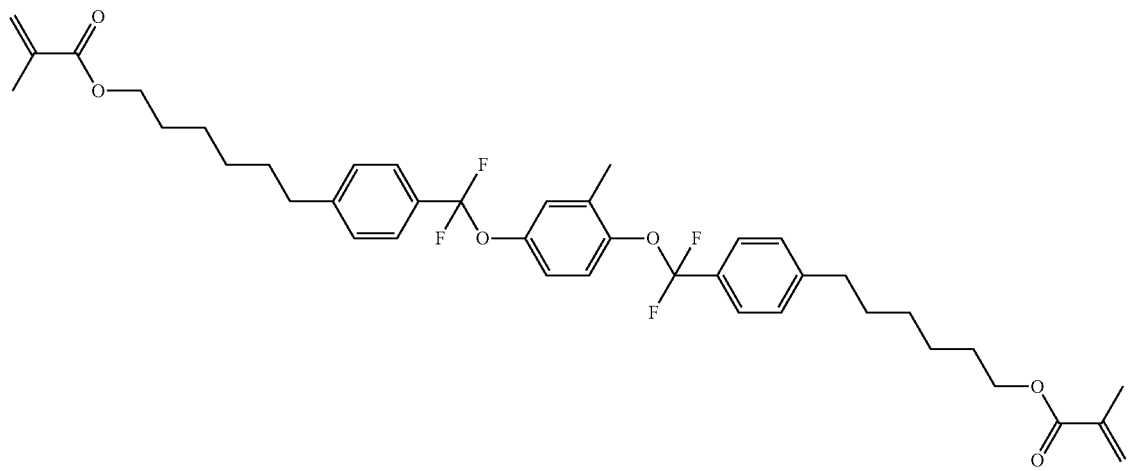
Tg -63 C 12 N (-1) I
Monomer (5) from Example 5
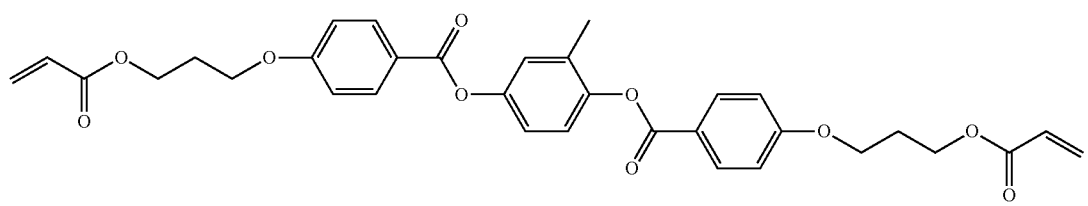
C 66 N 127 I
RM257

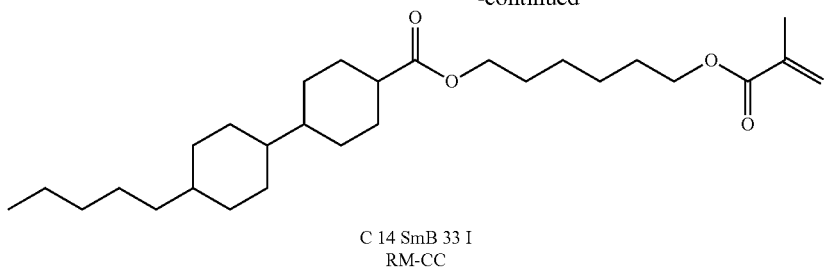

C 14 SmB 33 I
RM-CC

The following additives are used:

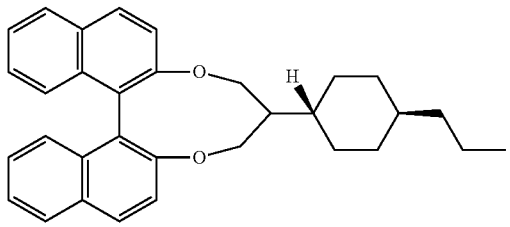

Dp (chiral dopant)

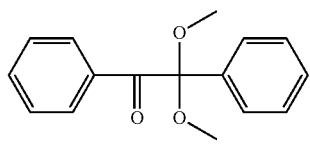

In (Ciba Irgacure ® 651, photoinitiator)

The following base mixture (host) H1 is used:

| Composition | | |
|---|---|---|
| Component Acronym | Proportion % by wt. | Properties |
| PUQU-3-F | 5.00 | T(N, I): 66.6° C. |
| AGUQU-3-F | 13.00 | Δn (20° C., 589 nm): 0.148 |
| AUUQU-2-F | 6.00 | |
| AUUQU-3-F | 10.00 | |
| AUUQU-4-F | 6.00 | |
| AUUQU-5-F | 9.00 | |
| AUUQU-7-F | 6.00 | |
| AUUQU-3-T | 8.00 | |
| AUUQU-3-OT | 12.00 | |
| PUZU-2-F | 6.00 | |
| PUZU-3-F | 10.00 | |
| PUZU-5-F | 9.00 | |
| Σ | 100.00 | |

The polymerisable LC mixture M1 according to the invention, comprising monomer (5) according to the invention from Example 5, and comparative mixtures C1-C3, comprising monomer RM257 from the prior art, are prepared from the base mixture H1 by admixing the monomers and additives mentioned above. The compositions of the mixtures are shown in Table 1.

TABLE 1

| Component | M1 | C1 | C2 | C3 |
|---|---|---|---|---|
| | Proportion [% by weight] | | | |
| H1 | 85 | 85 | 85 | 86.3 |
| Dp | 3.8 | 3.8 | 3.8 | 2.5 |
| In | 0.2 | 0.2 | 0.2 | 0.2 |
| (5) | 6.0 | 0 | 0 | 0 |
| RM257 | 0 | 6.0 | 5.0 | 5.0 |
| RM-CC | 5.0 | 5.0 | 6.0 | 6.0 |

The mixtures are characterised as described below before the polymerisation. The reactive components are then polymerised in the blue phase by irradiation once (180 s), and the resultant media are re-characterised.

Description of the Polymerisation

Before the polymerisation of a sample, the phase properties of the medium are established in a test cell having a thickness of about 10 microns and an area of 2×2.5 cm. The filling is carried out by capillary action at a temperature of 75° C. The measurement is carried out under a polarising microscope with heating stage with a temperature change of 1° C./min.

The polymerisation of the media is carried out by irradiation with a UV lamp (Dymax, Bluewave 200, 365 nm interference filter) having an effective power of about 3.0 mW/cm$^2$ for 180 seconds. The polymerisation is carried out directly in the electro-optical test cell.

The polymerisation is carried out initially at a temperature at which the medium is in the blue phase I (BP-I). The polymerisation is carried out in a plurality of part-steps, which gradually result in complete polymerisation. The temperature range of the blue phase generally changes during the polymerisation. The temperature is therefore adapted between each part-step so that the medium is still in the blue phase. In practice, this can be carried out by observing the sample under the polarising microscope after each irradiation operation of about 5 s or longer. If the sample becomes darker, this indicates a transition into the isotropic phase. The temperature for the next part-step is reduced correspondingly.

The entire irradiation time which results in maximum stabilisation is typically 180 s at the irradiation power indicated. Further polymerisations can be carried out in accordance with an optimised irradiation/temperature programme.

Alternatively, the polymerisation can also be carried out in a single irradiation step, in particular broad if a blue phase is already present before the polymerisation.

Electro-Optical Characterisation

After the above-described polymerisation and stabilisation of the blue phase, the phase width of the blue phase is determined. The electro-optical characterisation is carried out subsequently at various temperatures within and if desired also outside this range. The test cells used are fitted on one side with interdigital electrodes on the cell surface. The cell gap, the electrode separation and the electrode width are typically each 10 microns. This uniform dimension is referred to below as the gap width. The area covered by electrodes is about 0.4 cm². The test cells do not have an alignment layer.

For the electro-optical characterisation, the cell is located between crossed polarising filters, where the longitudinal direction of the electrodes adopts an angle of 45° to the axes of the polarising filter. The measurement is carried out using a DMS301 (Autronic-Melchers) at a right angle to the cell plane, or by means of a highly sensitive camera on the polarising microscope. In the voltage-free state, the arrangement described gives an essentially dark image (definition 0% transmission).

Firstly, the characteristic operating voltages and then the response times are measured on the test cell. The operating voltage is applied to the cell electrodes in the form of rectangular voltage having an alternating sign (frequency 100 Hz) and variable amplitude, as described below.

The transmission is measured while the operating voltage is increased. The reaching of the maximum value of the transmission defines the characteristic quantity of the operating voltage $V_{100}$. Equally, the characteristic voltage $V_{10}$ is determined at 10% of the maximum transmission. These values are measured at various temperatures in the range of the blue phase.

Relatively high characteristic operating voltages $V_{100}$ are observed at the upper and lower end of the temperature range of the blue phase. In the region of the minimum operating voltage, $V_{100}$ generally only increases slowly with temperature. This temperature range, limited by $T_1$ and $T_2$, is referred to as the usable, flat temperature range (FR). The width of this "flat range" (FR) is $(T_2-T_1)$ and is known as the width of the flat range (WFR).

The precise values of $T_1$ and $T_2$ are determined by the intersections of tangents on the flat curve section FR and the adjacent steep curve sections in the $V_{100}$/temperature diagram.

In the second part of the measurement, the response times during switching on and off ($\tau_{on}$, $\tau_{off}$) are determined. The response time $\tau_{on}$ is defined by the time to achievement of 90% intensity after application of a voltage at the level of $V_{100}$ at the selected temperature. The response time $\tau_{off}$ is defined by the time until the decrease by 90% starting from maximum intensity at $V_{100}$ after reduction of the voltage to 0 V. The response time is also determined at various temperatures in the range of the blue phase.

As further characterisation, the transmission at continuously increasing and falling operating voltage between 0 V and $V_{100}$ is measured at a temperature within the FR. The difference between the two curves is known as hysteresis. The difference in the transmissions at $0.5 \cdot V_{100}$ and the difference in the voltages at 50% transmission are, for example, characteristic hysteresis values and are known as $\Delta T_{50}$ and $\Delta V_{50}$ respectively. Furthermore, the contrast during the first switching-on and during the subsequent switching off is distinguished as the ratio of the respective maximum and minimum transmission.

The results are summarised in Table 2.

TABLE 2

| Measurement values | M1 | C1 | C2 | C3 |
|---|---|---|---|---|
| Transition point before the polymerisation | 32.6 | 44.1 | 44.1 | 49.6 |
| Temperature range of the blue phase | — | — | — | — |
| $V_{10}$ (20° C.) | | | | |

TABLE 2-continued

| Measurement values | M1 | C1 | C2 | C3 |
|---|---|---|---|---|
| $V_{100}$ (20° C.) | 74.6 V | 67.9 V | 80.5 V | 55.3 |
| $\Delta V_{50}$ (20° C.) | 5.7 | 6.5 | 6.9 | 4.2 |
| Contrast, switching on | 403 | 500 | 494 | 45 |
| Contrast, switching off | 371 | 33 | 68 | 50 |
| Gap width | 10 μm | 10 μm | 10 μm | 10 μm |

The polymer-stabilised medium M1, prepared using monomer (5) according to the invention, exhibits a reduction in hysteresis ($\Delta V_{50}$) compared with the polymer-stabilised media C1 and C2 and somewhat lower contrast on switching on and a significant increase in the contrast on switching off compared with the polymer-stabilised media C1-C3, prepared using monomer RM257 from the prior art. In particular, the contrast on switching on and the contrast on switching off in the medium M1 according to the invention are close to one another, which means very good stabilisation of the blue phase. In the case of mixture C3, which is analogous to mixture C2, but comprises less chiral dopant, the contrast during switching on and off is likewise very similar. The lower contrast compared with M1, C1 and C2 is therefore due to the fact that a visible blue phase is present in the case of C3.

It is evident from this that the monomers according to the invention are particularly suitable for the stabilisation of blue phases, in particular in the case of media having a high concentration of chiral dopant.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure[s] of all applications, patents and publications, cited herein and of corresponding German application No. DE 102010018188.9, filed Apr. 26, 2010, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula 13

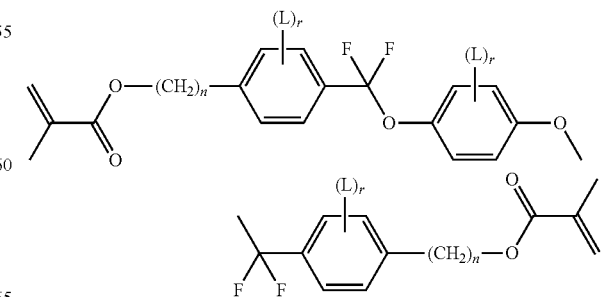

wherein

L on each occurrence, identically or differently, denotes F, Cl, CN, SCN, $SF_5$ or a straight-chain or branched, in each case optionally fluorinated alkyl, alkoxy, alkylcarbonyl, alkoxycarbonyl, alkylcarbonyloxy or alkoxycarbonyloxy having 1 to 12 C atoms, r denotes 0, 1, 2, 3 or 4, and n denotes an integer between 1 and 24;

or a compound of formula 15

(15)

wherein

L on each occurrence, identically or differently, denotes F, Cl, CN, SCN, $SF_5$ or a straight-chain or branched, in each case optionally fluorinated alkyl, alkoxy, alkylcarbonyl, alkoxycarbonyl, alkylcarbonyloxy or alkoxycarbonyloxy having 1 to 12 C atoms, r denotes 0, 1, 2, 3 or 4, and n denotes an integer between 1 and 24;

or compound (5)

(5)

or of formula I $P^a$—$(Sp^a)_{s1}$-$A^2$-$Q^1$-$A^1$-$Q^2$-$A^3$-$(Sp^b)_{s2}$—$P^b$ in which $P^a$, $P^b$ each, independently of one another, denote a polymerizable group, wherein at least one of $P^a$ and $P^b$ is a methacrylate group, $Sp^a$, $Sp^b$ each, independently of one another, denote a spacer group, s1, s2 each, independently of one another, denote 0 or 1, $Q^1$, $Q^2$ each, independently of one another, denote —$CF_2O$— or —$OCF_2$—, $A^1$ denotes a) trans-1,4-cyclohexylene, 1,4-cyclohexenylene or 1,4'-bicyclohexylene, in which optionally one or more non-adjacent $CH_2$ groups are replaced by —O— and/or —S—, and in which one or more H atoms are optionally replaced by F, b1) 1,3-phenylene, in which optionally one or two CH groups are replaced by N and in which one or more H atoms are optionally replaced by L, b2) 1,4-phenylene, in which optionally one or two CH groups are replaced by N and in which one or more H atoms are optionally replaced by L, wherein L is not $CF_2H$ or $CF_3$, c) tetrahydropyran-2,5-diyl, 1,3-dioxane-2,5-diyl, tetrahydrofuran-2, 5-diyl, cyclobut-1,3-diyl, piperidine-1,4-diyl, thiophene-2, 5-diyl or selenophene-2,5-diyl, each of which is optionally mono- or polysubstituted by L, d) bicyclo[1.1.1] pentane-1,3-diyl, bicyclo[2.2.2] octane-1,4-diyl, spiro[3.3]-heptane -2,6-diyl,

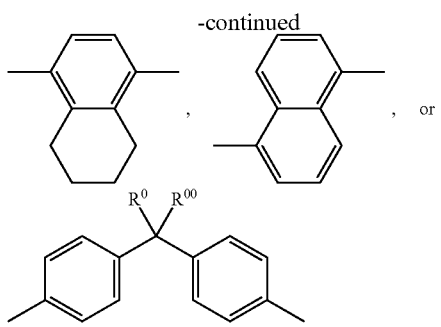

wherein one or more H atoms are optionally replaced by L, and/or one or more double bonds are optionally replaced by single bonds, and/or one or more CH groups are optionally replaced by N, $R^0$, $R^{00}$ each, independently of one another, denote H, F or a straight-chain or branched alkyl having 1 to 12 C atoms, in which one or more H atoms are optionally replaced by F, M denotes —O—, —S—, —$CH_2$—, —$CHY^1$— or —$CY^1Y^2$—, $Y^1$ and $Y^2$ each, independently of one another, denote H, F, $OCF_3$, Cl, CN or a straight-chain or branched alkyl having 1 to 12 C atoms, in which one or more H atoms are optionally replaced by F, $A^2$, $A^3$ each, independently of one another, denote
a) trans-1,4-cyclohexylene, 1,4-cyclohexenylene or 1,4'-bicyclohexylene, in which optionally one or more non-adjacent $CH_2$ groups are replaced by —O— and/or —S—, and in which one or more H atoms are optionally replaced by F,
b) 1,4-phenylene or 1,3-phenylene, in which optionally one or two CH groups are replaced by N and in which one or more H atoms are optionally replaced by L,
c) tetrahydropyran-2,5-diyl, 1,3-dioxane-2,5-diyl, tetrahydrofuran-2,5-diyl, cyclobut-1,3-diyl, piperidine-1,4-diyl, thiophene-2,5-diyl or selenophene-2,5-diyl, each of which is optionally mono- or polysubstituted by L,
d) a saturated, partially unsaturated or fully unsaturated, and optionally substituted, polycyclic radical having 5 to 20 cyclic C atoms, one or more of which are optionally replaced by heteroatoms, and in which
one or more of $A^1$, $A^2$ and $A^3$ are
b1) 1,3-phenylene, in which one or two CH groups are optionally replaced by N and in which optionally one or more H atoms are replaced by L,
or one or more of $A^2$ and $A^3$ are
d) a saturated, partially unsaturated or fully unsaturated, and optionally substituted, polycyclic radicals having 5 to 20 cyclic C atoms, one or more of which are optionally replaced by heteroatoms,
or $A^1$ is,
d) bicyclo[1.1.1]pentane-1,3-diyl, bicyclo[2.2.2]octane-1,4diyl, spiro[3.3]heptane-2,6-diyl,

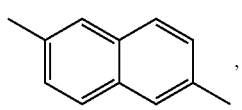

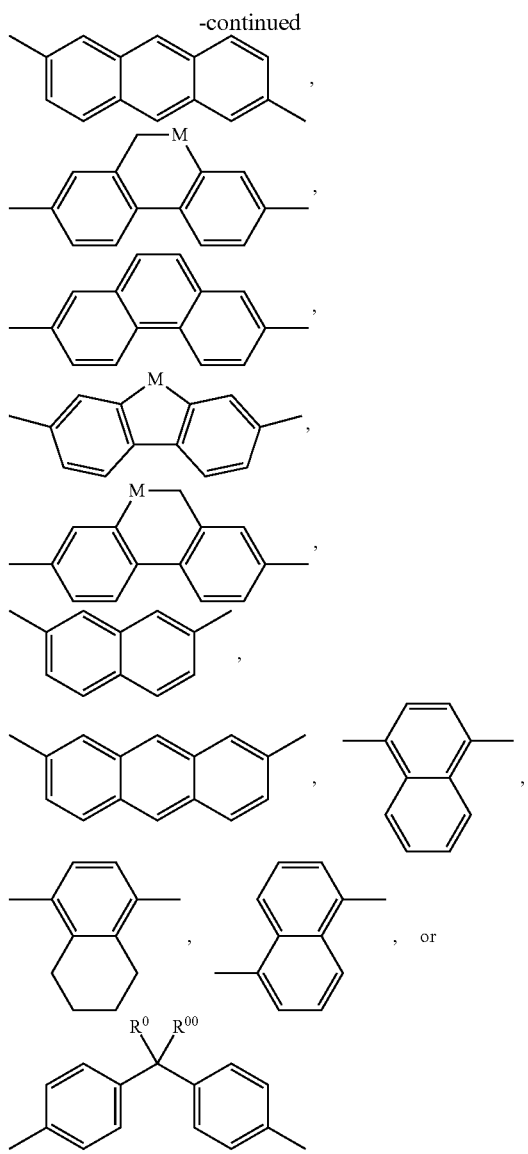

wherein one or more H atoms are optionally replaced by L, and/or one or more double bonds are optionally replaced by single bonds, and/or one or more CH groups are optionally replaced by N, or wherein at least one of the following limitations A) or B) apply A) wherein each of $A^1$, $A^2$ and $A^3$ are 1,4-phenylene, in which optionally one or two CH groups are replaced by N and in which one or more H atoms are optionally replaced by L, and wherein L is not $CF_2H$ or $CF_3$ for $A^1$, B) wherein each of $A^1$, $A^2$ and $A^3$ are 1,4-phenylene, in which one or more H atoms are optionally replaced by L, and wherein L is not $CF_2H$ or $CF_3$ for $A^1$, L on each occurrence, identically or differently, denotes F, Cl, CN, SCN, $SF_5$ or a straight-chain or branched, in each case optionally fluorinated alkyl, alkoxy, alkylcarbonyl, alkoxycarbonyl, alkylcarbonyloxy or alkoxycarbonyloxy having 1 to 12 C atoms.

2. A compound according to claim 1, which is of formula I, and to which limitation A) applies, wherein each of $A^1$, $A^2$ and $A^3$ are 1,4-phenylene, in which optionally one or two CH groups are replaced by N and in which one or more H atoms are optionally replaced by L, and wherein L is not $CF_2H$ or $CF_3$ for $A^I$.

3. A compound according to claim 1, which is of formula I, and to which limitation B) applies, wherein each of $A^I$, $A^2$ and $A^3$ are 1,4-phenylene, in which one or more H atoms are optionally replaced by L, and wherein L is not $CF_2H$ or $CF_3$ for $A^1$.

4. A compound according to claim 1, wherein in the compound of formula I, the spacer is an alkylene group.

5. A compound according to claim 1, wherein in the compound of formula I, both of $P^a$ and $P^b$ are methacrylate groups.

6. A LC display having a blue phase, comprising a compound according to claim 2 or a polymer obtainable by polymerization of said compound.

7. A liquid-crystal (LC) medium, comprising
one or more compounds according to claim 2, which are polymerizable,
or a polymer obtainable by polymerization of said one or more compounds, which are polymerizable,
and one or more additional polymerizable compounds, which are not of formula I to which limitation A) applies, wherein each of $A^1$, $A^2$ and $A^3$ are 1,4-phenylene, in which optionally one or two CH groups are replaced by N and in which one or more H atoms are optionally replaced by L, and wherein L is not $CF_2H$ or $CF_3$ for $A^1$,
and/or one or more additional liquid-crystalline compounds, which are not of formula I to which limitation A) applies, wherein each of $A^1$, $A^2$ and $A^3$ are 1,4-phenylene, in which optionally one or two CH groups are replaced by N and in which one or more H atoms are optionally replaced by L, and wherein L is not $CF_2H$ or $CF_3$ for $A^I$.

8. A LC display having a blue phase, comprising a compound according to claim 3 or a polymer obtainable by polymerization of said compound.

9. A liquid-crystal (LC) medium, comprising
one or more compounds according to claim 3, which are polymerizable,
or a polymer obtainable by polymerization of said one or more compounds, which are polymerizable,
and one or more additional polymerizable compounds, which are not of formula I to which limitation B) applies, wherein each of $A^1$, $A^2$ and $A^3$ are 1,4-phenylene, in which one or more H atoms are optionally replaced by L, and wherein L is not $CF_2H$ or $CF_3$ for $A^1$,
and/or one or more additional liquid-crystalline compounds, which are not of formula I to which limitation B) applies, wherein each of $A^I$, $A^2$ and $A^3$ are 1,4-phenylene, in which one or more H atoms are optionally replaced by L, and wherein L is not $CF_2H$ or $CF_3$ for $A^1$.

10. A LC display having a blue phase, comprising a compound according to claim 4 or a polymer obtainable by polymerization of said compound.

11. A liquid-crystal (LC) medium, comprising
one or more compounds according to claim 4, which are polymerizable,
or a polymer obtainable by polymerization of said one or more compounds, which are polymerizable,
and one or more additional polymerizable compounds, which are not of formula I, in which the spacer is an alkylene group,
and/or one or more additional liquid-crystalline compounds, which are not of formula I, in which the spacer is an alkylene group.

12. A LC display having a blue phase, comprising a compound according to claim 5 or a polymer obtainable by polymerization of said compound.

13. A liquid-crystal (LC) medium, comprising
one or more compounds according to claim 5, which are polymerizable,
or a polymer obtainable by polymerization of said one or more compounds, which are polymerizable,
and one or more additional polymerizable compounds, which are not of formula I, in which both of Pa and Pb are methacrylate groups,
and/or one or more additional liquid-crystalline compounds, which are not of formula I, in which both of $P^a$ and $P^b$ are methacrylate groups.

14. A compound according to claim 1, which is compound (5)

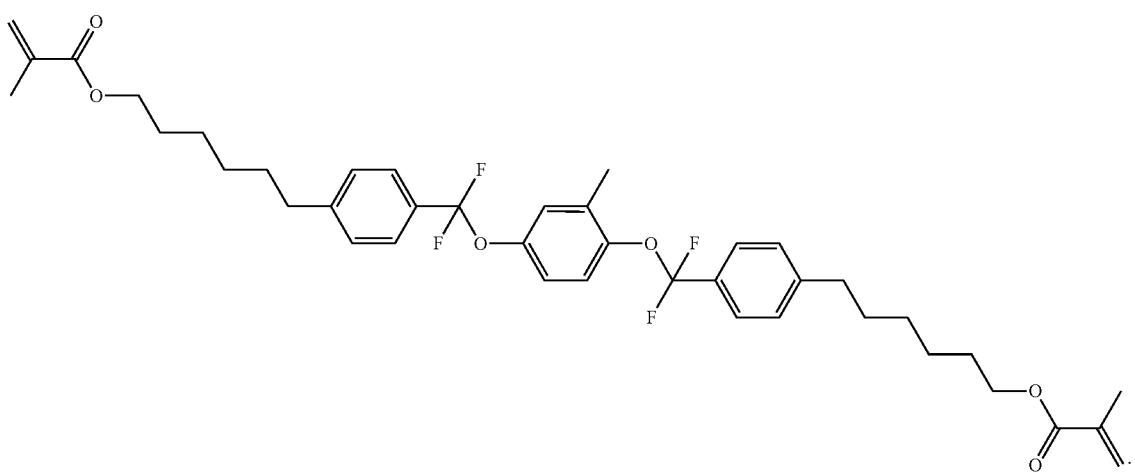

(5)

15. A LC display having a blue phase, comprising a compound according to claim 14 or a polymer obtainable by polymerization of said compound.

16. A liquid-crystal (LC) medium, comprising
a compound according to claim 14, which is polymerizable,
or a polymer obtainable by polymerization of said compound, which is polymerizable,
and one or more additional polymerizable compounds, which are not of formula (5),
and/or one or more additional liquid-crystalline compounds, which are not of formula (5).

17. A LC display having a blue phase, comprising a compound according to claim 1 or a polymer obtainable by polymerization of said compound.

18. A liquid-crystal (LC) medium, comprising
one or more compounds according to claim 1, which are of formula 13, 15, (5) or I, and which are polymerizable,
or a polymer obtainable by polymerization of said one or more polymerizable compounds of formula 13, 15, (5) or I,
and one or more additional polymerizable compounds, which are not of formula 13, 15, (5) or I,
and/or one or more additional liquid-crystalline compounds, which are not of formula 13, 15, (5) or I.

19. A LC medium according to claim 18, further comprising one or more optically active and/or chiral compounds, and comprising, as the one or more additional polymerizable compounds and/or one or more additional liquid-crystalline compounds, one or more liquid crystalline compounds of formula II and optionally one or more liquid crystalline compounds of formula III:
one or more liquid crystalline compounds of formula II

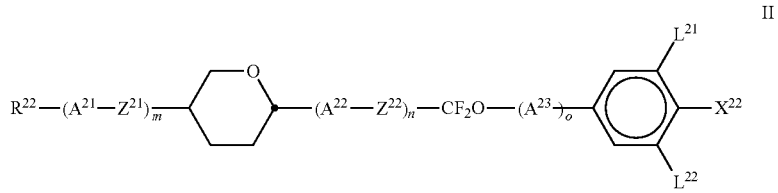

in which
$R^{22}$ denotes H, F, Cl, CN, NCS, $SF_5$, $SO_2CF_3$ or a straight-chain or branched alkyl having 1 to 20 C atoms, which is unsubstituted or mono- or polysubstituted by F, Cl or CN, and in which one or more non-adjacent $CH_2$ groups are optionally replaced, independently of one another, by —O—, —S—, —NH—, —$NR^{01}$—, —$SiR^{01}R^{02}$—, —CO—, —COO—, —OCO—, —OCO—O—, —S—CO—, —CO—S—, —$CY^{01}$=$CY^{02}$— or —C≡C— in such a way that O and/or S atoms are not linked directly to one another, $Y^{01}$, $Y^{02}$ each, independently of one another, denote F, Cl or CN, one of the radicals $Y^{01}$ and $Y^{02}$ also denotes H, $R^{01}$, $R^{02}$ each, independently of one another, denote H or alkyl having 1 to 12 C atoms, $A^{21}$, $A^{22}$, $A^{23}$ each, independently of one another and on each occurrence identically or differently, denote one of the following groups

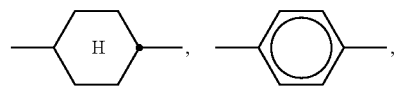

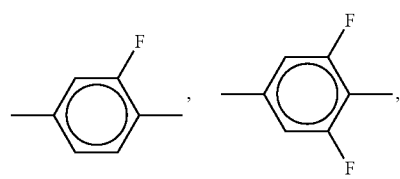

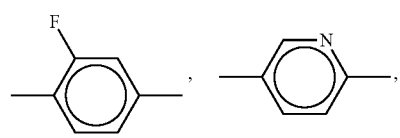

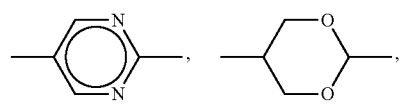

$Z^{21}$, $Z^{22}$ each, independently of one another and on each occurrence identically or differently, denote a single bond, —$(CH_2)_4$—, —$CH_2CH_2$—, —$CF_2$—$CF_2$—, —$CF_2$—$CH_2$—, —$CH_2$—$CF_2$—, —CH=CH—, —CF=CF—, —CF=CH—, —$(CH_2)_3O$—, —$O(CH_2)_3$—, —CH=CF—, —$CH_2O$—, —$OCH_2$—, —$CF_2O$—, —$OCF_2$—, —CO—O— or —O—CO—, $X^{22}$ denotes F, Cl, —CN, —NCS, —$SF_5$, —$SO_2CF_3$, or alkyl, alkenyl, alkenyloxy, alkylalkoxy or alkoxy having 1 to 3 C atoms, which is mono- or polysubstituted by F, Cl or CN, $L_{21}$, $L_{22}$ each, independently of one another, denote H or F, m denotes 0, 1 or 2, n denotes 0, 1, 2 or 3, o denotes 0, 1 or 2, where m +n +o denotes 0, 1, 2 or 3, optionally one or more liquid crystalline compounds of formula III

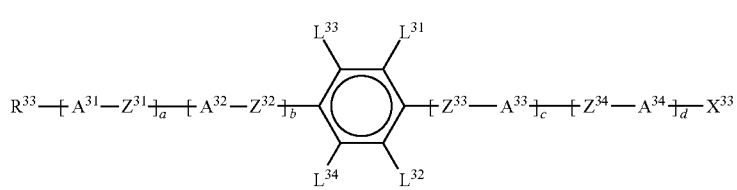

III in which a, b, c, d each, independently of one another, denote 0, 1 or 2, where a+b+c+d is 0, 1, 2, 3 or 4, $A^{31}, A^{32}, A^{33}, A^{34}$ each, independently of one another and on each occurrence identically or differently, denote one of the following groups

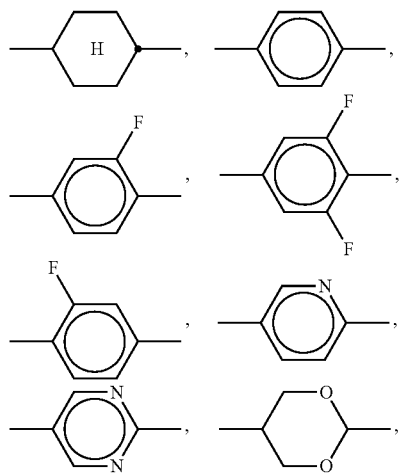

$Z^{31}, Z^{32}, Z^{33}, Z^{34}$ each, independently of one another and on each occurrence identically or differently, denote a single bond, —(CH$_2$)—, —CH$_2$CH$_2$—, —CF$_2$—CF$_2$—, —CF$_2$—CH$_2$—, —CH$_2$—CF$_2$—, —CH=CH—, —CF=CF—, —CF=CH—, —(CH$_2$)$_3$O—, —O(CH$_2$)$_3$—, —CH=CF—, —C≡C—, —CH$_2$O—, —OCH$_2$—, —CF$_2$O—, —OCF$_2$—, —CO—O— or —O—CO—, $R^{33}$ denotes alkyl or alkoxy having 1 to 15 C atoms, which is unsubstituted or mono- or polysubstituted by F, Cl or CN, and in which one or more non-adjacent CH$_2$ groups are optionally replaced, each independently of one another, by —O—, —S—, —SiR$^x$R$^y$—, —CH=CH—, —C≡C—, —CO—O— and/or —O—CO— in such a way that O and/or S atoms are not linked directly to one another, $L^{31}, L^{32}, L^{33}, L^{34}$ each, independently of one another, denote H, F, Cl, CN or alkyl or alkoxy having 1 to 15 C atoms, which is unsubstituted or mono- or polysubstituted by F, Cl or CN and in which one or more non-adjacent CH$_2$ groups are optionally replaced, independently of one another, by —O—, —S—, —SiR$^x$R$^y$—, —CH=CH—, —C≡C— and/or —O—CO— in such a way that O and/or S atoms are not linked directly to one another, with the proviso that at least one of the radicals $L^{31}, L^{32}, L^{33}$ and $L^{34}$ is other than H, $X^{33}$ denotes F, Cl, CF$_3$, OCF$_3$, CN, NCS, —SF$_5$ or —SO$_2$—R$^z$, $R^x$ and $R^y$ each, independently of one another, denote H, alkyl or alkoxy having 1 to 7 C atoms, and $R^z$ denotes alkyl having 1 to 7 C atoms, which is unsubstituted or mono- or polysubstituted by F or Cl.

20. A LC medium according to claim 18, comprising, as the one or more additional polymerizable compounds and/or one or more additional liquid-crystalline compounds, one or more liquid crystalline compounds of formulae Z, Q1 and/or Q2:

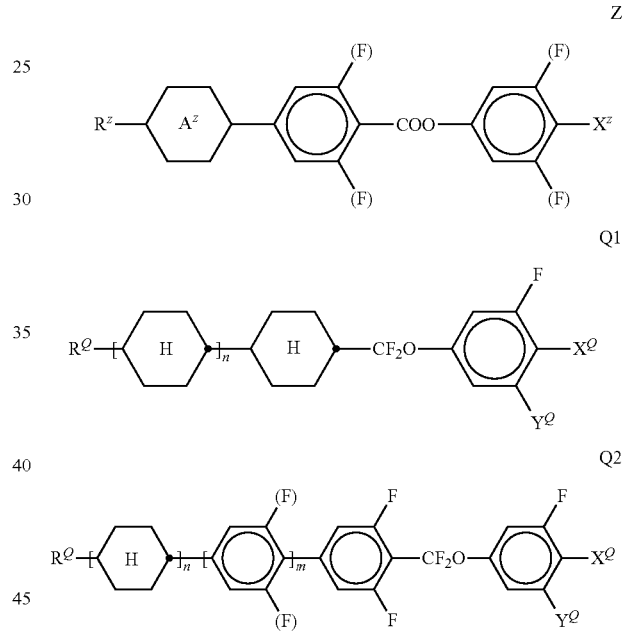

in which $R^z$ denotes H, F, Cl, CN, NCS, SF$_5$, SO$_2$CF$_3$ or a straight-chain or branched alkyl having 1 to 20 C atoms, which is unsubstituted or mono- or polysubstituted by F, Cl or CN, and in which one or more non-adjacent CH$_2$ groups are optionally replaced, independently of one another, by —O—, —S—, —NH—, —NR$^{01}$—, —SiR$^{01}$R$^2$—, —CO—, —COO—, —OCO—, —OCO—O—, —S—CO—, —CO—S—, —CY$^{01}$=CY$^{02}$— or —C≡C— in such a way that O and/or S atoms are not linked directly to one another,

-continued

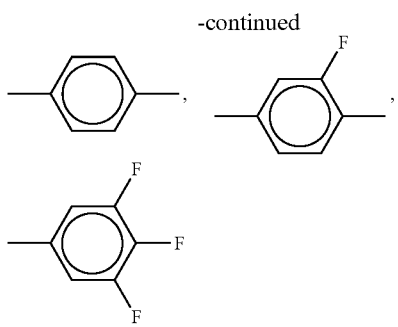

$X^z$ denotes F, Cl, CN, NCS, OCF$_3$, CF$_3$ or SF$_5$, $R^Q$ denotes H, F, Cl, CN, NCS, SF$_5$, SO$_2$CF$_3$ or a straight-chain or branched alkyl having 1 to 20 C atoms, which is unsubstituted or mono- or polysubstituted by F, Cl or CN, and in which one or more non-adjacent CH$_2$ groups are optionally replaced, independently of one another, by —O—, —S—, —NH—, —NR$^{01}$—, —SiR$^{01}$R$^{02}$—, —CO—, —COO—, —OCO—, —OCO—O—, —S—CO—, —CO—S—, —CY$^{01}$=CY$^{02}$— or —C≡C— in such a way that O and/or S atoms are not linked directly to one another, $X^Q$ denotes F, Cl, CN, NCS, OCF$_3$, CF$_3$ or SF$_5$, $Y^Q$ denotes H or F, (F) denotes F or H, and n and m each, independently of one another, denote 0 or 1.

21. A process for preparing an LC medium according to claim 18, comprising mixing together one or more compounds of formula 13, 15, (5) or I, or a polymer obtainable by polymerization of one or more compounds of formula 13, 15, (5) or I, and one or more additional polymerizable compounds and/or one or more additional liquid-crystalline compounds.

22. A LC display containing an LC medium according to claim 18.

23. A LC display according to claim 22, comprising an LC cell having two substrates and two electrodes, where at least one substrate is transparent to light and at least one substrate has one or two electrodes, and a layer, located between the substrates, of an LC medium comprising a polymerized component and a low-molecular-weight component, where the polymerized component is obtainable by polymerization of one or more polymerizable compounds between the substrates of the LC cell in the LC medium, optionally with application of an electrical voltage to the electrodes, wherein at least one of the polymerizable compounds is a polymerizable compound of the formula 13, 15, (5) or I.

24. A process for the production of an LC display according to claim 23, comprising introducing the LC medium into an LC cell having two substrates and two electrodes, and polymerizing the polymerizable compounds, optionally with application of an electrical voltage to the electrodes.

25. A process for preparing a compound of claim 1, comprising a reaction of a compound of formula IA

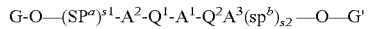

in which

Sp$^a$, Sp$^b$ each, independently of one another, denote a spacer group, s1, s2 each, independently of one another, denote 0 or 1, Q$^1$, Q$^2$ each, independently of one another, denote —CF$_2$O— or —OCF$_2$—, A$^1$, A$^2$, A$^3$ each, independently of one another, denote a) trans-1,4-cyclohexylene, 1,4-cyclohexenylene or 1,4'-bicyclohexylene, in which optionally one or more non-adjacent CH$_2$ groups are replaced by —O— and/or —S—, and in which one or more H atoms are optionally replaced by F, b) 1,4-phenylene or 1,3-phenylene, in which optionally one or two CH groups are replaced by N and in which one or more H atoms are optionally replaced by L, c) tetrahydropyran-2,5-diyl, 1,3-dioxane-2,5-diyl, tetrahydrofuran-2,5-diyl, cyclobut-1,3-diyl, piperidine-1,4-diyl, thiophene-2,5-diyl or selenophene-2,5-diyl, each of which is optionally mono- or polysubstituted by L, d) a saturated, partially unsaturated or fully unsaturated, and optionally substituted, polycyclic radical having 5 to 20 cyclic C atoms, one or more of which are optionally replaced by heteroatoms, L on each occurrence, identically or differently, denotes F, Cl, CN, SCN, SF$_5$ or a straight-chain or branched, in each case optionally fluorinated alkyl, alkoxy, alkylcarbonyl, alkoxycarbonyl, alkylcarbonyloxy or alkoxycarbonyloxy having 1 to 12 C atoms, and G and G' each, independently of one another, denote an H atom or a protecting group with a reagent suitable for the preparation of a compound of formula 13, 15, (5) or I.

26. A process according to claim 25, wherein the reagent suitable for the preparation of a compound of formula 13, 15,(5) or I is acrylic acid or a reactive derivative thereof.

27. A process according to claim 25, wherein the reagent suitable for the preparation of a compound of formula 13, 15,(5) or I is methacrylic acid or a reactive derivative thereof.

28. A process according to claim 25, wherein the reagent suitable for the preparation of a compound of formula 13, 15,(5) or I is alkyleneglycol or a reactive derivative thereof.

29. A LC medium comprising one or more compounds according to claim 1 and one or more further liquid-crystalline compounds.

30. A LC display containing one or more compounds according to claim 1.

31. A LC display according to claim 30, wherein in the compound of formula I,

Y$^1$ and Y$^2$ each, independently of one another, denote H, F, Cl, CN, OCF$_3$ or CF$_3$, wherein only one of Y$^1$ and Y$^2$ can be OCF$_3$.

32. A LC medium according to claim 29, wherein in the compound of formula I,

Y$^1$ and Y$^2$ each, independently of one another, denote H, F, Cl, CN, OCF$_3$ or CF$_3$, wherein only one of Y$^1$ and Y$^2$ can be OCF$_3$.

33. A compound according to claim 1, wherein in the compound of formula I,

Y$^1$ and Y$^2$ each, independently of one another, denote H, F, Cl, CN, OCF$_3$ or CF$_3$, wherein only one of Y$^1$ and Y$^2$ can be OCF$_3$.

34. A LC medium according to claim 19, wherein m +n +o denotes 0, 1 or 2, and/or R$^{33}$ denotes a straight-chain alkyl, alkoxy, alkenyl, alkenyloxy or —O-alkylene-O— radical having up to 10 C atoms, which is unsubstituted or mono- or polysubstituted by F or Cl, and/or $R^x$ and $R^Y$ each, independently of one another, denote methyl, ethyl, propyl or butyl, and/or $R^Z$ denotes $CF_3$, $C_2F_5$ or $n$-$C_4F_9$.

35. A LC medium according to claim 18, which does not comprise any compounds of the following formula

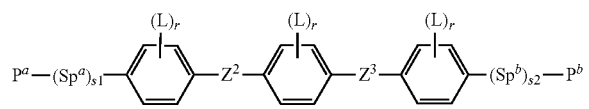

M in which $P^a$, $P^b$ each, independently of one another, denote a polymerizable group, $Sp^a$, $sp^b$ each, independently of one another, denote a spacer group, s1,s2 each, independently of one another, denote 0 or 1, L on each occurrence, identically or differently, denotes F, Cl, CN, SCN, $SF_5$ or a straight-chain or branched, in each case optionally fluorinated alkyl, alkoxy, alkylcarbonyl, alkoxycarbonyl, alkylcarbonyloxy or alkoxycarbonyloxy having 1 to 12 C atoms, r denotes 0, 1, 2, 3 or 4, and $Z^2$ and $Z^3$ each, independently of one another, denote —COO— or —OCO—.

36. A compound according to claim 1, wherein in the compound of formula I, $Sp^a$, $Sp^b$ each, independently of one another, denote alkylene having 1 to 20, which is optionally mono- or polysubstituted by F, Cl, Br, I or CN, and in which one or more non-adjacent $CH_2$ groups are optionally each replaced, independently of one another, by —O—, —S—, —NH—, —Si($R^{00*}$ $R^{000*}$)—, —CO—, —CO—O—, —O—CO—, —O—CO—O—, —S—CO—, —CO—S—, —N($R^{00*}$)—CO—O—, —O—CO—N($R^{00*}$)—, or —N($R^{00*}$)—CO—N ($R^{00*}$)—, in such a way that O and/or S atoms are not linked directly to one another.

37. A compound according to claim 1, which is of formula I3

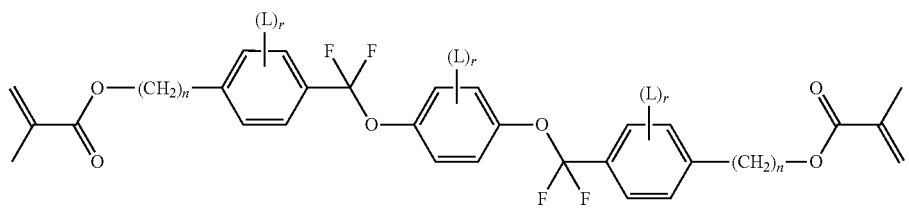

I3 wherein

L on each occurrence, identically or differently, denotes F, Cl, CN, SCN, $SF_5$ or a straight-chain or branched, in each case optionally fluorinated alkyl, alkoxy, alkylcarbonyl, alkoxycarbonyl, alkylcarbonyloxy or alkoxycarbonyloxy having 1 to 12 C atoms, r denotes 0, 1, 2, 3 or 4, and n denotes an integer between 1 and 24.

38. A compound according to claim 1, which is of formula I5

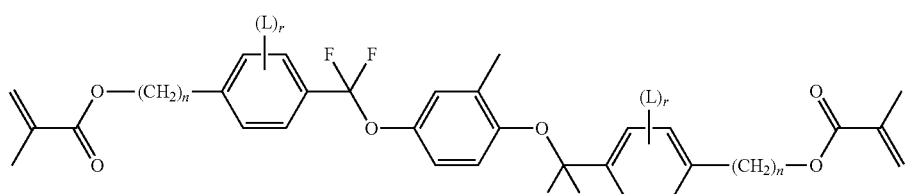

I5 wherein

L on each occurrence, identically or differently, denotes F, Cl, CN, SCN, $SF_5$ or a straight-chain or branched, in each case optionally fluorinated alkyl, alkoxy, alkylcarbonyl, alkoxycarbonyl, alkylcarbonyloxy or alkoxycarbonyloxy having 1 to 12 C atoms, r denotes 0, 1, 2, 3 or 4, and n denotes an integer between 1 and 24.

39. A LC display having a blue phase, comprising a compound according to claim 37 or a polymer obtainable by polymerization of said compound.

40. A liquid-crystal (LC) medium, comprising one or more compounds according to claim 37, which are polymerizable, or a polymer obtainable by polymerization of said one or more compounds, which are polymerizable, and one or more additional polymerizable compounds, which are not of formula 13, and/or one or more additional liquid-crystalline compounds, which are not of formula 13.

41. A LC display having a blue phase, comprising a compound according to claim 38 or a polymer obtainable by polymerization of said compound.

42. A liquid-crystal (LC) medium, comprising one or more compounds according to claim 24, which are polymerizable, or a polymer obtainable by polymerization of said one or more compounds, which are polymerizable, and one or more additional polymerizable compounds, which are not of formula 15, and/or one or more additional liquid-crystalline compounds, which are not of formula 15.

\* \* \* \* \*